(12) United States Patent
Herbert et al.

(10) Patent No.: US 7,994,199 B2
(45) Date of Patent: Aug. 9, 2011

(54) HETEROCYCLIC COMPOUNDS, METHODS FOR THE PREPARATION THEREOF, AND USES THEREOF

(75) Inventors: Brian Herbert, Stockholm, NJ (US); Wenge Xie, Mahwah, NY (US); Truc Minh Nguyen, New York, NY (US); Allen T Hopper, Glen Rock, NJ (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 0 days.

(21) Appl. No.: 12/724,754

(22) Filed: Mar. 16, 2010

(65) Prior Publication Data

US 2010/0173891 A1 Jul. 8, 2010

Related U.S. Application Data

(60) Continuation of application No. 11/783,193, filed on Apr. 6, 2007, now Pat. No. 7,700,630, which is a division of application No. 10/651,023, filed on Aug. 29, 2003, now Pat. No. 7,244,745.

(60) Provisional application No. 60/406,981, filed on Aug. 30, 2002.

(51) Int. Cl.
*C07D 401/02* (2006.01)
*A61K 31/44* (2006.01)

(52) U.S. Cl. ......... 514/333; 514/334; 546/256; 546/257

(58) Field of Classification Search .................. None
See application file for complete search history.

(56) References Cited

U.S. PATENT DOCUMENTS

| | | | |
|---|---|---|---|
| 5,559,124 | A | 9/1996 | Bencherif et al. |
| 5,602,257 | A | 2/1997 | Zoltewicz et al. |
| 5,734,059 | A | 3/1998 | Watanabe et al. |
| 5,741,802 | A | 4/1998 | Kem et al. |
| 5,977,144 | A | 11/1999 | Meyer et al. |
| 2002/0028798 | A1 | 3/2002 | Demopulos et al. |

FOREIGN PATENT DOCUMENTS

| | | |
|---|---|---|
| CA | 2361437 | 8/2000 |
| DE | 196 22 353 | 12/1997 |
| WO | WO 92/15306 | 9/1992 |
| WO | WO 94 05288 | 3/1994 |
| WO | WO 98 03484 | 1/1998 |
| WO | WO 99 10338 | 3/1999 |
| WO | WO 01/73446 | 10/2001 |
| WO | WO 03 057140 | 7/2003 |

OTHER PUBLICATIONS

W. R. Kem, "The brain alpha7 nicotinic receptor may be an important therapeutic target for the treatment of Alzheimer's disease: studies with DMXBA (GTS-21)", Behavioural Brain Research, Elsevier, vol. 113, No. 1/2, 2000, pp. 169-181.
C. De Fiebre, et al., "Characterization of a series of Anabaseine-derived compounds reveals that the 3-(4)-dimethylaminocin-namylidine derivative . . . ", Molecular Pharm., vol. 47, No. 1, 1995, pp. 164-171.
Jeffrey D. Schmitt et al., "Chapter 5. Targeting Nicotinic Acetylcholine Receptors: Advances in Molecular Design and Therapies" *Annual Reports in Medicinal Chemistry*-35, pp. 41-51, 2000.
Mark W. Holladay et al., "Neuronal Nicotinic Acetylcholine Receptors as Targets for Drug Discovery" *Journal of Medicinal Chemistery*, 1997, vol. 40, No. 26, pp. 4169-4194.
Michael W. Decker et al., "Neuronal Nicotinic Acetylcholine Receptors: Novel Targets for CNS Therapeutics" *Neuronal Nicotinic Acetylcholine Receptors: Novel Targets for CNS Therapeutics*, 2000, pp. 1-14.
Dwight Flammia et al., "lobeline: Structure-Affinity Investigation of Nicotinic Acetylcholinergic Receptor Binding" *J. Med. Chem.* 1999, vol. 42, No. 18, pp. 3726-3731.
R. Azuma et al., "Metabolism and Disposition of GTS-21, a novel drug for Alzheimer's disease" *Xenobiotica*, 1999, vol. 29, No. 7, pp. 747-762.
Karen E. Stevens et al., "Selective $\alpha_7$-nicotinic agonists normalize inhibition of auditory response in DBA mice" *Psychopharmacology* 1998, No. 136, pp. 320-327.
Ryotaro Azuma et al., "The effect of repeat administration of GTS-21 on mixed-function oxidase activities in rat", *Toxicology Letters 110*, 1999, pp. 137-144.
Alberici et al., Tet. Lett, 24(18) (1983), pp. 1937-1940.
De Kimpe, et al., Tet. Lett. 34(29) (1993), pp. 4693-4696.
Leete, J. org. Chem., 44(2), (1979), pp. 165-168.
Mundy et al., Synthetic Commun., 2(4), (1972), pp. 197-200.
Sultana et al., Biorganic & Medicinal Chemistry, 10 (2002), pp. 2963-2971.
Villemin et al., React. Kinet. Catal. Lett, 72(1), (2001), pp. 3-10.
Zoltewicz et al., Heterocycles, vol. 35, No. 1 (1993), pp. 171-180.
Zoltewicz et al., J. org. Chem., (1989), 54, pp. 4462-4468.
Zoltewicz et al., OPPI Briefs, 27, 4 (1995), pp. 510-513.
Thomson Innovation, English Translation of Claims and Description, Retrieved from Thomson Innovation Record View on Jun. 16, 2010; English Abstract of DE19622353.

*Primary Examiner* — Zinna Northington Davis
(74) *Attorney, Agent, or Firm* — Millen, White, Zelano & Branigan, P.C.

(57) ABSTRACT

The compounds of the present invention are of formula I:

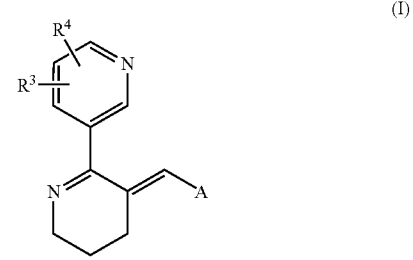

(I)

wherein A, $R^3$, $R^4$ is as defined herein, are useful as ligands for nicotinic receptors.

14 Claims, No Drawings

HETEROCYCLIC COMPOUNDS, METHODS FOR THE PREPARATION THEREOF, AND USES THEREOF

This application is a continuation of U.S. patent application Ser. No. 11/783,193, filed Apr. 6, 2007, now U.S. Pat. No. 7,700,630, which is a divisional of U.S. patent application Ser. No. 10/651,023, filed Aug. 29, 2003 (U.S. Pat. No. 7,244,745), which claims benefit of 60/406,981, filed Aug. 30, 2002.

FIELD OF THE INVENTION

The present invention relates generally to the field of ligands for nicotinic acetylcholine receptors (nAChR), activation of nAChRs, and the treatment of disease conditions associated with defective or malfunctioning nicotinic acetylcholine receptors, especially of the brain. Further, this invention relates to novel compounds which act as ligands for the α7nAChR subtype, e.g., anabaseine analogs, methods of preparing such compounds, compositions containing such compounds, and methods of use thereof.

BACKGROUND OF THE INVENTION

There are two types of receptors for the neurotransmitter, acetylcholine: muscarinic receptors and nicotinic receptors, based on the selectivity of action of muscarine and nicotine, respectively. Muscarinic receptors are G-protein coupled receptors. Nicotinic receptors are members of the ligand-gated ion channel family. When activated, the conductance of ions across the nicotinic ion channels increases.

Nicotinic alpha-7 receptor protein forms a homo-pentameric channel in vitro that is highly permeable to a variety of cations (e.g., $Ca^{++}$). Each nicotinic alpha-7 receptor has four transmembrane domains, named M1, M2, M3, and M4. The M2 domain has been suggested to form the wall lining the channel. Sequence alignment shows that nicotinic alpha-7 is highly conserved during evolution. The M2 domain that lines the channel is identical in protein sequence from chicken to human. For discussions of the alpha-7 receptor, see, e.g., Revah et al. (1991), *Nature,* 353, 846-849; Galzi et al. (1992), *Nature* 359, 500-505; Fucile et al. (2000), *PNAS* 97(7), 3643-3648; Briggs et al. (1999), *Eur. J. Pharmacol.* 366 (2-3), 301-308; and Gopalakrishnan et al. (1995), *Eur. J. Pharmacol.* 290(3), 237-246.

The nicotinic alpha-7 receptor channel is expressed in various brain regions and is believed to be involved in many important biological processes in the central nervous system (CNS), including learning and memory. Nicotinic alpha-7 receptors are localized on both presynaptic and postsynaptic terminals and have been suggested to be involved in modulating synaptic transmission. It is therefore of interest to develop novel compounds, which act as ligands for the α7 nAChR subtype, for the treatment of disease conditions associated with defective or malfunctioning nicotinic acetylcholine receptors.

SUMMARY OF THE INVENTION

The present invention includes compounds of Formula I:

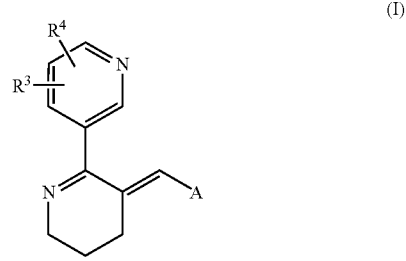

wherein
A is
(a) phenyl or pyridyl, each of which is substituted by a 5 to 7 membered heterocyclic ring containing an O, S, or N ring atom, and optionally containing a further N ring atom, wherein the heterocyclic ring is fully unsaturated, partially saturated or fully saturated and is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms (e.g., 3 to 8 carbon atoms), cycloalkylalkyl having 4 to 14 carbon atoms (e.g., 4 to 8 carbon atoms), Ar-alkyl wherein alkyl portion has 1 to 8 carbon atoms (e.g., benzyl, phenethyl), Het-alkyl wherein alkyl portion has 1 to 8 carbon atoms, $COR^5$, $COOR^5$, $CONR^5R^6$, halogen, cyano, hydroxyl, $NR^1R^2$, nitro, oxo, thio, alkylthio (e.g., —S—$CH_3$), alkylsulfinyl (e.g., —SO—$CH_3$), alkylsulfonyl (e.g., —$SO_2$—$CH_3$), Ar, Het or combinations thereof, wherein the heterocyclic ring may be bridged by a divalent alkylene group having 1 to 3 carbon atoms (e.g., 2,5-diazabicyclo[2.2.1]hept-2-yl),
wherein said phenyl or pyridyl is optionally further substituted by one or more substituents selected from halogen, alkyl having 1 to 4 carbon atoms, alkoxy having 1 to 4 carbon atoms, $NR^1R^2$, nitro, hydroxyl, and cyano, and
wherein said 5 to 7 membered heterocyclic ring is optionally fused with an aryl group or heteroaryl group which in each case contains 5 to 10 ring atoms and in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms (e.g., 3 to 8 carbon atoms), cycloalkylalkyl having 4 to 14 carbon atoms (e.g., 4 to 8 carbon atoms), Ar-alkyl wherein alkyl portion has 1 to 8 carbon atoms, Het-alkyl wherein alkyl portion has 1 to 8 carbon atoms, $COR^5$, $COOR^5$, $CONR^5R^6$, halogen, carboxy, cyano, hydroxyl, $NR^1R^2$, nitro, oxo, thio, Ar, Het and combinations thereof, (b) phenyl or pyridyl which in each case is fused with a 5 to 7 membered heterocyclic ring containing 1 to 3 hetero atoms each selected from O, S, and N, to form a bicyclic group wherein the fused heterocyclic ring is fully unsaturated, partially saturated or fully saturated, and wherein said bicyclic group is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms (e.g., 3 to 8 carbon atoms), cycloalkylalkyl having 4 to 14 carbon atoms (e.g., 4 to 8 carbon atoms), $COR^5$, $COOR^5$, $CONR^5R^6$, halogen, carboxy, cyano, hydroxyl, $NR^1R^2$, nitro, oxo, thio, alkylthio (e.g., $-S-CH_3$), alkylsulfinyl (e.g., $-SO-CH_3$), alkylsulfonyl (e.g., $-SO_2-CH_3$), Ar, Het, Ar-alkyl wherein alkyl portion has 1 to 8 carbon atoms, Het-alkyl wherein alkyl portion has 1 to 8 carbon atoms, aroyl having 7 to 15 carbon atoms (e.g., benzoyl) in which the aryl portion can be substituted by halogen, $C_{1-8}$-alkyl, $C_{1-8}$-alkoxy, nitro, carboxy, hydroxyl, phenoxy, benzyloxy or combinations thereof, wherein said phenyl or pyridyl and/or the fused 5 to 7 membered heterocyclic ring is optionally further substituted by one or more substituents selected from halogen, alkyl having 1 to 4 carbon atoms, alkoxy having 1 to 4 carbon atoms, $NR^1R^2$, nitro, hydroxyl, and cyano, and wherein said 5 to 7 membered heterocyclic ring is optionally fused with another aryl group or heteroaryl group which in each case contains 5 to 10 ring atoms and in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms (e.g., 3 to 8 carbon atoms), cycloalkylalkyl having 4 to 14 carbon atoms (e.g., 4 to 8 carbon atoms), Ar-alkyl wherein alkyl portion has 1 to 8 carbon atoms, Het-alkyl wherein alkyl portion has 1 to 8 carbon atoms, $COR^5$, $COOR^5$, $CONR^5R^6$, halogen, carboxy, cyano, hydroxyl, $NR^1R^2$, nitro, oxo, thio, Ar, Het or combinations thereof, or (c) thienyl, pyrrolyl, dithienyl, pyrazolyl, imidazolyl, oxazolyl, isoxazolyl, triazolyl, thiazolyl, or isothiazolyl, each of which is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms (e.g., 3 to 8 carbon atoms), cycloalkylalkyl having 4 to 14 carbon atoms (e.g., 4 to 8 carbon atoms), Ar-alkyl wherein alkyl portion has 1 to 8 carbon atoms, Het-alkyl wherein alkyl portion has 1 to 8 carbon atoms, $COR^5$, $COOR^5$, $CONR^5R^6$, halogen, carboxy, cyano, hydroxyl, $NR^1R^2$, nitro, oxo, thio, Ar, Het or combinations thereof, wherein said thienyl, pyrrolyl, dithienyl, pyrazolyl, imidazolyl, oxazolyl, isoxazolyl, triazolyl, thiazolyl, or isothiazolyl group is optionally fused with another aryl group or heteroaryl group which in each case contains 5 to 10 ring atoms and in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms (e.g., 3 to 8 carbon atoms), cycloalkylalkyl having 4 to 14 carbon atoms (e.g., 4 to 8 carbon atoms), Ar-alkyl wherein alkyl portion has 1 to 8 carbon atoms, Het-alkyl wherein alkyl portion has 1 to 8 carbon atoms, $COR^5$, $COOR^5$, $CONR^5R^6$, halogen, carboxy, cyano, hydroxyl, $NR^1R^2$, nitro, oxo, thio, Ar, Het or combinations thereof;

$R^1$ and $R^2$ are each independently H, alkyl having 1 to 8 carbon atoms or aryl having 6 to 14 (e.g., 6 to 10) carbon atoms;

$R^3$ and $R^4$ are each independently H, alkyl having 1 to 8 carbon atoms, halogenated alkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, or halogen;

$R^5$ and $R^6$ are each independently H, alkyl having 1 to 8 carbon atoms, halogenated alkyl having 1 to 8 carbon atoms, alkenyl having 2 to 8 carbon atoms, alkynyl having 2 to 8 carbon atoms, cycloalkyl having 3 to 10 carbon atoms (e.g., 3 to 8 carbon atoms), cycloalkylalkyl having 4 to 14 carbon atoms (e.g., 4 to 8 carbon atoms), Ar, Het, Ar-alkyl wherein alkyl portion has 1 to 8 carbon atoms, Het-alkyl wherein alkyl portion has 1 to 8 carbon atoms;

Ar is an aryl group containing 6 to 14 carbon atoms which is unsubstituted or substituted one or more times by alkyl having 1 to 8 C atoms, alkoxy having 1 to 8 C atoms, halogen (F, Cl, Br, or I, preferably F or Cl), dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 10 C atoms and is optionally substituted, aryl having 6 to 10 carbon atoms, aryloxy wherein the aryl portion contains 6 to 14 carbon atoms (e.g., phenyl, naphthyl, biphenyl) and is optionally substituted, arylthio wherein the aryl portion contains 6 to 14 carbon atoms (e.g., phenyl, naphthyl, biphenyl) and is optionally substituted, cycloalkyloxy wherein the cycloalkyl group has 3 to 10 C atoms and is optionally substituted, sulfo, sulfonylamino, acylamido (e.g., acetamido), acyloxy (e.g., acetoxy) or combinations thereof; and Het is a heterocyclic group, which is fully saturated, partially saturated or fully unsaturated, having 5 to 14 ring atoms in which at least 1 ring atom is a N, O or S atom, which is substituted one or more times by halogen (F, Cl, Br, or I, preferably F or Cl), aryl having 6 to 14 carbon atoms (e.g., phenyl, naphthyl, biphenyl) and is optionally substituted, e.g., alkyl having 1 to 8 C atoms, alkoxy having 1 to 8 C atoms, cyano, trifluoromethyl, nitro, oxo, amino, monoalkylamino having 1 to 8 C atoms, dialkylamino wherein each alkyl group has 1 to 8 C atoms, or combinations thereof; and pharmaceutically acceptable salts thereof.

The present invention also includes compounds of Formula I':

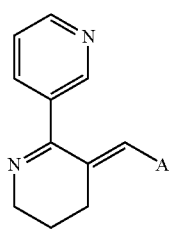

(I')

wherein

A is (a) phenyl or pyridyl, each of which is substituted by a 5 to 7 membered heterocyclic ring containing an O, S, or N ring atom, and optionally containing a further N ring atom, wherein the heterocyclic ring is fully unsaturated, partially saturated or fully saturated and is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het or combinations thereof, wherein said phenyl or pyridyl is optionally further substituted by one or more substituents selected from halogen, alkyl having 1 to 4 carbon atoms, alkoxy having 1 to 4 carbon atoms, $NR^1R^2$, nitro, hydroxyl, and cyano, and wherein said 5 to 7 membered heterocyclic ring is optionally fused with an aryl group or heteroaryl group containing 5 to 10 ring atoms in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het and combinations thereof, (b) phenyl or pyridyl which in each case is fused with a 5 to 7 membered heterocyclic ring containing 1 to 3 hetero atoms each selected from O, S, and N, to form a bicyclic group wherein the fused heterocyclic ring is fully unsaturated, partially saturated or fully saturated, and wherein said bicyclic group is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, alkylthio (e.g., —S—$CH_3$), alkylsulfinyl (e.g., —SO—$CH_3$), alkylsulfonyl (e.g., —$SO_2$—$CH_3$), aryl having 6 to 10 carbon atoms, arylalkyl having 7 to 14 carbon atoms, aroyl having 7 to 15 carbon atoms (e.g., benzoyl) in which the aryl portion can be substituted by halogen, $C_{1-8}$-alkyl, $C_{1-8}$-alkoxy, nitro, carboxy, hydroxyl, phenoxy, benzyloxy or combinations thereof, wherein said phenyl or pyridyl and/or the fused 5 to 7 membered heterocyclic ring is optionally further substituted by one or more substituents selected from halogen, alkyl having 1 to 4 carbon atoms, alkoxy having 1 to 4 carbon atoms, $NR^1R^2$, nitro, hydroxyl, and cyano, and wherein said 5 to 7 membered heterocyclic ring is optionally fused with another aryl group or heteroaryl group containing 5 to 10 ring atoms in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het or combinations thereof, or (c) thienyl, pyrrolyl, dithienyl, pyrazolyl, imidazolyl, oxazolyl, isoxazolyl, triazolyl, thiazolyl, or isothiazolyl, each of which is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het or combinations thereof, wherein said thienyl, pyrrolyl, dithienyl, pyrazolyl, imidazolyl, oxazolyl, isoxazolyl, triazolyl, thiazolyl, or isothiazolyl group is optionally fused with another aryl group or heteroaryl group containing 5 to 10 ring atoms in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het or combinations thereof;

$R^1$ and $R^2$ are each independently H, alkyl having 1 to 8 carbon atoms or aryl having 6 to 10 carbon atoms;

Ar is an aryl group containing 6 to 14 carbon atoms which is unsubstituted or substituted one or more times by alkyl having 1 to 8 C atoms, alkoxy having 1 to 8 C atoms, halogen (F, Cl, Br, or I, preferably F or Cl), dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 10 C atoms and is optionally substituted, aryloxy wherein the aryl portion contains 6 to 14 carbon atoms (e.g., phenyl, naphthyl, biphenyl) and is optionally substituted, arylthio wherein the aryl portion contains 6 to 14 carbon atoms (e.g., phenyl, naphthyl, biphenyl) and is optionally substituted, cycloalkyloxy wherein the cycloalkyl group has 3 to 10 C atoms and is optionally substituted, sulfo, sulfonylamino, acylamido (e.g., acetamido), acyloxy (e.g., acetoxy) or combinations thereof; and Het is a heterocyclic group, which is fully saturated, partially saturated or fully unsaturated, having 5 to 14 ring atoms in which at least 1 ring atom is a N, O or S atom, which is substituted one or more times by halogen (F, Cl, Br, or I, preferably F or Cl), aryl having 6 to 14 carbon atoms (e.g., phenyl, naphthyl, biphenyl) and is optionally substituted, e.g., alkyl having 1 to 8 C atoms, alkoxy having 1 to 8 C atoms, cyano, trifluoromethyl, nitro, oxo, amino, monoalkylamino having 1 to 8 C atoms, dialkylamino wherein each alkyl group has 1 to 8 C atoms, or combinations thereof; and pharmaceutically acceptable salts thereof.

In accordance with a method aspect of the invention, there is provided a method of treating a patient (e.g., a mammal such as a human) suffering from a disease state (e.g., memory impairment) comprising administering to the patient a compound according to Formula I or Formula I'. Preferably, the disease state involves decreased nicotinic acetylcholine receptor activity.

In accordance with a method aspect of the invention there is provided a method for the treatment or prophylaxis of a disease or condition resulting from dysfunction of nicotinic acetylcholine receptor transmission in a mammal, e.g. a human, comprising administering an effective amount of a compound according to Formula I or Formula I'.

In accordance with a method aspect of the invention there is provided a method for the treatment or prophylaxis of a disease or condition resulting from defective or malfunctioning nicotinic acetylcholine receptors, particularly α7nACh receptors, in a mammal, e.g. a human, comprising administering an effective amount of a compound according to Formula I or Formula I'.

In accordance with a method aspect of the invention there is provided a method for the treatment or prophylaxis of a disease or condition resulting from suppressed nicotinic acetylcholine receptor transmission in a mammal, e.g., a human, comprising administering an amount of a compound according to Formula I or Formula I' effective to activate α7nACh receptors.

In accordance with another method aspect of the invention there is provided a method for the treatment or prophylaxis of a psychotic disorder, a cognition impairment (e.g., memory impairment), or neurodegenerative disease in a mammal, e.g., a human, comprising administering an effective amount of a compound according to Formula I or Formula I'.

In accordance with another method aspect of the invention there is provided a method for the treatment or prophylaxis of a disease or condition resulting from loss of cholinergic synapse in a mammal, e.g., a human, comprising administering an effective amount of a compound according to Formula I or Formula I'.

In accordance with another method aspect of the invention there is provided a method for the treatment or prophylaxis of a neurodegenerative disorder by activation of α7nACh receptors in a mammal, e.g., a human, comprising administering an effective amount of a compound according to Formula I or Formula I'.

In accordance with another method aspect of the invention there is provided a method for protecting neurons in a mammal, e.g., a human, from neurotoxicity induced by activation of α7nACh receptors comprising administering an effective amount of a compound according to Formula I or Formula I'.

In accordance with another method aspect of the invention there is provided a method for the treatment or prophylaxis of a neurodegenerative disorder by inhibiting the binding of Aβ peptides to α7nACh receptors in a mammal, e.g., a human, comprising administering an effective amount of a compound according to Formula I or Formula I'.

In accordance with another method aspect of the invention there is provided a method for protecting neurons in a mammal, e.g., a human, from neurotoxicity induced by Aβ peptides comprising administering an effective amount of a compound according to Formula I or Formula I'.

In accordance with another method aspect of the invention there is provided a method for alleviating inhibition of cholinergic function induced by Aβ peptides in a mammal, e.g., a human, from neurotoxicity comprising administering an effective amount of a compound according to Formula I or Formula I'.

The compounds of the present invention are nicotinic alpha-7 ligands, preferably agonists, especially partial agonists, for the alpha-7 nicotinic acetylcholine receptor. Assays for determining nicotinic acetylcholine activity are known within the art. See, e.g., Davies, A. R., et al., *Characterisation of the binding of [3H]methyllycaconitine: a new radioligand for labelling alpha 7-type neuronal nicotinic acetylcholine receptors*. Neuropharmacology. 1999. 38(5): p. 679-90. As agonists for α-7 nAChRs, the compounds are useful in the prophylaxis and treatment of a variety of diseases and conditions associated with the central nervous system. Nicotinic acetylcholine receptors are ligand-gated ion-channel receptors that are composed of five subunit proteins which form a central ion-conducting pore. Presently, there are eleven known neuronal nAChR subunits (α2-α9 and β2-β4). There are also five further subunits expressed in the peripheral nervous system (α1, β1, γ, δ, ε).

The nAChR receptor subtypes can be homopentameric or heteropentameric. The subtype which has received considerable attention is the homopentameric α7 receptor subtype formed from five α7 subunits. The α7nAChRs exhibit a high affinity for nicotine (agonist) and for α-bungarotoxin (antagonist). Studies have shown the α7-nAChR agonists can be useful in the treatment of psychotic diseases, neurodegenerative diseases, and cognitive impairments, among other things. While nicotine is a known agonist, there is a need for the development of other α7-nAChR agonists, especially selective agonists, that are less toxic or exhibit fewer side effects than nicotine.

The compound anabaseine, i.e., 2-(3-pyridyl)-3,4,5,6-tetrahydropyridine is a naturally occurring toxin in certain marine worms (nemertine worms) and ants. See, e.g., Kem et al., Toxicon, 9:23, 1971. Anabaseine is a potent activator of mammalian nicotinic receptors. See, e.g., Kem, Amer. Zoologist, 25, 99, 1985. Certain anabaseine analogs such as anabasine and DMAB (3-[4-(dimethylamino)benzylidene]-3,4,5,6-tetrahydro-2',3'-bipyridine) are also known nicotinic receptor agonists. See, e.g., U.S. Pat. No. 5,602,257 and WO 92/15306. One particular anabaseine analog, (E-3-[2,4-dimethoxy-benzylidene]-anabeseine, also known as GTS-21 and DMXB (see, e.g., U.S. Pat. No. 5,741,802), is a selective partial α7-nAChR agonist that has been studied extensively. For example, abnormal sensory inhibition is a sensory processing deficit in schizophrenics and GTS-21 has been found to increase sensory inhibition through interaction with α7-nAChR s. See, e.g., Stevens et al., Psychopharmacology, 136: 320-27 (1998).

With regards to the compounds of Formula I and Formula I', halogen herein refers to F, Cl, Br, and I. Preferred halogens are F and Cl.

Alkyl throughout means a straight-chain or branched-chain aliphatic hydrocarbon radical having preferably 1 to 8 carbon atoms, especially 1 to 4 carbon atoms. Suitable alkyl groups include methyl, ethyl, propyl, isopropyl, butyl, sec-butyl, tert-butyl, pentyl, hexyl, heptyl, and octyl. Other examples of suitable alkyl groups include 1-, 2- or 3-methyl-butyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Suitable alkenyl or alkynyl groups are 1-propenyl, 2-propenyl (allyl), 1-butenyl, 2-butenyl, 3-butenyl, 1-pentenyl, 2-pentenyl, ethynyl, 1-propynyl, 2-propynyl, 1-butynyl, 1,3-butadienyl and 3-methyl-2-butenyl.

Alkoxy means alkyl-O— groups in which the alkyl portion preferably has 1 to 8, more preferably 1 to 6 carbon atoms, especially 1 to 4 carbon atoms. Suitable alkoxy groups include methoxy, ethoxy, propoxy, isopropoxy, isobutoxy, sec-butoxy, pentoxy, hexoxy, heptoxy, and octoxy. Preferred alkoxy groups are methoxy and ethoxy. Similarly, alkoxycarbonyl means an alkyl-O—CO— group in which the alkyl portion has 1 to 8 carbon atoms.

Cycloalkyl means a monocyclic, bicyclic or tricyclic saturated hydrocarbon radical having 3 to 10 carbon atoms, preferably 3 to 8 carbon atoms, especially 3 to 6 carbon atoms. Suitable cycloalkyl groups include cyclopropyl, cyclobutyl, cyclopentyl, cyclohexyl, cycloheptyl, cyclooctyl, and norbornyl. Other suitable cycloalkyl groups include spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, and bicyclo[4.2.0]octyl. Preferred cycloalkyl groups are cyclopropyl, cyclopentyl, and cyclohexyl.

The cycloalkyl group can be substituted by $C_{1-4}$-alkyl, $C_{1-4}$-alkoxy, hydroxyl, amino, monoalkylamino having 1 to 4 C atoms, and/or dialklyamino in which each alkyl group has 1 to 4 C atoms.

Cycloalkylalkyl groups contain 4 to 14 carbon atoms, for example, cyclopropylmethyl, cyclopropylethyl, cyclobutyl-methyl, cyclopentylmethyl, and cyclohexylmethyl.

Aryl, as a group or substituent per se or as part of a group or substituent, refers to an aromatic carbocyclic radical containing 6 to 14 carbon atoms, preferably 6 to 10 carbon atoms, unless indicated otherwise. Suitable aryl groups include phenyl, napthyl and biphenyl. Substituted aryl groups include the above-described aryl groups which are substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Heterocyclic groups refer to saturated, partially saturated and unsaturated heterocyclic groups having one, two or three rings and a total number of 5 to 14, preferably 5 to 10, ring atoms wherein at least one of the ring atoms is an N, O or S atom. Preferably, the heterocyclic group contains 1 to 3 hetero-ring atoms selected from N, O and S. Suitable saturated and partially saturated heterocyclic groups include, but are not limited to tetrahydrofuranyl, tetrahydrothienyl, pyrrolidinyl, piperidinyl, piperazinyl, morpholinyl, isoxazolinyl and the like. Suitable heteroaryl groups include but are not limited to furyl, thienyl, pyrrolyl, pyrazolyl, imidazolyl, pyridyl, pyrimidinyl, indolyl, quinolinyl, naphthyridinyl and the like. Preferred heterocyclic and heteroaryl groups include terahydrofuranyl, tetrahydropyranyl, 2-thienyl, 3-thienyl, 2-, 3- or 4-pyridyl, 2-, 3-, 4-, 5-, 6-, 7- or 8-quinolinyl, and 1-, 3-, 4-, 5-, 6-, 7- or 8-isoquinolinyl. Other examples of suitable heterocyclic groups, are 2-quinolinyl, 1,3-benzodioxyl, 2-thienyl, 2-benzofuranyl, 2-benzothiofuranyl, 3-thienyl, 2,3-dihydro-5-benzofuranyl, 4-indoyl, 4-pyridyl, 3-qionolinyl, 4-quinolinyl, 1,4-benzodioxan-6-yl, 3-indoyl, 2-pyrrolyl, 3,4-1,2-benzopyran-6-yl, 5-indolyl, 1,5-benzoxepin-8-yl, 3-pyridyl, 6-coumarinyl, 5-benzofuranyl, 2-isoimidazol-4-yl, 3-pyrazolyl, and 3-carbazolyl.

Substituted heterocyclic groups refer to the heterocyclic groups described above which are substituted in one or more places by, for example, halogen, aryl, alkyl, alkoxy, cyano, trifluoromethyl, nitro, oxo, amino, alkylamino, and dialkylamino.

Acyl refers to alkanoyl radicals having 1 to 13 carbon atoms in which the alkyl portion can be substituted by halogen, hydroxy, carboxy, amino, thio, $C_{1-8}$-alkyl, aryl having 6 to 14 C atoms and/or $C_{1-8}$-alkoxy; or aroyl radicals having 7 to 15 carbon atoms in which the aryl portion can be substituted by halogen, $C_{1-8}$-alkyl, $C_{1-8}$-alkoxy, nitro, carboxy and/or hydroxy. Suitable acyl groups include formyl, acetyl, propionyl, butanoyl and benzoyl.

Radicals which are substituted one or more times preferably have 1 to 3 substituents, especially 1 or 2 substituents of the exemplified substituents. Halogenated radicals such as halogenated alkyls include perhalo radicals such as trifluoromethyl.

In the compounds of Formula I or Formula I', A is preferably pyrrolyl, thienyl, benzofuranyl, benzothiophenyl (benzothienyl), pyrazolyl, indazolyl, phenyl or indolyl which in each case is unsubstituted or is substituted by alkyl having 1 to 8 C atoms, alkoxy having 1 to 8 C atoms, halogen, carboxy, oxo, nitro, oxide, alkoxycarbonyl having 2 to 8 C atoms, alkyl-sulfonyl having 1 to 8 C atoms, Ar, Ar—CO—, Ar-sulfonyl, Ar—O—, Ar-alkyl-O— wherein the alkylene group has 1 to 8 C atoms, Ar-thio, Hetero, cyano, trifluoromethyl, halogenated-alkyl having 1 to 8 C atoms, halogenated-alkoxy having 1 to 8 C atoms, amino, monoalkylamino having 1 to 8 C atoms, dialkylamino wherein each alkyl group has 1 to 8 C atoms, hydroxyl, hydroxyalkyl having 1 to 8 C atoms, hydroxyalkoxy having 2 to 8 C atoms, acyl, alkylthio having 1 to 8 C atoms, alkylsulphinyl having 1 to 8 C atoms, acylamido (e.g., acetamido), and acyloxy (e.g., acetoxy).

$R^3$ and $R^4$ are each preferably H.

In addition, in accordance with the invention, preferred compounds are those described by subformulas Ia-Ip, which correspond to Formula I, but exhibit the following preferred groups:

Ia A is dihydrobenzofuranyl, e.g., 2,3-dihydrobenzofuran-5-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, hydroxyalkyl, or combinations thereof.

Ib A is dihydrobenzodioxinyl, e.g., 2,3-dihydrobenzo[1,4]dioxin-6-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, hydroxyalkyl, or combinations thereof.

Ic A is chromanyl, e.g., chroman-6-yl, which is substituted or substituted by alkyl, alkoxy, halogen, carboxy, oxo, nitro, alkoxycarbonyl, cyano, trifluoromethyl, amino, monoalkylamino, dialkylamino, hydroxyl, hydroxyalkyl, or combinations thereof.

Id A is dihydrobenzodioxepinyl, e.g., 3,4-dihydro-2H-benzo[b][1,4]dioxepin-7-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, hydroxyalkyl, or combinations thereof.

Ie A is indolyl, e.g., indol-3-yl, indol-4-yl, indol-5-yl, indol-6-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, hydroxyalkyl, or combinations thereof.

If A is phenyl substituted by a heterocylic group (e.g., 4-(4-morpholinyl)-phenyl, 4-(pyrrolidin-1-yl)-phenyl, 4-(piperidin-1-yl)-phenyl, 3-(piperidin-1-yl)-phenyl, 4-(piperazin-1-yl)-phenyl, 4-(thiomorpholin-4-yl)-phenyl, 4-(1,4-diazepan-1-yl)-phenyl, 4-(1,4-oxazepan-4-yl)-phenyl), which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, hydroxyalkyl, $COR^S$, or combinations thereof.

Ig A is benzoxazinyl, e.g, 3,4-dihydro-2H-benzo[1,4]oxazin-7-yl, which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, or hydroxyalkyl, or combinations thereof.

Ih A is indazolyl, e.g., indazol-3-yl, indazol-4-yl, indazol-5-yl, indazol-6-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, hydroxyalkyl, or combinations thereof.

Ii A is benzoimidazolyl, e.g., benzoimidazol-5-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, hydroxyalkyl, or combinations thereof.

Ij A is phenylpiperazinyl, e.g., 4-phenylpiperazin-1-yl, which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, hydroxyalkyl, Ar or combinations thereof.

Ik A is benzothiazolyl (e.g., benzothiazol-5-yl, benzothiazol-6-yl) which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, hydroxyalkyl, or combinations thereof.

Il A is pyrrolyl (e.g., 1H-pyrrol-2-yl) which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, hydroxyalkyl, aryl (e.g. phenyl) which is unsubstituted or substituted by halogen, halogenated alkyl, or halogenated alkoxy, or arylalkyl (benzyl, biphenylmethyl) which is unsubstituted or substituted by halogen, halogenated alkyl, or halogenated alkoxy, or combinations thereof.

Im A is pyrazolyl (e.g., 2H-pyrazol-3-yl) which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, hydroxyalkyl, Ar (e.g. phenyl) which is unsubstituted or substituted by halogen, halogenated alkyl, or halogenated alkoxy, or arylalkyl (benzyl, biphenylmethyl) which is unsubstituted or substituted by halogen, halogenated alkyl, or halogenated alkoxy, or combinations thereof.

In A is diazabicycloheptyl (e.g., 2,5-diazabicyclo[2.2.1]hept-2-yl) which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, hydroxyalkyl, or combinations thereof.

Io A is benzodioxolyl (e.g., benzo[1,3]dioxol-5-yl) which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, hydroxyalkyl, or combinations thereof.

Ip A is dihydrobenzodioinyl (e.g., 2,3-dihydrobenzo[1,4]dioin-6-yl) which is unsubstituted or substituted by alkyl, alkoxy, cycloalkyl, cycloalkylalkyl, halogen, carboxy, oxo, nitro, alkoxycarbonyl, cyano, trifluoromethyl, amino, monoalkylamino, dialkylamino, hydroxyl, or hydroxyalkyl, or combinations thereof.

According to a further preferred compound aspect of the invention, the compound of formula I is selected from:

3-Quinolin-2-ylmethylene-3,4,5,6-terahydro[2,3']bipyridinyl;

3-Quinolin-3-ylmethylene-3,4,5,6-terahydro[2,3']bipyridinyl;

3-(3,4-Dihydroquinolin-4-ylmethylene)-3,4,5,6-terahydro[2,3']bipyridinyl;

3-[1-(Toluene-4-sulfonyl-1H-indol-4-ylmethylene]-3,4,5,6-tetrahydro[2,3']bipyridinyl;

3-(1H-Indol-3-ylmethylene)-3,4,5,6-tetrahydro[2,3']bipyridinyl;

3-(1H-Indol-4-ylmethylene)-3,4,5,6-tetrahydro[2,3']bipyridinyl;

3-(1H-Pyrrol-2-ylmethylene)-3,4,5,6-tetrahydro[2,3']bipyridinyl;

3-(5,6-Dihydro-4H-[2,3']bipyridinyl-3-ylidenemethyl-1H-indole-6-carboxylic acid Methyl Ester;

3-(5-Methoxy-1H-indol-3-ylmethylene)-3,4,5,6-tetrahydro[2,3']bipyridinyl;

3-(1H-Indol-5-ylmethylene)-3,4,5,6-tetrahydro[2,3']bipyridinyl;

3-(6-Benzyloxy-2H-pyrrolo[3,3-c]pyridin-1-ylmethylene)-3,4,5,6-tetrahydro[2,3']bipyridinyl;

3-(1-Methyl-1H-indol-2-ylmethylene)-3,4,5,6-tetrahydro[2,3']bipyridinyl;

3-(1-Methyl-1H-indol-3-ylmethylene)-3,4,5,6-tetrahydro[2,3']bipyridinyl;
3-(4-Benzyloxy-1H-indol-3-ylmethylene)-3,4,5,6-tetrahydro[2,3']bipyridinyl;
3-(2-Methyl-1H-indol-3-ylmethylene)-3,4,5,6-tetrahydro[2,3']bipyridinyl;
3-(3H-Imidazol-4-ylmethylene)-3,4,5,6-tetrahydro[2,3']bipyridinyl;
3-(1-Methyl-1H-pyrrol-3-ylmethylene)-3,4,5,6-tetrahydro[2,3']bipyridinyl;
3-(5-Fluoro-1H-indol-3-ylmethylene)-3,4,5,6-tetrahydro[2,3']bipyridinyl;
3-(6-Methyl-1H-indol-3-ylmethylene)-3,4,5,6-tetrahydro[2,3']bipyridinyl;
3-(7-Methyl-1H-indol-3-ylmethylene)-3,4,5,6-tetrahydro[2,3']bipyridinyl;
3-(5-Benzyloxy-1H-indol-3-ylmethylene)-3,4,5,6-tetrahydro[2,3']bipyridinyl;
3-(2-Methyl-5-nitro-1H-indol-3-ylmethylene)-3,4,5,6-tetrahydro[2,3']bipyridinyl;
[5-(5,6-Dihydro-4H-[2,3']bipyridinyl-3-ylidenemethyl)benzofuran-2-yl]phenylmethanone;
6-(5,6-Dihydro-4H-[2,3']bipyridinyl-3-ylidenemethyl)chromen-2-one;
3-(5'-Bromo-1H,1'H-[2,2']bipyrrolyl-5-ylmethylene)-3,4,5,6-tetrahydro[2,3']bipyridinyl Dihydrochloride;
5-(5,6-Dihydro-4H-[2,3']bipyridinyl-3-ylidenemethyl)-1H-thiophene-2-carboxylic acid Dihydrochloride;
3-(2,3-Dihydrobenzo[1,4]dioxin-6-ylmethylene)-3,4,5,6-tetrahydro[2,3']bipyridinyl Dihydrochloride;
3-[5-(4-Bromophenyl)-thiophen-2-ylmethylene]-3,4,5,6-tetrahydro-[2,3']bipyridinyl Dihydrochloride;
3-[1-(Toluene-4-sulfonyl-1H-indol-3-ylmethylene]-3,4,5,6-tetrahydro[2,3']bipyridinyl Dihydrochloride;
3-[1-Methanesulfonyl-1H-indol-3-ylmethylene]-3,4,5,6-tetrahydro[2,3']bipyridinyl Dihydrochloride;
3-(Thiophen-2-ylmethylene)-3,4,5,6-tetrahydro[2,3']bipyridinyl Dihydrochloride;
3-(Benzofuran-2-ylmethylene)-3,4,5,6-tetrahydro[2,3']bipyridinyl Dihydrochloride;
3-(5-Propylthiophen-2-ylmethylene)-3,4,5,6-tetrahydro[2,3']bipyridinyl Dihydrochloride;
3-(5-Bromothiophen-2-ylmethylene)-3,4,5,6-tetrahydro[2,3']bipyridinyl Dihydrochloride;
3-(5-Methylthiophen-2-ylmethylene)-3,4,5,6-tetrahydro[2,3']bipyridinyl Dihydrochloride;
3-(4-Bromothiophen-2-ylmethylene)-3,4,5,6-tetrahydro[2,3']bipyridinyl Dihydrochloride;
4-[5-(5,6-Dihydro-4H-[2,3']bipyridinyl-3-ylidenemethyl)thiophen-2-yl]phenol Dihydrobromide;
3-(Benzo[b]thiophen-2-ylmethylene)-3,4,5,6-tetrahydro[2,3']bipyridinyl Dihydrochloride;
3-(Thiophen-3-ylmethylene)-3,4,5,6-tetrahydro[2,3']bipyridinyl Dihydrochloride;
3-(Benzo[b]thiophen-3-ylmethylene)-3,4,5,6-tetrahydro[2,3']bipyridinyl Dihydrochloride;
3-(2,3-Dihydrobenzofuran-5-ylmethylene)-3,4,5,6-tetrahydro[2,3']bipyridinyl Dihydrochloride;
3-(3,4-Dihydro-2H-benzo[b][1,4]dioxepin-7-ylmethylene)-3,4,5,6-tetrahydro-[2,3']bipyridinyl Dihydrochloride;
3-(2,2-Dimethylchroman-6-ylmethylene)-3,4,5,6-tetrahydro[2,3']bipyridinyl Dihydrochloride;
3-(2,2-Difluorobenzo[1,3]dioxol-5-ylmethylene)-3,4,5,6-tetrahydro[2,3']bipyridinyl Dihydrochloride;
3-(7-Methoxybenzo[1,3]dioxol-5-ylmethylene)-3,4,5,6-tetrahydro[2,3']bipyridinyl Dihydrochloride;
3-(Benzo[1,3]dioxol-5-ylmethylene)-3,4,5,6-tetrahydro[2,3']bipyridinyl;
3-(5-Bromo-1H-indol-3-ylmethylene)-3,4,5,6-tetrahydro[2,3']bipyridinyl;
4-(5,6-Dihydro-4H-[2,3']bipyridinyl-3-ylidenemethyl)-2-nitrophenol;
3-(1-Methyl-1H-pyrrol-2-ylmethylene)-3,4,5,6-tetrahydro[2,3']bipyridinyl;
3-(5,6-Dihydro-4H-[2,3']bipyridinyl-3-ylidenemethyl)cinnoline;
3-(3-Nitro-4-piperidin-1-ylbenzylidene)-3,4,5,6-tetrahydro[2,3']bipyridinyl;
3-(4-(Pyrazol-1-yl)benzylidene)-3,4,5,6-tetrahydro[2,3']bipyridinyl;
7-(5,6-Dihydro-4H-[2,3']bipyridinyl-3-ylidenemethyl)-4H-benzo[1,4]oxazin-3-one;
6-(5,6-Dihydro-4H-[2,3']bipyridinyl-3-ylidenemethyl)-4H-benzo[1,4]oxazin-3-one;
3-(3-Morpholin-4-ylbenzylidene)-3,4,5,6-tetrahydro[2,3']bipyridinyl;
3-(3-Pyrrolidin-1-ylbenzylidene)-3,4,5,6-tetrahydro[2,3']bipyridinyl;
3-[3-(4-Methylpiperazin-1-yl)benzylidene]-3,4,5,6-tetrahydro[2,3']bipyridinyl;
3-(Benzo[1,3]dioxol-4-ylmethylene)-3,4,5,6-tetrahydro[2,3']bipyridinyl Dihydrochloride,
3-(4-Pyrrolidin-1-yl-benzylidene)-3,4,5,6-tetrahydro[2,3']bipyridinyl,
3-[2-(4-Methylpiperazin-1-yl)benzylidene]-3,4,5,6-tetrahydro[2,3']bipyridinyl,
3-(1H-Indazol-6-ylmethylene)-3,4,5,6-tetrahydro[2,3']bipyridinyl,
3-(1H-Indazol-5-ylmethylene)-3,4,5,6-tetrahydro[2,3']bipyridinyl,
3-(2-Morpholin-4-ylbenzylidene)-3,4,5,6-tetrahydro[2,3']bipyridinyl,
3-(1H-Benztriazol-5-ylmethylene)-3,4,5,6-tetrahydro[2,3']bipyridinyl,
5-(5,6-Dihydro-4H-[2,3']bipyridinyl-3-ylidenemethyl)-1,3-dihydrobenzimidazol-2-one,
3-(1H-Benzimidazol-5-ylmethylene)-3,4,5,6-tetrahydro[2,3']bipyridinyl,
3-(4-Morpholin-4-yl-benzylidene)-3,4,5,6-tetrahydro[2,3']bipyridinyl,
3-[4-(4-Methylpiperazin-1-yl)benzylidene]-3,4,5,6-tetrahydro[2,3']bipyridinyl,
3-(5,6-Dihydro-4H-[2,3']bipyridinyl-3-ylidenemethyl)-10-methyl-10H-phenothiazine,
7-(5,6-Dihydro-4H-[2,3']bipyridinyl-3-ylidenemethyl)-4-methyl-3,4-dihydro-2H-benzo[1,4]oxazine,
3-(1H-Pyrrolo[2,3-b]pyridin-3-ylmethylene)-3,4,5,6-tetrahydro[2,3']bipyridinyl,
3-(6-Methoxy-1H-indol-3-ylmethylene)-3,4,5,6-tetrahydro[2,3']bipyridinyl,
3-(5,6-Dihydro-4H-[2,3']-bipyridinyl-3-ylidenemethyl)-9-methyl-9H-carbazole,
3-(4-Methoxy-1H-indol-3-ylmethylene)-3,4,5,6-tetrahydro[2,3']bipyridinyl,
3-(7-Methoxy-1H-indol-3-ylmethylene)-3,4,5,6-tetrahydro[2,3']bipyridinyl,
3-(6-Fluoro-1H-indol-3-ylmethylene)-3,4,5,6-tetrahydro[2,3']bipyridinyl,
3-(1H-indol-3-ylmethylene)-3,4,5,6-tetrahydro[2,3']bipyridinyl dihydrochloride,
3-(1H-indol-6-ylmethylene)-3,4,5,6-tetrahydro[2,3']bipyridinyl, 3-(5,6-Dihydro-4H-[2,3']bipyridinyl-3-ylidenemethyl)-9-ethyl-9H-carbazole dihydrochloride,
3-(1-Benzyl-1H-indol-3-ylmethylene)-3,4,5,6-tetrahydro[2,3']bipyridinyl,
3-(5,6-Dihydro-4H-[2,3']bipyridinyl-3-ylidenemethyl)-9-ethyl-9H-carbazole,
3-(5-Nitro-1H-indol-3-ylmethylene)-3,4,5,6-tetrahydro[2,3']bipyridinyl,
3-(5-Chloro-1H-indol-3-ylmethylene)-3,4,5,6-tetrahydro-[2,3']bipyridinyl,
3-(3-Nitro-4-pyrrolidin-1-ylbenzylidene)-3,4,5,6-tetrahydro[2,3']bipyridinyl;
3-(3-Amino-4-pyrrolidin-1-ylbenzylidene)-3,4,5,6-tetrahydro[2,3']bipyridinyl;
3-(3-Amino-4-piperidin-1-ylbenzylidene)-3,4,5,6-tetrahydro[2,3']bipyridinyl;
3-(3-Amino-4-morpholin-4-ylbenzylidene)-3,4,5,6-tetrahydro[2,3']bipyridinyl;
3-(5-Chloro-1H-indol-3-ylmethylene)-3,4,5,6-tetrahydro[2,3']bipyridinyl dihydrochloride;
3-(1H-Indazol-4-ylmethylene)-3,4,5,6-tetrahydro[2,3']bipyridinyl;
3-(3-Piperidin-1-ylbenzylidene)-3,4,5,6-tetrahydro[2,3']bipyridinyl;
3-(Benzothiazol-5-ylmethylene)-3,4,5,6-tetrahydro[2,3']bipyridinyl;
3-(3,4-Dihydro-2H-benzo[1,4]oxazin-7-ylmethylene)-3,4,5,6-tetrahydro[2,3']bipyridinyl;
3-(3,4-Dihydro-2H-benzo[1,4]oxazin-7-ylmethylene)-3,4,5,6-tetrahydro[2,3']bipyridinyl trihydrochloride;
3-(4-Cyclopropylmethyl-3,4-dihydro-2H-benzo[1,4]oxazin-7-ylmethylene)-3,4,5,6-tetrahydro[2,3']bipyridinyl;
3-(4-Ethyl-3,4-dihydro-2H-benzo[1,4]oxazin-7-ylmethylene)-3,4,5,6-tetrahydro[2,3']bipyridinyl;
3-(Benzothiazol-6-ylmethylene)-3,4,5,6-tetrahydro[2,3']bipyridinyl;
3-(1-Phenyl-1H-pyrrol-2-ylmethylene)-3,4,5,6-tetrahydro[2,3']bipyridinyl;
3-[2-(5,6-Dihydro-4H-[2,3']bipyridinyl-3-ylidenemethyl)pyrrol-1-yl]benzonitrile;
3-(2-Cyclohexylmethyl-2H-pyrazol-3-ylmethylene)-3,4,5,6-tetrahydro[2,3']bipyridinyl;
3-(2-Cyclopentyl-2H-pyrazol-3-ylmethylene)-3,4,5,6-tetrahydro[2,3']bipyridinyl;
3-[1-(4-Chlorophenyl)-1H-pyrrol-2-ylmethylene]-3,4,5,6-tetrahydro[2,3']bipyridinyl;
3-[1-(4-Trifluoromethoxyphenyl)-1H-pyrrol-2-ylmethylene]-3,4,5,6-tetrahydro[2,3']bipyridinyl;
3-[4-(trans-2,5-Dimethylpiperazin-1-yl)benzylidene]-3,4,5,6-tetrahydro[2,3']bipyridinyl;
[3-[4-(cis-3,5-Dimethylpiperazin-1-yl)benzylidene]-3,4,5,6-tetrahydro[2,3']bipyridinyl;
3-(4-Thiomorpholin-4-yl-benzylidene)-3,4,5,6-tetrahydro[2,3']bipyridinyl;
3-[4-(1-Oxo-1λ4-thiomorpholin-4-yl)-benzylidene]-3,4,5,6-tetrahydro-[2,3']bipyridinyl;
3-[4-(1,1-Dioxo-1λ6-thiomorpholin-4-yl)-benzylidene]-3,4,5,6-tetrahydro-[2,3']bipyridinyl;
3-[4-(2,6-Dimethylmorpholin-4-yl)benzylidene]-3,4,5,6-tetrahydro[2,3']bipyridinyl;
3-(4-[1,4]Diazepan-1-ylbenzylidene)-3,4,5,6-tetrahydro[2,3']bipyridinyl;
3-(4-piperazin-1-ylbenzylidene)-3,4,5,6-tetrahydro[2,3']bipyridinyl;
3-[3-(trans-2,5-Dimethylpiperazin-1-yl)benzylidene]-3,4,5,6-tetrahydro[2,3']bipyridinyl;
3-[3-(cis-3,5-Dimethylpiperazin-1-yl)benzylidene]-3,4,5,6-tetrahydro[2,3']bipyridinyl;
3-(3-Thiomorpholin-4-yl-benzylidene)-3,4,5,6-tetrahydro[2,3']bipyridinyl;
3-[3-(2,6-Dimethylmorpholin-4-yl)benzylidene]-3,4,5,6-tetrahydro[2,3']bipyridinyl;
3-(3-[1,4]Diazepan-1-ylbenzylidene)-3,4,5,6-tetrahydro[2,3']bipyridinyl;
3-[3-(4-Phenylpiperazin-1-yl)benzylidene]-3,4,5,6-tetrahydro[2,3']bipyridinyl;
3-{3-[4-(4-Fluorophenyl)piperazin-1-yl]benzylidene}-3,4,5,6-tetrahydro[2,3']bipyridinyl;
3-(3-Piperazin-1-ylbenzylidene)-3,4,5,6-tetrahydro[2,3']bipyridinyl;
3-{3-[(1S,4S)-2,5-Diazabicyclo[2.2.1]hept-2-yl]benzylidene}-3,4,5,6-tetrahydro[2,3']bipyridinyl;
3-(3-[1,4]Oxazepan-4-ylbenzylidene)-3,4,5,6-tetrahydro[2,3']bipyridinyl;
3-[4-(4-Phenylpiperazin-1-yl)benzylidene]-3,4,5,6-tetrahydro[2,3']bipyridinyl; 3-{4-[4-(4-Fluorophenyl)piperazin-1-yl]benzylidene}-3,4,5,6-tetrahydro[2,3']bipyridinyl;
3-{4-[(1S,4S)-2,5-Diazabicyclo[2.2.1]hept-2-yl]benzylidene}-3,4,5,6-tetrahydro[2,3']bipyridinyl;
3-(4-[1,4]Oxazepan-4-ylbenzylidene)-3,4,5,6-tetrahydro[2,3']bipyridinyl;
3-[4-(3-Methylpiperazin-1-yl)benzylidene]-3,4,5,6-tetrahydro[2,3']bipyridinyl;
3-[4-(2-Methylpiperazin-1-yl)benzylidene]-3,4,5,6-tetrahydro[2,3']bipyridinyl;
3-[3-(4-Ethylpiperazin-1-yl)benzylidene]-3,4,5,6-tetrahydro[2,3']bipyridinyl;
3-[4-(4-Ethylpiperazin-1-yl)benzylidene]-3,4,5,6-tetrahydro[2,3']bipyridinyl;
3-[1-(4-Chlorobenzyl)-1H-pyrrol-2-ylmethylene]-3,4,5,6-tetrahydro[2,3']bipyridinyl;
3-[1-(4-Fluorobenzyl)-1H-pyrrol-2-ylmethylene]-3,4,5,6-tetrahydro[2,3']bipyridinyl;
3-[1-(4-Trifluoromethylbenzyl)-1H-pyrrol-2-ylmethylene]-3,4,5,6-tetrahydro[2,3']bipyridinyl;
3-[1-(4-Chlorobenzyl)-1H-pyrazol-3-ylmethylene]-3,4,5,6-tetrahydro[2,3']bipyridinyl;
3-[1-(4-Fluorobenzyl)-1H-pyrazol-3-ylmethylene]-3,4,5,6-tetrahydro[2,3']bipyridinyl;
3-[1-(2,6-Dichlorobenzyl)-1H-pyrrol-2-ylmethylene]-3,4,5,6-tetrahydro[2,3']bipyridinyl;
3-[1-(3,4-Dichlorobenzyl)-1H-pyrrol-2-ylmethylene]-3,4,5,6-tetrahydro[2,3']bipyridinyl;
3-[1-(4-Trifluoromethoxybenzyl)-1H-pyrrol-2-ylmethylene]-3,4,5,6-tetrahydro[2,3']bipyridinyl;
3-(1-Biphenyl-4-ylmethyl-1H-pyrrol-2-ylmethylene)-3,4,5,6-tetrahydro[2,3']bipyridinyl;
3-[1-(2-Fluorobenzyl)-1H-pyrrol-2-ylmethylene]-3,4,5,6-tetrahydro[2,3']bipyridinyl;
3-(1-Methylpropyl-1H-pyrrol-2-ylmethylene)-3,4,5,6-tetrahydro[2,3']bipyridinyl;
3-(1-Pyridin-4-ylmethyl-1H-pyrrol-2-ylmethylene)-3,4,5,6-tetrahydro[2,3']bipyridinyl;
3-[1-(1-Ethylpropyl)-1H-pyrrol-2-ylmethylene]-3,4,5,6-tetrahydro[2,3']bipyridinyl;
3-[1-(2-Chloro-6-fluorobenzyl)-1H-pyrrol-2-ylmethylene]-3,4,5,6-tetrahydro[2,3']bipyridinyl;
3-(1-Pentafluorophenylmethyl-1H-pyrrol-2-ylmethylene)-3,4,5,6-tetrahydro[2,3']bipyridinyl;
3-[1-(2,4,5-Trifluorobenzyl)-1H-pyrrol-2-ylmethylene]-3,4,5,6-tetrahydro[2,3']bipyridinyl;
3-(1-Ethyl-1H-pyrazol-3-ylmethylene)-3,4,5,6-tetrahydro[2,3']bipyridinyl;

3-[1-(2-Methylpropyl)-1H-pyrazol-3-ylmethylene]-3,4,5,6-tetrahydro[2,3']bipyridinyl;
3-(1-Cyclopropylmethyl-1H-pyrazol-3-ylmethylene)-3,4,5,6-tetrahydro[2,3']bipyridinyl;
3-(1-Cyclobutylmethyl-1H-pyrazol-3-ylmethylene)-3,4,5,6-tetrahydro-[2,3']bipyridinyl;
3-(1-Cyclohexylmethyl-1H-pyrazol-3-ylmethylene)-3,4,5,6-tetrahydro[2,3']bipyridinyl;
3-(1-Cyclopentyl-1H-pyrazol-3-ylmethylene)-3,4,5,6-tetrahydro[2,3']bipyridinyl;
3-[5-Bromo-2-(4-chlorobenzyl)-2H-pyrazol-3-ylmethylene]-3,4,5,6-tetrahydro[2,3']bipyridinyl;
3-[4-(4-Cyclopropylmethylpiperazin-1-yl)benzylidene]-3,4,5,6-tetrahydro[2,3']bipyridinyl;
3-[4-(4-Cyclopentylpiperazin-1-yl)benzylidene]-3,4,5,6-tetrahydro[2,3']bipyridinyl;
3-{4-[(1S,4S)-5-Methyl-2,5-Diazabicyclo[2.2.1]hept-2-yl]benzylidene}-3,4,5,6-tetrahydro[2,3']bipyridinyl;
3-{4-[(1S,4S)-5-Ethyl-2,5-Diazabicyclo[2.2.1]hept-2-yl]benzylidene}-3,4,5,6-tetrahydro[2,3']bipyridinyl;
3-{4-[(1S,4S)-5-Cyclopropylmethyl-2,5-Diazabicyclo[2.2.1]hept-2-yl]benzylidene}-3,4,5,6-tetrahydro[2,3']bipyridinyl;
3-[4-(4-Methyl[1,4]diazepan-1-yl)benzylidene]-3,4,5,6-tetrahydro[2,3']bipyridinyl;
3-[4-(4-Cyclopropylmethyl[1,4]diazepan-1-yl)benzylidene]-3,4,5,6-tetrahydro[2,3']bipyridinyl;
3-[4-(4-Cyclopentyl[1,4]diazepan-1-yl)-benzylidene]-3,4,5,6-tetrahydro[2,3']bipyridinyl
3-[4-(4-Isobutyl-[1,4]diazepan-1-yl)-benzylidene]-3,4,5,6-tetrahydro-[2,3']bipyridinyl;
3-{4-[(1S,4S)-5-(2-Methylpropyl)-2,5-diazabicyclo[2.2.1]hept-2-yl]benzylidene}-3,4,5,6-tetrahydro[2,3']bipyridinyl;
3-{4-[(1S,4S)-5-Cyclopentyl-2,5-diazabicyclo[2.2.1]hept-2-yl]benzylidene}-3,4,5,6-tetrahydro[2,3']bipyridinyl;
3-[4-(4-Ethyl[1,4]diazepan-1-yl)benzylidene]-3,4,5,6-tetrahydro[2,3']bipyridinyl;
Cyclopropyl-{4-[4-(5,6-dihydro-4H-[2,3']bipyridinyl-3-ylidenemethyl)phenyl]piperazin-1-yl}methanone;
1-{4-[4-(5,6-Dihydro-4H-[2,3']bipyridinyl-3-ylidenemethyl)phenyl]piperazin-1-yl}propan-1-one;
1-{4-[4-(5,6-Dihydro-4H-[2,3']bipyridinyl-3-ylidenemethyl)phenyl]piperazin-1-yl}-2,2,2-trifluoroethanone;
Cyclopropyl-{(1S,4S)-5-[4-(5,6-dihydro-4H-[2,3']bipyridinyl-3-ylidenemethyl)phenyl]-2,5-diazabicyclo[2.2.1]hept-2-yl}methanone;
Cyclopropyl-{4-[4-(5,6-dihydro-4H-[2,3']bipyridinyl-3-ylidenemethyl)phenyl][1,4]diazepan-1-yl}methanone;
1-{(1S,4S)-5-[4-(5,6-Dihydro-4H-[2,3']bipyridinyl-3-ylidenemethyl)phenyl]-2,5-diazabicyclo[2.2.1]hept-2-yl}-2,2,2-trifluoroethanone;
1-{(1S,4S)-5-[4-(5,6-Dihydro-4H-[2,3']bipyridinyl-3-ylidenemethyl)phenyl]-2,5-diazabicyclo[2.2.1]hept-2-yl}propan-1-one;
1-{4-[4-(5,6-Dihydro-4H-[2,3']bipyridinyl-3-ylidenemethyl)phenyl][1,4]diazepan-1-yl}-2,2,2-trifluoroethanone;
1-{4-[4-(5,6-Dihydro-4H-[2,3']bipyridinyl-3-ylidenemethyl)phenyl][1,4]diazepan-1-yl}propan-1-one;
Cyclopropyl-{(1S,4S)-5-[3-(5,6-dihydro-4H-[2,3']bipyridinyl-3-ylidenemethyl)phenyl]-2,5-diazabicyclo[2.2.1]hept-2-yl}methanone;
1-{(1S,4S)-5-[3-(5,6-Dihydro-4H-[2,3']bipyridinyl-3-ylidenemethyl)phenyl]-2,5-diazabicyclo[2.2.1]hept-2-yl}-2,2,2-trifluoroethanone;
Cyclopropyl-{4-[3-(5,6-dihydro-4H-[2,3']bipyridinyl-3-ylidenemethyl)phenyl]-[1,4]diazepan-1-yl}methanone;
1-{4-[3-(5,6-Dihydro-4H-[2,3']bipyridinyl-3-ylidenemethyl)phenyl][1,4]diazepan-1-yl}-2,2,2-trifluoroethanone;
1-{4-[3-(5,6-Dihydro-4H-[2,3']bipyridinyl-3-ylidenemethyl)phenyl]-[1,4]diazepan-1-yl}propan-1-one;
3-(Benzo[1,3]dioxol-5-ylmethylene)-5'-methyl-3,4,5,6-tetrahydro[2,3']bipyridinyl;
3-(1H-Indol-3-ylmethylene)-5'-methyl-3,4,5,6-tetrahydro[2,3']bipyridinyl;
5'-Methyl-3-(1H-pyrrol-2-ylmethylene)-3,4,5,6-tetrahydro[2,3']bipyridinyl;
3-(Benzo[1,3]dioxol-5-ylmethylene)-5'-fluoro-3,4,5,6-tetrahydro[2,3']bipyridinyl;
5'-Fluoro-3-(1H-indol-3-ylmethylene)-3,4,5,6-tetrahydro[2,3']bipyridinyl;
5'-Fluoro-3-(1H-pyrrol-2-ylmethylene)-3,4,5,6-tetrahydro[2,3']bipyridinyl;
3-(2,3-Dihydrobenzo[1,4]dioxin-6-ylmethylene)-5'-fluoro-3,4,5,6-tetrahydro[2,3']bipyridinyl;
3-(1-Cyclopropylmethyl-1H-pyrrol-2-ylmethylene)-5'-fluoro-3,4,5,6-tetrahydro[2,3']bipyridinyl;
5'-Fluoro-3-(4-morpholin-4-ylbenzylidene)-3,4,5,6-tetrahydro[2,3']bipyridinyl;
3-(1H-Indol-3-ylmethylene)-6'-trifluoromethyl-3,4,5,6-tetrahydro[2,3'];
and
physiologically acceptable salts thereof.

Accordingly to a preferred method of use aspect of the invention, the compound of Formula I is selected from:
3-Quinolin-2-ylmethylene-3,4,5,6-terahydro[2,3']bipyridinyl;
3-Quinolin-3-ylmethylene-3,4,5,6-terahydro[2,3']bipyridinyl;
3-(3,4-Dihydroquinolin-4-ylmethylene)-3,4,5,6-terahydro[2,3']bipyridinyl;
3-[1-(Toluene-4-sulfonyl-1H-indol-4-ylmethylene]-3,4,5,6-tetrahydro[2,3']bipyridinyl;
3-(1H-Indol-3-ylmethylene)-3,4,5,6-tetrahydro[2,3']bipyridinyl;
3-(1H-Indol-4-ylmethylene)-3,4,5,6-tetrahydro[2,3']bipyridinyl;
3-(1H-Pyrrol-2-ylmethylene)-3,4,5,6-tetrahydro[2,3']bipyridinyl;
3-(5,6-Dihydro-4H-[2,3']bipyridinyl-3-ylidenemethyl-1H-indole-6-carboxylic acid Methyl Ester;
3-(5-Methoxy-1H-indol-3-ylmethylene)-3,4,5,6-tetrahydro[2,3']bipyridinyl;
3-(1H-Indol-5-ylmethylene)-3,4,5,6-tetrahydro[2,3']bipyridinyl;
3-(6-Benzyloxy-2H-pyrrolo[3,3-c]pyridin-1-ylmethylene)-3,4,5,6-tetrahydro[2,3']bipyridinyl;
3-(1-Methyl-1H-indol-2-ylmethylene)-3,4,5,6-tetrahydro[2,3']bipyridinyl;
3-(1-Methyl-1H-indol-3-ylmethylene)-3,4,5,6-tetrahydro[2,3']bipyridinyl;
3-(4-Benzyloxy-1H-indol-3-ylmethylene)-3,4,5,6-tetrahydro[2,3']bipyridinyl;
3-(2-Methyl-1H-indol-3-ylmethylene)-3,4,5,6-tetrahydro[2,3']bipyridinyl;
3-(3H-Imidazol-4-ylmethylene)-3,4,5,6-tetrahydro[2,3']bipyridinyl;
3-(1-Methyl-1H-pyrrol-3-ylmethylene)-3,4,5,6-tetrahydro[2,3']bipyridinyl;
3-(5-Fluoro-1H-indol-3-ylmethylene)-3,4,5,6-tetrahydro[2,3']bipyridinyl;

3-(6-Methyl-1H-indol-3-ylmethylene)-3,4,5,6-tetrahydro[2,3']bipyridinyl;

3-(7-Methyl-1H-indol-3-ylmethylene)-3,4,5,6-tetrahydro[2,3']bipyridinyl;

3-(5-Benzyloxy-1H-indol-3-ylmethylene)-3,4,5,6-tetrahydro[2,3']bipyridinyl;

3-(2-Methyl-5-nitro-1H-indol-3-ylmethylene)-3,4,5,6-tetrahydro[2,3']bipyridinyl;

[5-(5,6-Dihydro-4H-[2,3']bipyridinyl-3-ylidenemethyl)benzofuran-2-yl]phenylmethanone;

6-(5,6-Dihydro-4H-[2,3']bipyridinyl-3-ylidenemethyl)chromen-2-one;

3-(5'-Bromo-1H,1'H-[2,2']bipyrrolyl-5-ylmethylene)-3,4,5,6-tetrahydro[2,3']bipyridinyl Dihydrochloride;

5-(5,6-Dihydro-4H-[2,3']bipyridinyl-3-ylidenemethyl)-1H-thiophene-2-carboxylic acid Dihydrochloride;

3-(2,3-Dihydrobenzo[1,4]dioxin-6-ylmethylene)-3,4,5,6-tetrahydro[2,3']bipyridinyl Dihydrochloride;

3-[5-(4-Bromophenyl)-thiophen-2-ylmethylene]-3,4,5,6-tetrahydro-[2,3']bipyridinyl Dihydrochloride;

3-[1-(Toluene-4-sulfonyl-1H-indol-3-ylmethylene]-3,4,5,6-tetrahydro[2,3']bipyridinyl Dihydrochloride;

3-[1-Methanesulfonyl-1H-indol-3-ylmethylene]-3,4,5,6-tetrahydro[2,3']bipyridinyl Dihydrochloride;

3-(Thiophen-2-ylmethylene)-3,4,5,6-tetrahydro[2,3']bipyridinyl Dihydrochloride;

3-(Benzofuran-2-ylmethylene)-3,4,5,6-tetrahydro[2,3']bipyridinyl Dihydrochloride;

3-(5-Propylthiophen-2-ylmethylene)-3,4,5,6-tetrahydro[2,3']bipyridinyl Dihydrochloride;

3-(5-Bromothiophen-2-ylmethylene)-3,4,5,6-tetrahydro[2,3']bipyridinyl Dihydrochloride;

3-(5-Methylthiophen-2-ylmethylene)-3,4,5,6-tetrahydro[2,3']bipyridinyl Dihydrochloride;

3-(4-Bromothiophen-2-ylmethylene)-3,4,5,6-tetrahydro[2,3']bipyridinyl Dihydrochloride;

4-[5-(5,6-Dihydro-4H-[2,3']bipyridinyl-3-ylidenemethyl)thiophen-2-yl]phenol Dihydrobromide;

3-(Benzo[b]thiophen-2-ylmethylene)-3,4,5,6-tetrahydro[2,3']bipyridinyl Dihydrochloride;

3-(Thiophen-3-ylmethylene)-3,4,5,6-tetrahydro[2,3']bipyridinyl Dihydrochloride;

3-(Benzo[b]thiophen-3-ylmethylene)-3,4,5,6-tetrahydro[2,3']bipyridinyl Dihydrochloride;

3-(2,3-Dihydrobenzofuran-5-ylmethylene)-3,4,5,6-tetrahydro[2,3']bipyridinyl Dihydrochloride;

3-(3,4-Dihydro-2H-benzo[b][1,4]dioxepin-7-ylmethylene)-3,4,5,6-tetrahydro-[2,3']bipyridinyl Dihydrochloride;

3-(2,2-Dimethylchroman-6-ylmethylene)-3,4,5,6-tetrahydro[2,3']bipyridinyl Dihydrochloride;

3-(2,2-Difluorobenzo[1,3]dioxol-5-ylmethylene)-3,4,5,6-tetrahydro[2,3']bipyridinyl Dihydrochloride;

3-(7-Methoxybenzo[1,3]dioxol-5-ylmethylene)-3,4,5,6-tetrahydro[2,3']bipyridinyl Dihydrochloride;

3-(Benzo[1,3]dioxol-5-ylmethylene)-3,4,5,6-tetrahydro[2,3']bipyridinyl;

3-(5-Bromo-1H-indol-3-ylmethylene)-3,4,5,6-tetrahydro[2,3']bipyridinyl;

4-(5,6-Dihydro-4H-[2,3']bipyridinyl-3-ylidenemethyl)-2-nitrophenol;

3-(1-Methyl-1H-pyrrol-2-ylmethylene)-3,4,5,6-tetrahydro[2,3']bipyridinyl;

3-(5,6-Dihydro-4H-[2,3']bipyridinyl-3-ylidenemethyl)cinnoline;

3-(3-Nitro-4-piperidin-1-ylbenzylidene)-3,4,5,6-tetrahydro[2,3']bipyridinyl;

3-(4-(Pyrazol-1-yl)benzylidene)-3,4,5,6-tetrahydro[2,3']bipyridinyl;

7-(5,6-Dihydro-4H-[2,3']bipyridinyl-3-ylidenemethyl)-4H-benzo[1,4]oxazin-3-one;

6-(5,6-Dihydro-4H-[2,3']bipyridinyl-3-ylidenemethyl)-4H-benzo[1,4]oxazin-3-one;

3-(3-Morpholin-4-ylbenzylidene)-3,4,5,6-tetrahydro[2,3']bipyridinyl;

3-(3-Pyrrolidin-1-ylbenzylidene)-3,4,5,6-tetrahydro[2,3']bipyridinyl;

3-[3-(4-Methylpiperazin-1-yl)benzylidene]-3,4,5,6-tetrahydro[2,3']bipyridinyl;

3-(Benzo[1,3]dioxol-4-ylmethylene)-3,4,5,6-tetrahydro[2,3']bipyridinyl Dihydrochloride, 3-(4-Pyrrolidin-1-yl-benzylidene)-3,4,5,6-tetrahydro[2,3']bipyridinyl, 3-[2-(4-Methylpiperazin-1-yl)benzylidene]-3,4,5,6-tetrahydro[2,3']bipyridinyl, 3-(1H-Indazol-6-ylmethylene)-3,4,5,6-tetrahydro[2,3']bipyridinyl, 3-(1H-Indazol-5-ylmethylene)-3,4,5,6-tetrahydro[2,3']bipyridinyl, 3-(2-Morpholin-4-ylbenzylidene)-3,4,5,6-tetrahydro[2,3']bipyridinyl, 3-(1H-Benztriazol-5-ylmethylene)-3,4,5,6-tetrahydro[2,3']bipyridinyl, 5-(5,6-Dihydro-4H-[2,3']bipyridinyl-3-ylidenemethyl)-1,3-dihydrobenzimidazol-2-one, 3-(1H-Benzimidazol-5-ylmethylene)-3,4,5,6-tetrahydro[2,3']bipyridinyl, 3-(4-Morpholin-4-yl-benzylidene)-3,4,5,6-tetrahydro[2,3']bipyridinyl, 3-[4-(4-Methylpiperazin-1-yl)benzylidene]-3,4,5,6-tetrahydro[2,3']bipyridinyl, 3-(5,6-Dihydro-4H-[2,3']bipyridinyl-3-ylidenemethyl)-10-methyl-10H-phenothiazine, 7-(5,6-Dihydro-4H-[2,3']bipyridinyl-3-ylidenemethyl)-4-methyl-3,4-dihydro-2H-benzo[1,4]oxazine, 3-(1H-Pyrrolo[2,3-b]pyridin-3-ylmethylene)-3,4,5,6-tetrahydro[2,3']bipyridinyl, 3-(6-Methoxy-1H-indol-3-ylmethylene)-3,4,5,6-tetrahydro[2,3']bipyridinyl, 3-(5,6-Dihydro-4H-[2,3']-bipyridinyl-3-ylidenemethyl)-9-methyl-9H-carbazole, 3-(4-Methoxy-1H-indol-3-ylmethylene)-3,4,5,6-tetrahydro[2,3']bipyridinyl, 3-(7-Methoxy-1H-indol-3-ylmethylene)-3,4,5,6-tetrahydro[2,3']bipyridinyl, 3-(6-Fluoro-1H-indol-3-ylmethylene)-3,4,5,6-tetrahydro[2,3']bipyridinyl, 3-(1H-indol-3-ylmethylene)-3,4,5,6-tetrahydro[2,3']bipyridinyl dihydrochloride, 3-(1H-indol-6-ylmethylene)-3,4,5,6-tetrahydro[2,3']bipyridinyl, 3-(5,6-Dihydro-4H-[2,3']bipyridinyl-3-ylidenemethyl)-9-ethyl-9H-carbazole dihydrochloride, 3-(1-Benzyl-1H-indol-3-ylmethylene)-3,4,5,6-tetrahydro[2,3']bipyridinyl, 3-(5,6-Dihydro-4H-[2,3']bipyridinyl-3-ylidenemethyl)-9-ethyl-9H-carbazole, 3-(5-Nitro-1H-indol-3-ylmethylene)-3,4,5,6-tetrahydro[2,3']bipyridinyl, 3-(5-Chloro-1H-indol-3-ylmethylene)-3,4,5,6-tetrahydro-[2,3']bipyridinyl, 3-(3-Nitro-4-pyrrolidin-1-ylbenzylidene)-3,4,5,6-tetrahydro[2,3']bipyridinyl, 3-(3-Amino-4-pyrrolidin-1-ylbenzylidene)-3,4,5,6-tetrahydro[2,3']bipyridinyl;
3-(3-Amino-4-piperidin-1-ylbenzylidene)-3,4,5,6-tetrahydro[2,3']bipyridinyl;
3-(3-Amino-4-morpholin-4-ylbenzylidene)-3,4,5,6-tetrahydro[2,3']bipyridinyl;
3-(5-Chloro-1H-indol-3-ylmethylene)-3,4,5,6-tetrahydro[2,3']bipyridinyl dihydrochloride;
3-(1H-Indazol-4-ylmethylene)-3,4,5,6-tetrahydro[2,3']bipyridinyl;
3-(3-Piperidin-1-ylbenzylidene)-3,4,5,6-tetrahydro[2,3']bipyridinyl;
3-(Benzothiazol-5-ylmethylene)-3,4,5,6-tetrahydro[2,3']bipyridinyl;
3-(3,4-Dihydro-2H-benzo[1,4]oxazin-7-ylmethylene)-3,4,5,6-tetrahydro[2,3']bipyridinyl;
3-(3,4-Dihydro-2H-benzo[1,4]oxazin-7-ylmethylene)-3,4,5,6-tetrahydro[2,3']bipyridinyl trihydrochloride;
3-(4-Cyclopropylmethyl-3,4-dihydro-2H-benzo[1,4]oxazin-7-ylmethylene)-3,4,5,6-tetrahydro[2,3']bipyridinyl;
3-(4-Ethyl-3,4-dihydro-2H-benzo[1,4]oxazin-7-ylmethylene)-3,4,5,6-tetrahydro[2,3']bipyridinyl;
3-(Benzothiazol-6-ylmethylene)-3,4,5,6-tetrahydro[2,3']bipyridinyl;
3-(1-Phenyl-1H-pyrrol-2-ylmethylene)-3,4,5,6-tetrahydro[2,3']bipyridinyl;
3-[2-(5,6-Dihydro-4H-[2,3']bipyridinyl-3-ylidenemethyl)pyrrol-1-yl]benzonitrile;
3-(2-Cyclohexylmethyl-2H-pyrazol-3-ylmethylene)-3,4,5,6-tetrahydro[2,3']bipyridinyl;
3-(2-Cyclopentyl-2H-pyrazol-3-ylmethylene)-3,4,5,6-tetrahydro[2,3']bipyridinyl;
3-[1-(4-Chlorophenyl)-1H-pyrrol-2-ylmethylene]-3,4,5,6-tetrahydro[2,3']bipyridinyl;
3-[1-(4-Trifluoromethoxyphenyl)-1H-pyrrol-2-ylmethylene]-3,4,5,6-tetrahydro[2,3']bipyridinyl;
3-[4-(trans-2,5-Dimethylpiperazin-1-yl)benzylidene]-3,4,5,6-tetrahydro[2,3']bipyridinyl;
[3-[4-(cis-3,5-Dimethylpiperazin-1-yl)benzylidene]-3,4,5,6-tetrahydro[2,3']bipyridinyl;
3-(4-Thiomorpholin-4-yl-benzylidene)-3,4,5,6-tetrahydro[2,3']bipyridinyl;
3-[4-(1-Oxo-1λ4-thiomorpholin-4-yl)-benzylidene]-3,4,5,6-tetrahydro-[2,3']bipyridinyl;
3-[4-(1,1-Dioxo-1λ6-thiomorpholin-4-yl)-benzylidene]-3,4,5,6-tetrahydro-[2,3']bipyridinyl;
3-[4-(2,6-Dimethylmorpholin-4-yl)benzylidene]-3,4,5,6-tetrahydro[2,3']bipyridinyl;
3-(4-[1,4]Diazepan-1-ylbenzylidene)-3,4,5,6-tetrahydro[2,3']bipyridinyl;
3-(4-piperazin-1-ylbenzylidene)-3,4,5,6-tetrahydro[2,3']bipyridinyl;
3-[3-(trans-2,5-Dimethylpiperazin-1-yl)benzylidene]-3,4,5,6-tetrahydro[2,3']bipyridinyl;
3-[3-(cis-3,5-Dimethylpiperazin-1-yl)benzylidene]-3,4,5,6-tetrahydro[2,3']bipyridinyl;
3-(3-Thiomorpholin-4-yl-benzylidene)-3,4,5,6-tetrahydro[2,3']bipyridinyl;
3-[3-(2,6-Dimethylmorpholin-4-yl)benzylidene]-3,4,5,6-tetrahydro[2,3']bipyridinyl;
3-(3-[1,4]Diazepan-1-ylbenzylidene)-3,4,5,6-tetrahydro[2,3']bipyridinyl;
3-[3-(4-Phenylpiperazin-1-yl)benzylidene]-3,4,5,6-tetrahydro[2,3']bipyridinyl;
3-{3-[4-(4-Fluorophenyl)piperazin-1-yl]benzylidene}-3,4,5,6-tetrahydro[2,3']bipyridinyl;
3-(3-piperazin-1-ylbenzylidene)-3,4,5,6-tetrahydro[2,3']bipyridinyl;
3-{3-[(1S,4S)-2,5-Diazabicyclo[2.2.1]hept-2-yl]benzylidene}-3,4,5,6-tetrahydro[2,3']bipyridinyl;
3-(3-[1,4]Oxazepan-4-ylbenzylidene)-3,4,5,6-tetrahydro[2,3']bipyridinyl;
3-[4-(4-Phenylpiperazin-1-yl)benzylidene]-3,4,5,6-tetrahydro[2,3']bipyridinyl;
3-{4-[4-(4-Fluorophenyl)piperazin-1-yl]benzylidene}-3,4,5,6-tetrahydro[2,3']bipyridinyl;
3-{4-[(1S,4S)-2,5-Diazabicyclo[2.2.1]hept-2-yl]benzylidene}-3,4,5,6-tetrahydro[2,3']bipyridinyl;
3-(4-[1,4]Oxazepan-4-ylbenzylidene)-3,4,5,6-tetrahydro[2,3']bipyridinyl;
3-[4-(3-Methylpiperazin-1-yl)benzylidene]-3,4,5,6-tetrahydro[2,3']bipyridinyl;
3-[4-(2-Methylpiperazin-1-yl)benzylidene]-3,4,5,6-tetrahydro[2,3']bipyridinyl;
3-[3-(4-Ethylpiperazin-1-yl)benzylidene]-3,4,5,6-tetrahydro[2,3']bipyridinyl;
3-[4-(4-Ethylpiperazin-1-yl)benzylidene]-3,4,5,6-tetrahydro[2,3']bipyridinyl;
3-[1-(4-Chlorobenzyl)-1H-pyrrol-2-ylmethylene]-3,4,5,6-tetrahydro[2,3']bipyridinyl;
3-[1-(4-Fluorobenzyl)-1H-pyrrol-2-ylmethylene]-3,4,5,6-tetrahydro[2,3']bipyridinyl;
3-[1-(4-Trifluoromethylbenzyl)-1H-pyrrol-2-ylmethylene]-3,4,5,6-tetrahydro[2,3']bipyridinyl;
3-[1-(4-Chlorobenzyl)-1H-pyrazol-3-ylmethylene]-3,4,5,6-tetrahydro[2,3']bipyridinyl;
3-[1-(4-Fluorobenzyl)-1H-pyrazol-3-ylmethylene]-3,4,5,6-tetrahydro[2,3']bipyridinyl;
3-[1-(2,6-Dichlorobenzyl)-1H-pyrrol-2-ylmethylene]-3,4,5,6-tetrahydro[2,3']bipyridinyl;
3-[1-(3,4-Dichlorobenzyl)-1H-pyrrol-2-ylmethylene]-3,4,5,6-tetrahydro[2,3']bipyridinyl;
3-[1-(4-Trifluoromethoxybenzyl)-1H-pyrrol-2-ylmethylene]-3,4,5,6-tetrahydro[2,3']bipyridinyl;
3-(1-Biphenyl-4-ylmethyl-1H-pyrrol-2-ylmethylene)-3,4,5,6-tetrahydro[2,3']bipyridinyl;
3-[1-(2-Fluorobenzyl)-1H-pyrrol-2-ylmethylene]-3,4,5,6-tetrahydro[2,3']bipyridinyl;
3-(1-Methylpropyl-1H-pyrrol-2-ylmethylene)-3,4,5,6-tetrahydro[2,3']bipyridinyl;
3-(1-Pyridin-4-ylmethyl-1H-pyrrol-2-ylmethylene)-3,4,5,6-tetrahydro[2,3']bipyridinyl;
3-[1-(1-Ethylpropyl)-1H-pyrrol-2-ylmethylene]-3,4,5,6-tetrahydro[2,3']bipyridinyl;
3-[1-(2-Chloro-6-fluorobenzyl)-1H-pyrrol-2-ylmethylene]-3,4,5,6-tetrahydro[2,3']bipyridinyl;
3-(1-Pentafluorophenylmethyl-1H-pyrrol-2-ylmethylene)-3,4,5,6-tetrahydro[2,3']bipyridinyl;
3-[1-(2,4,5-Trifluorobenzyl)-1H-pyrrol-2-ylmethylene]-3,4,5,6-tetrahydro[2,3']bipyridinyl;
3-(1-Ethyl-1H-pyrazol-3-ylmethylene)-3,4,5,6-tetrahydro[2,3']bipyridinyl;
3-[1-(2-Methylpropyl)-1H-pyrazol-3-ylmethylene]-3,4,5,6-tetrahydro[2,3']bipyridinyl;
3-(1-Cyclopropylmethyl-1H-pyrazol-3-ylmethylene)-3,4,5,6-tetrahydro[2,3']bipyridinyl;
3-(1-Cyclobutylmethyl-1H-pyrazol-3-ylmethylene)-3,4,5,6-tetrahydro-[2,3']bipyridinyl;
3-(1-Cyclohexylmethyl-1H-pyrazol-3-ylmethylene)-3,4,5,6-tetrahydro[2,3']bipyridinyl;
3-(1-Cyclopentyl-1H-pyrazol-3-ylmethylene)-3,4,5,6-tetrahydro[2,3']bipyridinyl;

3-[5-Bromo-2-(4-chlorobenzyl)-2H-pyrazol-3-ylmethylene]-3,4,5,6-tetrahydro[2,3']bipyridinyl;
3-[4-(4-Cyclopropylmethylpiperazin-1-yl)benzylidene]-3,4,5,6-tetrahydro[2,3']bipyridinyl;
3-[4-(4-Cyclopentylpiperazin-1-yl)benzylidene]-3,4,5,6-tetrahydro[2,3']bipyridinyl;
3-{4-[(1S,4S)-5-Methyl-2,5-Diazabicyclo[2.2.1]hept-2-yl]benzylidene}-3,4,5,6-tetrahydro[2,3']bipyridinyl;
3-{4-[(1S,4S)-5-Ethyl-2,5-Diazabicyclo[2.2.1]hept-2-yl]benzylidene}-3,4,5,6-tetrahydro[2,3']bipyridinyl;
3-{4-[(1S,4S)-5-Cyclopropylmethyl-2,5-Diazabicyclo[2.2.1]hept-2-yl]benzylidene}-3,4,5,6-tetrahydro[2,3']bipyridinyl;
3-[4-(4-Methyl[1,4]diazepan-1-yl)benzylidene]-3,4,5,6-tetrahydro[2,3']bipyridinyl;
3-[4-(4-Cyclopropylmethyl[1,4]diazepan-1-yl)benzylidene]-3,4,5,6-tetrahydro[2,3']bipyridinyl;
3-[4-(4-Cyclopentyl[1,4]diazepan-1-yl)-benzylidene]-3,4,5,6-tetrahydro[2,3']bipyridinyl
3-[4-(4-Isobutyl-[1,4]diazepan-1-yl)-benzylidene]-3,4,5,6-tetrahydro-[2,3']bipyridinyl;
3-{4-[(1S,4S)-5-(2-Methylpropyl)-2,5-diazabicyclo[2.2.1]hept-2-yl]benzylidene}-3,4,5,6-tetrahydro[2,3']bipyridinyl;
3-{4-[(1S,4S)-5-Cyclopentyl-2,5-diazabicyclo[2.2.1]hept-2-yl]benzylidene}-3,4,5,6-tetrahydro[2,3']bipyridinyl;
3-[4-(4-Ethyl[1,4]diazepan-1-yl)benzylidene]-3,4,5,6-tetrahydro[2,3']bipyridinyl;
Cyclopropyl-{4-[4-(5,6-dihydro-4H-[2,3']bipyridinyl-3-ylidenemethyl)phenyl]piperazin-1-yl}methanone;
1-{4-[4-(5,6-Dihydro-4H-[2,3']bipyridinyl-3-ylidenemethyl)phenyl]piperazin-1-yl}propan-1-one;
1-{4-[4-(5,6-Dihydro-4H-[2,3']bipyridinyl-3-ylidenemethyl)phenyl]piperazin-1-yl}-2,2,2-trifluoroethanone;
Cyclopropyl-{(1S,4S)-5-[4-(5,6-dihydro-4H-[2,3']bipyridinyl-3-ylidenemethyl)phenyl]-2,5-diazabicyclo[2.2.1]hept-2-yl}methanone;
Cyclopropyl-{4-[4-(5,6-dihydro-4H-[2,3']bipyridinyl-3-ylidenemethyl)phenyl][1,4]diazepan-1-yl}methanone;
1-{(1S,4S)-5-[4-(5,6-Dihydro-4H-[2,3']bipyridinyl-3-ylidenemethyl)phenyl]-2,5-diazabicyclo[2.2.1]hept-2-yl}-2,2,2-trifluoroethanone;
1-{(1S,4S)-5-[4-(5,6-Dihydro-4H-[2,3']bipyridinyl-3-ylidenemethyl)phenyl]-2,5-diazabicyclo[2.2.1]hept-2-yl}propan-1-one;
1-{4-[4-(5,6-Dihydro-4H-[2,3']bipyridinyl-3-ylidenemethyl)phenyl][1,4]diazepan-1-yl}-2,2,2-trifluoroethanone;
1-{4-[4-(5,6-Dihydro-4H-[2,3']bipyridinyl-3-ylidenemethyl)phenyl][1,4]diazepan-1-yl}propan-1-one;
Cyclopropyl-{(1S,4S)-5-[3-(5,6-dihydro-4H-[2,3']bipyridinyl-3-ylidenemethyl)phenyl]-2,5-diazabicyclo[2.2.1]hept-2-yl}methanone;
1-{(1S,4S)-5-[3-(5,6-Dihydro-4H-[2,3']bipyridinyl-3-ylidenemethyl)phenyl]-2,5-diazabicyclo[2.2.1]hept-2-yl}-2,2,2-trifluoroethanone;
Cyclopropyl-{4-[3-(5,6-dihydro-4H-[2,3']bipyridinyl-3-ylidenemethyl)phenyl]-[1,4]diazepan-1-yl}methanone;
1-{4-[3-(5,6-Dihydro-4H-[2,3']bipyridinyl-3-ylidenemethyl)phenyl][1,4]diazepan-1-yl}-2,2,2-trifluoroethanone;
1-{4-[3-(5,6-Dihydro-4H-[2,3']bipyridinyl-3-ylidenemethyl)phenyl]-[1,4]diazepan-1-yl}propan-1-one;
3-(Benzo[1,3]dioxol-5-ylmethylene)-5'-methyl-3,4,5,6-tetrahydro[2,3']bipyridinyl;
3-(1H-Indol-3-ylmethylene)-5'-methyl-3,4,5,6-tetrahydro[2,3']bipyridinyl;
5'-Methyl-3-(1H-pyrrol-2-ylmethylene)-3,4,5,6-tetrahydro[2,3']bipyridinyl;
3-(Benzo[1,3]dioxol-5-ylmethylene)-5'-fluoro-3,4,5,6-tetrahydro[2,3']bipyridinyl;
5'-Fluoro-3-(1H-indol-3-ylmethylene)-3,4,5,6-tetrahydro[2,3']bipyridinyl;
5'-Fluoro-3-(1H-pyrrol-2-ylmethylene)-3,4,5,6-tetrahydro[2,3']bipyridinyl;
3-(2,3-Dihydrobenzo[1,4]dioxin-6-ylmethylene)-5'-fluoro-3,4,5,6-tetrahydro[2,3']bipyridinyl;
3-(1-Cyclopropylmethyl-1H-pyrrol-2-ylmethylene)-5'-fluoro-3,4,5,6-tetrahydro[2,3']bipyridinyl;
5'-Fluoro-3-(4-morpholin-4-ylbenzylidene)-3,4,5,6-tetrahydro[2,3']bipyridinyl;
3-(1H-Indol-3-ylmethylene)-6'-trifluoromethyl-3,4,5,6-tetrahydro[2,3'];

and physiologically acceptable salts thereof.

In addition, in accordance with the invention, preferred compounds are those described by subformulas I'a-I'i, which correspond to Formula I', but exhibit the following preferred groups:

I'a A is dihydrobenzofuranyl, e.g., 2,3-dihydrobenzofuran-5-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

I'b A is dihydrobenzodioxinyl, e.g., 2,3-dihydrobenzo[1,4]dioxin-6-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

I'c A is chromanyl, e.g., chroman-6-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

I'd A is dihydrobenzodioxepinyl, e.g., 3,4-dihydro-2H-benzo[b][1,4]dioxepin-7-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

I'e A is indolyl, e.g., indol-3-yl, indol-4-yl, indol-5-yl, indol-6-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

I'f A is phenyl substituted by a heterocylic group, e.g., 4-(4-morpholinyl)-phenyl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

I'g A is benzoxazinyl, e.g, 3,4-dihydrobenzo[1,4]oxazinyl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

I'h A is indazolyl, e.g., indazol-3-yl, indazol-5-yl, indazol-6-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

I'i A is benzoimidazolyl, e.g., benzoimidazol-5-yl, which is unsubstituted or substituted by alkyl, alkoxy, halogen, carboxy, oxo, nitro, alkoxycarbonyl, cyano, trifluoromethyl, amino, monoalkylamino, dialkylamino, hydroxyl, or hydroxyalkyl.

According to a further preferred compound aspect of the invention, the compound of Formula I' is selected from:

N-[4-(5,6-Dihydro-4H-[2,3']bipyridinyl-3-ylidenemethyl) phenyl]acetamide;
3-Quinolin-2-ylmethylene-3,4,5,6-terahydro[2,3']bipyridinyl;
3-Quinolin-3-ylmethylene-3,4,5,6-terahydro[2,3']bipyridinyl;
3-(3,4-Dihydroquinolin-4-ylmethylene)-3,4,5,6-terahydro[2,3']bipyridinyl;
3-[1-(Toluene-4-sulfonyl-1H-indol-4-ylmethylene]-3,4,5,6-tetrahydro[2,3']bipyridinyl;
3-(1H-indol-3-ylmethylene)-3,4,5,6-tetrahydro[2,3']bipyridinyl;
3-(1H-indol-4-ylmethylene)-3,4,5,6-tetrahydro[2,3']bipyridinyl;
3-(1H-Pyrrol-2-ylmethylene)-3,4,5,6-tetrahydro[2,3']bipyridinyl;
3-(5,6-Dihydro-4H-[2,3']bipyridinyl-3-ylidenemethyl-1H-indole-6-carboxylic acid Methyl Ester;
3-(5-Methoxy-1H-Indol-3-ylmethylene)-3,4,5,6-tetrahydro[2,3']bipyridinyl;
3-(1H-Indol-5-ylmethylene)-3,4,5,6-tetrahydro[2,3']bipyridinyl;
3-(6-Benzyloxy-2H-pyrrolo[3,3-c]pyridin-1-ylmethylene)-3,4,5,6-tetrahydro[2,3']bipyridinyl;
3-(1-methyl-1H-indol-2-ylmethylene)-3,4,5,6-tetrahydro[2,3']bipyridinyl;
3-(1-methyl-1H-indol-3-ylmethylene)-3,4,5,6-tetrahydro[2,3']bipyridinyl;
3-(4-Benzyloxy-1H-indol-3-ylmethylene)-3,4,5,6-tetrahydro[2,3']bipyridinyl;
3-(2-Methyl-1H-indol-3-ylmethylene)-3,4,5,6-tetrahydro[2,3']bipyridinyl;
3-(3H-Imidazol-4-ylmethylene)-3,4,5,6-tetrahydro[2,3']bipyridinyl;
3-(1-Methyl-1H-pyrrol-3-ylmethylene)-3,4,5,6-tetrahydro[2,3']bipyridinyl;
3-(5-Fluoro-1H-indol-3-ylmethylene)-3,4,5,6-tetrahydro[2,3']bipyridinyl;
3-(6-Methyl-1H-indol-3-ylmethylene)-3,4,5,6-tetrahydro[2,3']bipyridinyl;
3-(7-Methyl-1H-indol-3-ylmethylene)-3,4,5,6-tetrahydro[2,3']bipyridinyl;
3-(5-Benzyloxy-1H-indol-3-ylmethylene)-3,4,5,6-tetrahydro[2,3']bipyridinyl;
3-(5-Nitro-2-methyl-1H-indol-3-ylmethylene)-3,4,5,6-tetrahydro[2,3']bipyridinyl;
[5-(5,6-Dihydro-4H-[2,3']bipyridinyl-3-ylidenemethyl)benzofuran-2-yl]phenylmethanone;
6-(5,6-Dihydro-4H-[2,3']bipyridinyl-3-ylidenemethyl) chromen-2-one;
3-[6-(4-Tolylsulfanyl)pyridin-3-ylmethylene]-3,4,5,6-tetrahydro[2,3']bipyridinyl;
3-[6-(4-Tolyloxy)pyridin-3-ylmethylene]-3,4,5,6-tetrahydro[2,3']bipyridinyl;
3-(4-Methanesulfonylbenzylidene)-3,4,5,6-tetrahydro[2,3']bipyridinyl;
3-(4-Difluoromethoxybenzylidene)-3,4,5,6-tetrahydro[2,3']bipyridinyl Dihydrochloride;
3-(4-Phenoxybenzylidene)-3,4,5,6-tetrahydro[2,3']bipyridinyl;
3-(5'-Bromo-1H,1'H-[2,2']bipyrrolyl-5-ylmethylene)-3,4,5,6-tetrahydro[2,3']bipyridinyl Dihydrochloride;
5-(5,6-Dihydro-4H-[2,3']bipyridinyl-3-ylidenemethyl)-1H-pyrrole-2-carboxylic acid Dihydrochloride;
3-(2,3-Dihydrobenzo[1,4]dioxin-6-ylmethylene)-3,4,5,6-tetrahydro[2,3']bipyridinyl Dihydrochloride;
3-[5-(4-Bromo-phenyl)-thiophen-2-ylmethylene]-3,4,5,6-tetrahydro-[2,3']bipyridinyl Dihydrochloride;
3-[1-(Toluene-4-sulfonyl-1H-indol-3-ylmethylene]-3,4,5,6-tetrahydro[2,3']bipyridinyl Dihydrochloride;
3-[1-Methanesulfonyl-1H-indol-3-ylmethylene]-3,4,5,6-tetrahydro[2,3']bipyridinyl Dihydrochloride;
3-Thiophen-2-ylmethylene-3,4,5,6-tetrahydro[2,3']bipyridinyl Dihydrochloride;
3-Benzofuran-2-ylmethylene-3,4,5,6-tetrahydro[2,3']bipyridinyl Dihydrochloride;
3-(5-Propylthiophen-2-ylmethylene-3,4,5,6-tetrahydro[2,3']bipyridinyl Dihydrochloride;
3-(5-Bromothiophen-2-ylmethylene-3,4,5,6-tetrahydro[2,3']bipyridinyl Dihydrochloride;
3-(5-Methylthiophen-2-ylmethylene-3,4,5,6-tetrahydro[2,3']bipyridinyl Dihydrochloride;
3-(4-Bromo)thiophen-2-ylmethylene-3,4,5,6-tetrahydro[2,3']bipyridinyl Dihydrochloride;
4-[5-(5,6-Dihydro-4H-[2,3']bipyridinyl-3-ylidenemethyl) thiophen-2-yl]phenol Dihydrobromide;
3-Benzo[b]thiophen-2-ylmethylene-3,4,5,6-tetrahydro[2,3']bipyridinyl Dihydrochloride;
3-Thiophen-3-ylmethylene-3,4,5,6-tetrahydro[2,3']bipyridinyl Dihydrochloride;
3-Benzo[b]thiophen-3-ylmethylene-3,4,5,6-tetrahydro[2,3']bipyridinyl Dihydrochloride;
3-(4-Allyloxybenzylidene)-3,4,5,6-tetrahydro[2,3']bipyridinyl Dihydrochloride;
3-(2,3-Dihydrobenzofuran-5-ylmethylene)-3,4,5,6-tetrahydro[2,3']bipyridinyl Dihydrochloride;
3-(3,4-Dihydro-2H-benzo[b][1,4]dioxepin-7-ylmethylene)-3,4,5,6-tetrahydro-[2,3']bipyridinyl Dihydrochloride;
3-(2,2-Dimethylchroman-6-ylmethylene)-3,4,5,6-tetrahydro[2,3']bipyridinyl Dihydrochloride;
3-(2,2-Difluorobenzo[1,3]dioxol-5-ylmethylene)-3,4,5,6-tetrahydro[2,3']bipyridinyl Dihydrochloride;
3-(7-Methoxybenzo[1,3]dioxol-5-ylmethylene)-3,4,5,6-tetrahydro[2,3']bipyridinyl Dihydrochloride;
3-(3-Cyclopentyloxy-4-methoxybenzylidene)-3,4,5,6-tetrahydro[2,3']bipyridinyl Dihydrochloride;
3-(4-Methylsulfanylbenzylidene)-3,4,5,6-tetrahydro[2,3']bipyridinyl Dihydrochloride;
3-Benzo[1,3]dioxol-5-ylmethylene-3,4,5,6-tetrahydro[2,3']bipyridinyl;
3-(5-Bromo-1H-indol-3-ylmethylene)-3,4,5,6-tetrahydro[2,3']bipyridinyl;
4-(5,6-Dihydro-4H-[2,3']bipyridinyl-3-ylidenemethyl)-2-nitrophenol;
3-(1-Methyl-1H-pyrrol-2-ylmethylene)-3,4,5,6-tetrahydro[2,3']bipyridinyl;
3-(5,6-Dihydro-4H-[2,3']bipyridinyl-3-ylidenemethyl)cinnoline;
3-(3-Nitro-4-piperidin-1-ylbenzylidene)-3,4,5,6-tetrahydro[2,3']bipyridinyl;
3-(4-Pyrazol-1-ylbenzylidene)-3,4,5,6-tetrahydro[2,3']bipyridinyl;
7-(5,6-Dihydro-4H-[2,3']bipyridinyl-3-ylidenemethyl)-4H-benzo[1,4]oxazin-3-one;
6-(5,6-Dihydro-4H-[2,3']bipyridinyl-3-ylidenemethyl)-4H-benzo[1,4]oxazin-3-one;
3-(3-Morpholin-4-ylbenzylidene)-3,4,5,6-tetrahydro[2,3']bipyridinyl;

3-(3-Pyrrolidin-1-ylbenzylidene)-3,4,5,6-tetrahydro[2,3']bipyridinyl;
3-[3-(4-Methylpiperazin-1-yl)benzylidene]-3,4,5,6-tetrahydro[2,3']bipyridinyl; and
physiologically acceptable salts thereof.

Accordingly to a preferred method of use aspect of the invention, the compound of Formula I' is selected from:
3-Quinolin-2-ylmethylene-3,4,5,6-terahydro[2,3']bipyridinyl;
3-Quinolin-3-ylmethylene-3,4,5,6-terahydro[2,3']bipyridinyl;
3-(3,4-Dihydroquinolin-4-ylmethylene)-3,4,5,6-terahydro[2,3']bipyridinyl;
3-[1-(Toluene-4-sulfonyl-1H-indol-4-ylmethylene]-3,4,5,6-tetrahydro[2,3']bipyridinyl;
3-(1H-Indol-3-ylmethylene)-3,4,5,6-tetrahydro[2,3']bipyridinyl;
3-(1H-Indol-4-ylmethylene)-3,4,5,6-tetrahydro[2,3']bipyridinyl;
3-(1H-Pyrrol-2-ylmethylene)-3,4,5,6-tetrahydro[2,3']bipyridinyl;
3-(5,6-Dihydro-4H-[2,3']bipyridinyl-3-ylidenemethyl-1H-indole-6-carboxylic acid Methyl Ester;
3-(5-Methoxy-1H-indol-3-ylmethylene)-3,4,5,6-tetrahydro[2,3']bipyridinyl;
3-(1H-Indol-5-ylmethylene)-3,4,5,6-tetrahydro[2,3']bipyridinyl;
3-(6-Benzyloxy-2H-pyrrolo[3,3-c]pyridin-1-ylmethylene)-3,4,5,6-tetrahydro[2,3']bipyridinyl;
3-(1-Methyl-1H-indol-2-ylmethylene)-3,4,5,6-tetrahydro[2,3']bipyridinyl;
3-(1-Methyl-1H-indol-3-ylmethylene)-3,4,5,6-tetrahydro[2,3']bipyridinyl;
3-(4-Benzyloxy-1H-indol-3-ylmethylene)-3,4,5,6-tetrahydro[2,3']bipyridinyl;
3-(2-Methyl-1H-indol-3-ylmethylene)-3,4,5,6-tetrahydro[2,3']bipyridinyl;
3-(3H-Imidazol-4-ylmethylene)-3,4,5,6-tetrahydro[2,3']bipyridinyl;
3-(1-Methyl-1H-pyrrol-3-ylmethylene)-3,4,5,6-tetrahydro[2,3']bipyridinyl;
3-(5-Fluoro-1H-indol-3-ylmethylene)-3,4,5,6-tetrahydro[2,3']bipyridinyl;
3-(6-Methyl-1H-indol-3-ylmethylene)-3,4,5,6-tetrahydro[2,3']bipyridinyl;
3-(7-Methyl-1H-indol-3-ylmethylene)-3,4,5,6-tetrahydro[2,3']bipyridinyl;
3-(5-Benzyloxy-1H-indol-3-ylmethylene)-3,4,5,6-tetrahydro[2,3']bipyridinyl;
3-(2-Methyl-5-nitro-1H-indol-3-ylmethylene)-3,4,5,6-tetrahydro[2,3']bipyridinyl;
[5-(5,6-Dihydro-4H-[2,3']bipyridinyl-3-ylidenemethyl)benzofuran-2-yl]phenylmethanone;
6-(5,6-Dihydro-4H-[2,3']bipyridinyl-3-ylidenemethyl)chromen-2-one;
3-(5'-Bromo-1H,1'H-[2,2']bipyrrolyl-5-ylmethylene)-3,4,5,6-tetrahydro[2,3']bipyridinyl Dihydrochloride;
5-(5,6-Dihydro-4H-[2,3']bipyridinyl-3-ylidenemethyl)-1H-thiophene-2-carboxylic acid Dihydrochloride;
3-(2,3-Dihydrobenzo[1,4]dioxin-6-ylmethylene)-3,4,5,6-tetrahydro[2,3']bipyridinyl Dihydrochloride;
3-[5-(4-Bromophenyl)-thiophen-2-ylmethylene]-3,4,5,6-tetrahydro-[2,3']bipyridinyl Dihydrochloride;
3-[1-(Toluene-4-sulfonyl-1H-indol-3-ylmethylene]-3,4,5,6-tetrahydro[2,3']bipyridinyl Dihydrochloride;
3-[1-Methanesulfonyl-1H-indol-3-ylmethylene]-3,4,5,6-tetrahydro[2,3']bipyridinyl Dihydrochloride;
3-(Thiophen-2-ylmethylene)-3,4,5,6-tetrahydro[2,3']bipyridinyl Dihydrochloride;
3-(Benzofuran-2-ylmethylene)-3,4,5,6-tetrahydro[2,3']bipyridinyl Dihydrochloride;
3-(5-Propylthiophen-2-ylmethylene)-3,4,5,6-tetrahydro[2,3']bipyridinyl Dihydrochloride;
3-(5-Bromothiophen-2-ylmethylene)-3,4,5,6-tetrahydro[2,3']bipyridinyl Dihydrochloride;
3-(5-Methylthiophen-2-ylmethylene)-3,4,5,6-tetrahydro[2,3']bipyridinyl Dihydrochloride;
3-(4-Bromothiophen-2-ylmethylene)-3,4,5,6-tetrahydro[2,3']bipyridinyl Dihydrochloride;
4-[5-(5,6-Dihydro-4H-[2,3']bipyridinyl-3-ylidenemethyl)thiophen-2-yl]phenol Dihydrobromide;
3-(Benzo[b]thiophen-2-ylmethylene)-3,4,5,6-tetrahydro[2,3']bipyridinyl Dihydrochloride;
3-(Thiophen-3-ylmethylene)-3,4,5,6-tetrahydro[2,3']bipyridinyl Dihydrochloride;
3-(Benzo[b]thiophen-3-ylmethylene)-3,4,5,6-tetrahydro[2,3']bipyridinyl Dihydrochloride;
3-(2,3-Dihydrobenzofuran-5-ylmethylene)-3,4,5,6-tetrahydro[2,3']bipyridinyl Dihydrochloride;
3-(3,4-Dihydro-2H-benzo[b][1,4]dioxepin-7-ylmethylene)-3,4,5,6-tetrahydro-[2,3']bipyridinyl Dihydrochloride;
3-(2,2-Dimethylchroman-6-ylmethylene)-3,4,5,6-tetrahydro[2,3']bipyridinyl Dihydrochloride;
3-(2,2-Difluorobenzo[1,3]dioxol-5-ylmethylene)-3,4,5,6-tetrahydro[2,3']bipyridinyl Dihydrochloride;
3-(7-Methoxybenzo[1,3]dioxol-5-ylmethylene)-3,4,5,6-tetrahydro[2,3']bipyridinyl Dihydrochloride;
3-(Benzo[1,3]dioxol-5-ylmethylene)-3,4,5,6-tetrahydro[2,3']bipyridinyl;
3-(5-Bromo-1H-indol-3-ylmethylene)-3,4,5,6-tetrahydro[2,3']bipyridinyl;
4-(5,6-Dihydro-4H-[2,3']bipyridinyl-3-ylidenemethyl)-2-nitrophenol;
3-(1-Methyl-1H-pyrrol-2-ylmethylene)-3,4,5,6-tetrahydro[2,3']bipyridinyl;
3-(5,6-Dihydro-4H-[2,3']bipyridinyl-3-ylidenemethyl)cinnoline;
3-(3-Nitro-4-piperidin-1-ylbenzylidene)-3,4,5,6-tetrahydro[2,3']bipyridinyl;
3-(4-(Pyrazol-1-yl)benzylidene)-3,4,5,6-tetrahydro[2,3']bipyridinyl;
7-(5,6-Dihydro-4H-[2,3']bipyridinyl-3-ylidenemethyl)-4H-benzo[1,4]oxazin-3-one;
6-(5,6-Dihydro-4H-[2,3']bipyridinyl-3-ylidenemethyl)-4H-benzo[1,4]oxazin-3-one;
3-(3-Morpholin-4-ylbenzylidene)-3,4,5,6-tetrahydro[2,3']bipyridinyl;
3-(3-Pyrrolidin-1-ylbenzylidene)-3,4,5,6-tetrahydro[2,3']bipyridinyl;
3-[3-(4-Methylpiperazin-1-yl)benzylidene]-3,4,5,6-tetrahydro[2,3']bipyridinyl; and
physiologically acceptable salts thereof.

A preferred starting materials for use in the synthesis of compounds of formula I is 3-(4-iodobenzylidene)-3,4,5,6-tetrahydro[2,3']bipyridinyl and is 3-(3-iodobenzylidene)-3,4,5,6-tetrahydro[2,3']bipyridinyl.

The preferred aspects include pharmaceutical compositions comprising a compound of this invention and a pharmaceutically acceptable carrier and, optionally, another active agent as discussed below; a method of stimulating or activating inhibiting alpha-7 nicotinic receptors, e.g., as determined by a conventional assay or one described herein, either in vitro or in vivo (in an animal, e.g., in an animal model, or in a mammal or in a human); a method of treating a neurological syndrome, e.g., loss of memory, especially long-term memory, cognitive impairment or decline, memory impairment, etc. method of treating a disease state modulated by nicotinic alpha-7 activity, in a mammal, e.g., a human, e.g., those mentioned herein.

The compounds of the present invention may be prepared conventionally. Some of the known processes that can be used are described below. All starting materials are known or can be conventionally prepared from known starting materials.

The aldehydes used in the preparation of the nicotinic ligands are commercially available or were prepared by literature procedures. For example, 5-formylbenzimidazole can be prepared by benzylic oxidation of the 5-methyl precursor. [Talaty, C. N.; Zenker, N.; Callery, P. S. *Oxidation of Methylbenzimidazoles with Ceric Ammonium Nitrate. J. Heterocyclic Chem.* 1976, 1121-1123]. 5-Formyl-2-oxobenzimidazole can be prepared from methyl 3,4-diaminobenzoate by urethane formation followed by a reduction/oxidation sequence. [Schmidt, G.; Zeiler, H.-J.; Metzger, K. G. Novel β-Lactam Antibiotics. U.S. Pat. No. 4,748,163, May 31, 1988.] 5-Formylindazole can be prepared from 4-bromo-2-methylaniline by diazotization followed by metal-halogen exchange and trapping with a formamide. [DeLucca, G. V. Substituted 2H-1,3-Diazapin-2-one Useful as an HIV Protease Inhibitor. U.S. Pat. No. 6,313,110 B1, Nov. 6, 2001.] 5-Formylbenzothiophene can be prepared from 4-bromothiophenol by S-alkylation with an acetaldehyde equivalent followed by cyclization, metal-halogen exchange, and trapping with an formamide. [Barker, P.; Finke, P.; Thompsom, K. *Synth. Comm.* 1989, 257-265.]

The nicotinic ligands can be prepared by the condensation of anabasine with an excess of the requisite aldehydes under either acidic or mildly acidic, buffered conditions. [Kem, W. R.; Zoltewicz, J. A.; Meyer, E. M.; Katalin, P.-T. Anabasine Derivatives Useful in the Treatment of Degeneratives Diseases of the Nervous System. U.S. Pat. No. 5,741,802, Apr. 21, 1998.] The condensations are generally performed at elevated temperatures for 24 hours. The resultant adducts of Formula I or Formula I' can be isolated and purified by standard techniques, such as chromatography or recrystallization, practiced by those skilled in the art.

The nicotinic ligands can, alternatively, be prepared by modification of other nicotinic ligands. For example, the benzoxazol-2-one ligand was prepared from the corresponding nitro phenol ligand by selective reduction and carbamate formation. The 3-(3-Morpholin-4-ylbenzylidene) ligand was prepared from the corresponding iodide ligand by a palladium-catalyzed amination [see, e.g., Ali, M. H.; Buchwald, S. L. *An Improved Method for the Palladium-Catalyzed Amination of Aryl Iodides. J. Org. Chem.* 2001, 66, 2560-2565].

One of ordinary skill in the art will recognize that some of the compounds of Formula I or Formula I' can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formula I or Formula I' can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, $^3$H, $^{11}$C, $^{13}$C and/or $^{14}$C. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr. Pharm. Des., 2000; 6(10)](2000), 110 pp. CAN 133:68895 AN 2000:473538 CAPLUS; Kabalka, George W.; Varma, Rajender S. The synthesis of radiolabeled compounds VIA organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formula I or Formula I', containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their alpha-7 stimulating activity and, preferably their high degree of selectivity, the compounds of the present invention can be administered to anyone needing stimulation of alpha-7 receptors. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or memory loss, e.g., other α-7 agonists, PDE4 inhibitors, calcium channel blockers, muscarinic m1 and m2 modulators, adenosine receptor modulators, amphakines NMDA-R modulators, mGluR modulators, dopamine modulators, serotonin modulators, canabinoid modulators, and cholinesterase inhibitors (e.g., donepezil, rivastigimine, and glanthanamine). In such combinations, each active ingredient can be administered either in accordance with their usual dosage range or a dose below their usual dosage range.

The compounds of the invention can be used in conjunction with "positive modulators" which enhance the efficacy of nicotinic receptor agonists. See, e.g., the positive modulators disclosed in WO 99/56745, WO 01/32619, and WO 01/32622. Such combinational therapy can be used in treating conditions/diseases associated with reduced nicotinic transmission.

Further the compounds may be used in conjunction with compounds that bind to Aβ peptides and thereby inhibit the binding of the peptides to α7nAChr subtypes. See, e.g., WO 99/62505.

The present invention further includes methods of treatment that involve activation of α-7 nicotinic receptors. Thus, the present invention includes methods of selectively activating/stimulating α-7 nicotinic receptors in animals, e.g., mammals, especially humans, wherein such activation/stimulation has a therapeutic effect, such as where such activation may relieve conditions involving neurological syndromes, such as the loss of memory, especially long-term memory. Such methods comprise administering to an animal in need thereof, especially a mammal, most especially a human, an effective amount of a compound of Formula I or Formula I', alone or as part of a formulation, as disclosed herein.

Agents that bind to nicotinic acetylcholine receptors have been indicated as useful in the treatment and/or prophylaxis of various diseases and conditions, particularly psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder), and other uses such as treatment of nicotine addiction, inducing smoking cessation, treating pain (i.e., analgesic use), providing neuroprotection, and treating jetlag. See, e.g., WO 97/30998; WO 99/03850; WO 00/42044; WO 01/36417; Holladay et al., J. Med. Chem., 40:26, 4169-94 (1997); Schmitt et al., Annual Reports Med. Chem., Chapter 5, 41-51 (2000); and Stevens et al., Psychopharmatology, (1998) 136: 320-27 (1998).

Thus, in accordance with the invention, there is provided a method of treating a patient, especially a human, suffering from psychotic diseases, neurodegenerative diseases involving a dysfunction of the cholinergic system, and conditions of memory and/or cognition impairment, including, for example, schizophrenia, anxiety, mania, depression, manic depression [examples of psychotic disorders], Tourette's syndrome, Parkinson's disease, Huntington's disease [examples of neurodegenerative diseases], and/or cognitive disorders (such as Alzheimer's disease, Lewy Body Dementia, Amyotrophic Lateral Sclerosis, memory impairment, memory loss, cognition deficit, attention deficit, Attention Deficit Hyperactivity Disorder) comprising administering to the patient an effective amount of a compound according to Formula I or Formula I'.

Neurodegenerative disorders included within the methods of the present invention include, but are not limited to, treatment and/or prophylaxis of Alzheimer's diseases, Picks disease, diffuse Lewy Body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3, olivopontocerebellar degenerations, Gilles De La Tourette's disease, bulbar, pseudobulbar palsy, spinal muscular atrophy, spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (such as Creutzfeldt-Jakob, Gerstmann-Sträussler-Scheinker disease, Kuru and fatal familial insomnia), and neurodegenerative disorders resulting from cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In addition, α-7nAChRs agonists, such as the compounds of the present invention can be used to treat age-related dementia and other dementias and conditions with memory loss including age-related memory loss, senility, vascular dementia, diffuse white matter disease (Binswanger's disease), dementia of endocrine or metabolic origin, dementia of head trauma and diffuse brain damage, dementia pugilistica and frontal lobe dementia. See, e.g., WO 99/62505. Thus, in accordance with the invention, there is provided a method of treating a patient, especially a human, suffering from age-related dementia and other dementias and conditions with memory loss comprising administering to the patient an effective amount of a compound according to Formula I or Formula I'.

Thus, in accordance with a further embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formula I or Formula I'.

Amyloid precursor protein (APP) and Aβ peptides derived therefrom, e.g., $A\beta_{1-40}$, $A\beta_{1-42}$, and other fragments, are known to be involved in the pathology of Alzheimer's disease. The $A\beta_{1-42}$ peptides are not only implicated in neurotoxicity but also are known to inhibit cholinergic transmitter function. Further, it has been determined that Aβ peptides bind to α-7 nAChRs. Thus, agents which block the binding of the Aβ peptides to α-7 nAChRs are useful for treating neurodegenerative diseases. See, e.g., WO 99/62505. In addition, stimulation α-7 nAChRs can protect neurons against cytotoxicity associated with Aβ peptides. See, e.g., Kihara, T. et al., Ann. Neurol., 1997, 42, 159.

Thus, in accordance with an embodiment of the invention there is provided a method of treating and/or preventing dementia in an Alzheimer's patient which comprises administering to the subject a therapeutically effective amount of a compound according to Formula I or Formula I' to inhibit the binding of an amyloid beta peptide (preferably, $A\beta_{1-42}$) with nAChRs, preferable α-7 nAChRs, most preferably, human α-7 nAChRs (as well as a method for treating and/or preventing other clinical manifestations of Alzheimer's disease that include, but are not limited to, cognitive and language deficits, apraxias, depression, delusions and other neuropsychiatric symptoms and signs, and movement and gait abnormalities).

The present invention also provides methods for treating other amyloidosis diseases, for example, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis anthropathy, Finnish and Iowa amyloidosis, and eye disease.

In addition, nicotinic receptors have been implicated as playing a role in the body's response to alcohol ingestion. Thus, agonists for α-7nAChR's can be used in the treatment of alcohol withdrawal and in anti-intoxication therapy. Thus, in accordance with an embodiment of the invention there is provided a method of treating a patient for alcohol withdrawal or treating a patient with anti-intoxication therapy comprising administering to the patient an effective amount of a compound according to Formula I or Formula I'.

Agonists for the α-7nAChR subtypes can also be used for neuroprotection against damage associated with strokes and ischemia and glutamate-induced excitotoxicity. Thus, in accordance with an embodiment of the invention there is provided a method of treating a patient to provide for neuroprotection against damage associated with strokes and ischemia and glutamate-induced excitotoxicity comprising administering to the patient an effective amount of a compound according to Formula I or Formula I'.

As noted above, agonists for the α-7nAChR subtypes can also be used in the treatment of nicotine addiction, inducing smoking cessation, treating pain, and treating jetlag, obesity, diabetes, and inflammation. Thus, in accordance with an embodiment of the invention there is provided a method of treating a patient suffering from nicotine addiction, pain, jetlag, obesity, diabetes, and/or inflammation, or a method of inducing smoking cessation in a patient comprising administering to the patient an effective amount of a compound according to Formula I or Formula I'.

In addition, due to their affinity to α-7nAChR's, labeled derivatives of the compounds of Formula I or Formula I' (e.g., $C^{11}$ or $F^{18}$ labelled derivatives), can be used in neuroimaging of the receptors within, e.g., the brain. Thus, using such labeled agents in vivo imaging of the receptors can be performed using, e.g., PET imaging.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Thus, in accordance with an embodiment of the invention there is provided a method of treating a patient suffering from, for example, mild cognitive impairment (MCI), vascular dementia (VaD), age-associated cognitive decline (AACD), amnesia associated w/open-heart-surgery, cardiac arrest, and/ or general anesthesia, memory deficits from early exposure of anesthetic agents, sleep deprivation induced cognitive impairment, chronic fatigue syndrome, narcolepsy, AIDS-related dementia, epilepsy-related cognitive impairment, Down's syndrome, Alcoholism related dementia, drug/substance induced memory impairments, Dementia Puglistica (Boxer Syndrome), and animal dementia (eg dogs, cats, horses, etc.) patient comprising administering to the patient an effective amount of a compound according to Formula I or Formula I'.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention can be administered to mammals, particularly humans, at typical dosage levels customary for α-7 nicotinic receptor agonists such as the known α-7 nicotinic receptor agonist compounds mentioned above. For example, the compounds can be administered, in single or multiple doses, by oral administration at a dosage level of, for example, 0.0001-10 mg/kg/day, e.g., 0.01-10 mg/kg/day. Unit dosage forms can contain, for example, 1-200 mg of active compound. For intravenous administration, the compounds can be administered, in single or multiple dosages.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

EXAMPLES

All spectra were recorded at 300 MHz on a Bruker Instruments NMR. Coupling constants (J) are in Hertz (Hz) and peaks are listed relative to TMS (δ0.00 ppm). Microwave reactions were performed using a Personal Chemistry Optimizer™ microwave reactor in 2.5 mL or 5 mL Personal Chemistry microwave reactor vials. All reactions were performed at 200° C. for 600 s with the fixed hold time ON unless otherwise stated. Sulfonic acid ion exchange resins (SCX) were purchased from Varian Technologies.

Representative Procedure A

Example 1

3-(1H-Indol-3-ylmethylene)-3,4,5,6-tetrahydro[2,3']bipyridinyl from 1H-indol-3-carbaldehyde

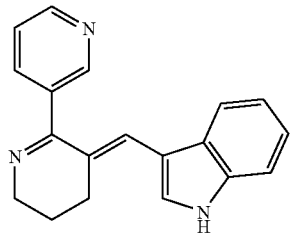

To a solution of 50.0 mg (0.220 mmol) anabaseine dihydrochloride in a buffer solution of 0.6 M acetic acid/0.3 M sodium acetate in methanol (1.5 ml) was added indole-3-carbaldehyde (63.9 mg, 0.440 mmol, 2.0 eq). The mixture was kept at 60° C. for 18 h and then poured into ice water. The solution was washed with dichloromethane, was made basic (pH 9-10) by the addition of a saturated, aqueous sodium carbonate solution, and was extracted with ethyl acetate (3×). The combined ethyl acetate layers were washed with brine, dried over anhydrous sodium sulfate, and concentrated. The residue was purified by chromatography [1/1 to 0/1 ethyl acetate/(70/30/1 ethyl acetate/methanol/ammonium hydroxide)] to provide 31.6 mg (50%) of the product. Data: $^1$H NMR (CDOD$_3$) δ 12.51 (s, 1H), 9.46 (m, 2H), 8.69 (m, 1H), 8.52 (s, 1H), 8.29 (m, 2H), 8.04 (m, 1H), 7.93 (m, 1H), 7.83 (m, 1H), 7.65 (s, 1H), 4.50 (m, 2H), 3.56 (s, 2H), 2.60 (m, 2H); MS (EI) m/z 288 (M$^+$+1).

Using this general procedure the following compounds were prepared:

Example 2

3-[1-(Toluene-4-sulfonyl-1H-indol-4-ylmethylene]-3,4,5,6-tetrahydro[2,3']bipyridinyl from 1-(toluene-4-sulfonyl)-1H-indole-4-carbaldehyde

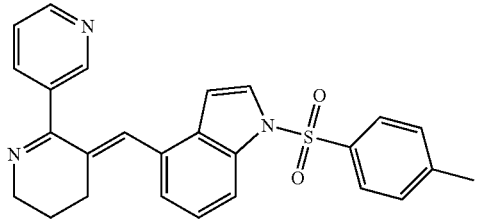

Yield 50%. $^1$H NMR (DMSO-d$_6$) δ 8.64 (m, 2H), 7.86 (m, 5H), 7.38 (m, 5H), 6.74 (s, 1H), 6.60 (m, 1H), 3.42 (m, 2H), 2.65 (m, 2H), 2.48 (s, 3H), 1.69 (m, 2H); MS (EI) m/z 442 (M$^+$+1).

Example 3

3-(1H-Indol-4-ylmethylene)-3,4,5,6-tetrahydro[2,3']bipyridinyl from 1H-indol-4-carbaldehyde

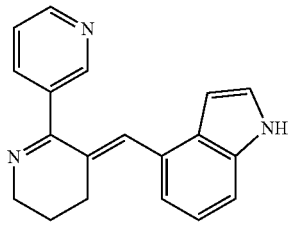

Yield: 50%. $^1$H NMR (CDOD$_3$) δ 8.65 (m, 2H), 7.95 (m, 1H), 7.64 (s, 1H), 7.55 (m, 1H), 7.37 (d, J=9.0, 1H), 7.26 (m, 1H), 7.12 (d, J=9.0, 1H), 6.80 (m, 1H), 6.47 (m, 1H), 3.81 (m, 2H), 3.02 (m, 2H), 1.91 (m, 2H); MS (EI) m/z 288 (M$^+$+1).

Example 4

3-(1H-Pyrrol-2-ylmethylene)-3,4,5,6-tetrahydro[2,3']bipyridinyl from 1H-pyrrole-2-carbaldehyde

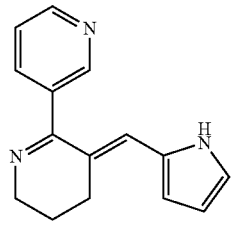

Yield: 40%. $^1$H NMR (DMSO-d$_6$) δ 11.09 (s, 1H), 8.60 (m, 2H), 7.80 (m, 1H), 7.44 (m, 1H), 6.91 (m, 1H), 6.50 (m, 1H), 6.42 (m, 1H), 6.19 (m, 1H), 3.65 (m, 2H), 2.65 (m, 2H), 1.75 (m, 2H); MS (EI) m/z 238 (M$^+$+1).

Example 5

3-(5,6-Dihydro-4H-[2,3']bipyridinyl-3-ylidenemethyl-1H-indole-6-carboxylic acid Methyl Ester from 3-formyl-1H-indole-6-carboxylic acid methyl ester

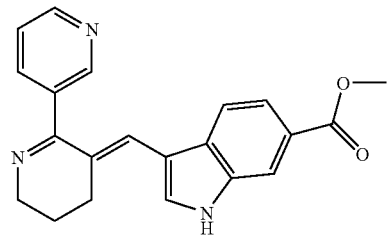

Yield: 60%. $^1$H NMR (CD$_3$OD) δ 8.68 (m, 2H), 8.14 (m, 1H), 7.98 (m, 1H), 7.88 (m, 1H), 7.73 (m, 1H), 7.61 (m, 1H), 7.33 (m, 1H), 6.96 (m, 1H), 3.90 (s, 3H), 3.78 (m, 2H), 2.89 (m, 2H), 1.96 (m, 2H); MS (EI) m/z 346 (M$^+$+1).

Example 6

3-(5-Methoxy-1H-indol-3-ylmethylene)-3,4,5,6-tetrahydro[2,3']bipyridinyl from 5-methoxy-1H-indole-3-carbaldehyde

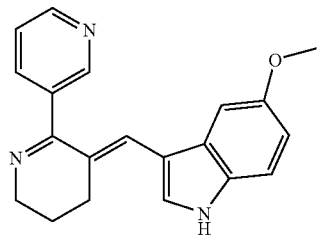

Yield: 55%. $^1$H NMR (CD$_3$OD) δ 8.67 (m, 2H), 7.98 (m, 1H), 7.63 (m, 2H), 7.30 (d, J=9.0, 1H), 6.93 (m, 1H), 6.83 (m, 1H), 6.70 (m, 1H), 3.76 (m, 2H), 3.72 (s, 3H), 2.86 (m, 2H), 1.96 (m, 2H); MS (EI) m/z 318 (M$^+$+1).

Example 7

3-(1H-Indol-5-ylmethylene)-3,4,5,6-tetrahydro[2,3']bipyridinyl from 1H-indole-5-carbaldehyde

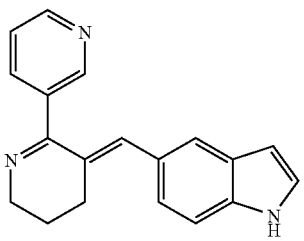

Yield: 60%. $^1$H NMR (CD$_3$OD) δ 8.63 (m, 2H), 7.94 (m, 1H), 7.62 (s, 1H), 7.54 (m, 1H), 7.37 (d, J=9.0, 1H), 7.25 (m, 1H), 7.10 (m, 1H), 6.76 (s, 1H), 6.47 (m, 1H), 3.81 (m, 2H), 3.01 (m, 2H), 1.89 (m, 2H); MS (EI) m/z 288 (M$^+$+1).

Example 8

3-(5-Benzyloxy-6-aza-1H-indol[3,3-c]pyridin-1-ylmethylene)-3,4,5,6-tetrahydro[2,3']bipyridinyl from 5-benzyloxy-1H-6-aza-indol-3-carbaldehyde

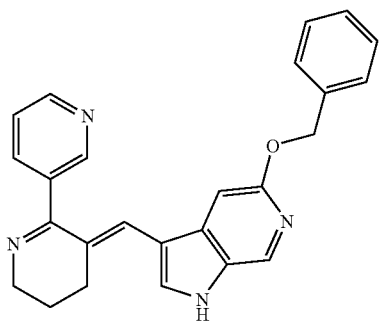

Yield: 55%. $^1$H NMR (CD$_3$OD) δ 8.68 (m, 2H), 8.34 (m, 1H), 7.97 (m, 1H), 7.88 (m, 1H), 7.59 (m, 1H), 7.36 (m, 5H), 6.81 (m, 1H), 6.64 (m, 1H), 5.25 (s, 2H), 3.77 (m, 2H), 2.82 (m, 2H), 1.94 (m, 2H); MS (EI) m/z 395 (M$^+$+1).

Example 9

3-(1-Methyl-1H-indol-2-ylmethylene)-3,4,5,6-tetrahydro[2,3']bipyridinyl from 1-methyl-1H-indol-2-carbaldehyde

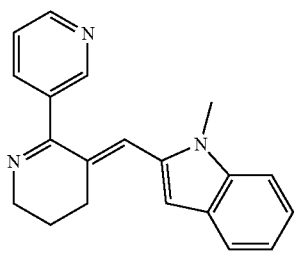

Yield: 50%. $^1$H NMR (CD$_3$OD) δ 8.69 (m, 2H), 8.01 (m, 1H), 7.60 (m, 2H), 7.33 (m, 1H), 7.21 (m, 1H), 7.06 (m, 1H), 6.88 (s, 1H), 6.77 (s, 1H), 3.84 (m, 2H), 3.53 (s, 3H), 2.98 (m, 2H), 1.95 (m, 2H); MS (EI) m/z 302 (M$^+$+1).

Example 10

3-(1-Methyl-1H-indol-3-ylmethylene)-3,4,5,6-tetrahydro[2,3']bipyridinyl from 1-methyl-1H-indol-3-carbaldehyde

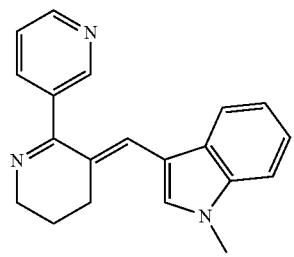

Yield %. $^1$H NMR (CD$_3$OD) δ 8.67 (m, 2H), 7.99 (m, 1H), 7.65 (s, 1H), 7.60 (m, 1H), 7.42 (m, 1H), 7.24 (m, 2H), 7.07 (m, 1H), 6.96 (m, 1H), 3.90 (s, 3H), 3.76 (m, 2H), 2.87 (m, 2H), 2.00 (m, 2H); MS (EI) m/z 302 (M$^+$+1).

Example 11

3-(4-Benzyloxy-1H-indol-3-ylmethylene)-3,4,5,6-tetrahydro[2,3']bipyridinyl from 4-benzyloxy-1H-indol-3-carbaldehyde

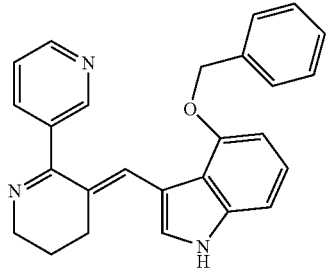

Yield: 50%. $^1$H NMR (CD$_3$OD) δ 8.60 (m, 1H), 8.43 (m, 1H), 7.86 (m, 1H), 7.81 (m, 1H), 7.56 (m, 1H), 7.27 (m, 4H), 7.14 (m, 2H), 6.97 (m, 2H), 6.50 (m, 1H), 5.01 (s, 2H), 3.75 (m, 2H), 2.84 (m, 2H), 1.95 (m, 2H); MS (EI) m/z 394 (M$^+$+1).

Example 12

3-(2-Methyl-1H-indol-3-ylmethylene)-3,4,5,6-tetrahydro[2,3']bipyridinyl from 2-methyl-1H-indol-3-carbaldehyde

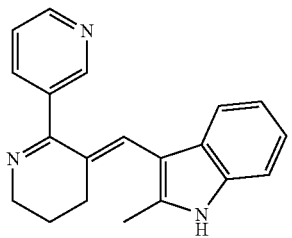

Yield: 55%. $^1$H NMR (CD$_3$OD) δ 8.67 (m, 1H), 8.62 (m, 1H), 7.98 (m, 1H), 7.54 (m, 1H), 7.30 (m, 2H), 7.05 (m, 2H), 6.76 (s, 1H), 3.87 (m, 2H), 2.69 (m, 2H), 2.29 (s, 3H), 1.87 (m, 2H); MS (EI) m/z 303 (M$^+$+2).

Example 13

3-(5-Chloro-1H-indol-3-ylmethylene)-3,4,5,6-tetrahydro-[2,3']bipyridinyl from 5-chloro-1H-indole-3-carbaldehyde

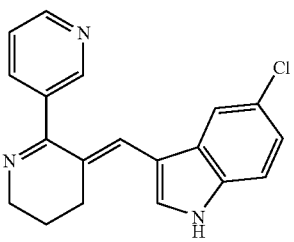

Yield: 60%. $^1$H NMR (CD$_3$OD) δ 8.70 (m, 2H), 8.00 (m, 1H), 7.72 (s, 1H), 7.60 (m, 1H), 7.38 (m, 1H), 7.19 (m, 1H), 7.17 (m, 1H), 6.87 (m, 1H), 3.78 (m, 2H), 2.86 (m, 2H), 1.95 (m, 2H); MS (EI) m/z 322 (M$^+$+1).

Example 14

3-(5-Nitro-1H-indol-3-ylmethylene)-3,4,5,6-tetrahydro[2,3']bipyridinyl from 5-nitro-1H-indole-3-carbaldehyde

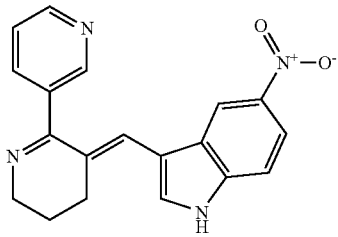

Yield: 40%. $^1$H NMR (CD$_3$OD) δ 8.67 (m, 2H), 8.21 (m, 1H), 7.97 (m, 3H), 7.54 (m, 2H), 6.87 (m, 1H), 3.70 (m, 2H), 2.75 (m, 2H), 1.77 (m, 2H); MS (EI) m/z 333 (M$^+$+1).

Example 15

3-(5,6-Dihydro-4H-[2,3']bipyridinyl-3-ylidenemethyl)-9-ethyl-9H-carbazole from 9-ethyl-9H-carbazole-3-carbaldehyde

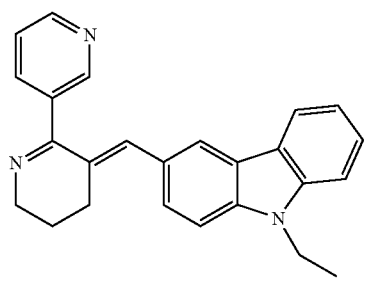

Yield: 40%. $^1$H NMR (CD$_3$OD) δ 8.66 (m, 2H), 8.12 (m, 2H), 7.97 (m, 1H), 7.54 (m, 4H), 7.20 (m, 1H), 6.85 (m, 1H), 4.43 (m, 2H), 3.84 (m, 2H), 3.09 (m, 2H), 1.93 (m, 2H), 1.41 (m, 3H); MS (EI) m/z 366 (M$^+$+1).

Example 16

3-(1-Benzyl-1H-indol-3-ylmethylene)-3,4,5,6-tetrahydro[2,3']bipyridinyl from 1-benzyl-1H-indole-3-carbaldehyde

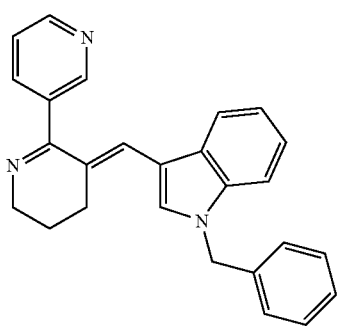

Yield: 60%. $^1$H NMR (CD$_3$OD) δ 8.68 (m, 2H), 7.98 (m, 1H), 7.79 (s, 1H), 7.59 (m, 1H), 7.26 (m, 1H), 5.49 (s, 2H), 3.78 (m, 2H), 2.86 (m, 2H), 1.95 (m, 2H); MS (EI) m/z 378 (M$^+$+1).

Example 17

3-(5,6-Dihydro-4H-[2,3']bipyridinyl-3-ylidenemethyl)-9-ethyl-9H-carbazole dihydrochloride from 9-ethyl-9H-carbazole-3-carbaldehyde

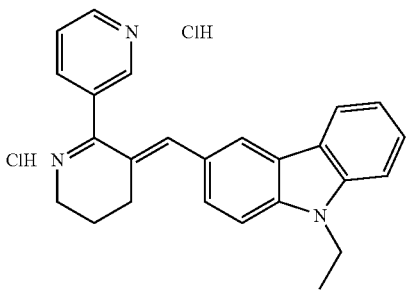

Yield: 40%. $^1$H NMR (DMSO-d6) δ 8.93 (m, 2H), 8.87 (m, 1H), 8.52 (m, 1H), 8.25 (m, 1H), 8.24 (m, 1H), 7.75 (m, 4H), 7.53 (m, 2H), 7.27 (m, 1H), 4.53 (m, 2H), 3.38 (m, 2H), 3.18 (m, 2H), 2.20 (m, 2H), 1.31 (m, 3H); MS (EI) m/z 366 (M$^+$+1).

Example 18

3-(1H-indol-6-ylmethylene)-3,4,5,6-tetrahydro[2,3']bipyridinyl from 1H-indole-6-carbaldehyde

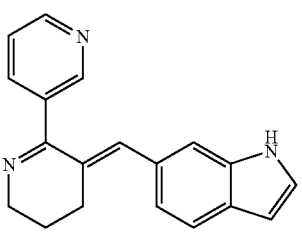

Yield: 60%. $^1$H NMR (CD$_3$OD) δ 8.63 (m, 2H), 7.95 (m, 1H), 7.54 (m, 1H), 7.44 (m, 1H), 7.31 (m, 1H), 7.02 (m, 1H), 6.75 (m, 1H), 6.44 (m, 1H), 3.81 (m, 2H), 3.02 (m, 2H), δ 1.91 (m, 2H); MS (EI) m/z 288 (M$^+$+1), 245.

Example 19

3-(1H-indol-3-ylmethylene)-3,4,5,6-tetrahydro[2,3']bipyridinyl dihydrochloride from 3-(1H-indol-3-ylmethylene)-3,4,5,6-tetrahydro[2,3']bipyridinyl

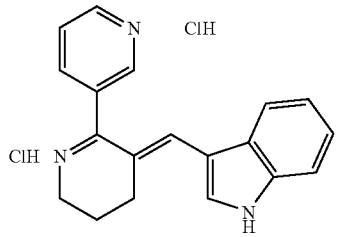

Yield: 80%. ¹H NMR (CD₃OD) δ 9.01 (m, 2H), 8.42 (m, 1H), 8.28 (m, 1H), 7.95 (m, 1H), 7.74 (m, 1H), 7.53 (m, 1H), 7.43 (m, 1H), 7.25 (m, 2H), 3.85 (m, 2H), 3.06 (s, 2H), 2.28 (m, 2H); MS (EI) m/z 288 (M⁺+1).

Example 20

3-(5-Fluoro-1H-indol-3-ylmethylene)-3,4,5,6-tetrahydro[2,3']bipyridinyl dihydrochloride from 3-(5-fluoro-1H-indol-3-ylmethylene)-3,4,5,6-tetrahydro[2,3']bipyridinyl

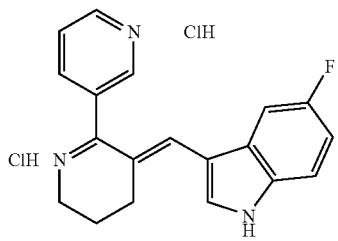

Yield: 80%. ¹H NMR (CD₃OD) δ 8.97 (m, 2H), 8.26 (m, 2H), 7.86 (m, 1H), 7.65 (m, 1H), 7.51 (m, 1H), 7.11 (m, 2H), 3.84 (m, 2H), 3.06 (m, 2H), 2.28 (m, 2H); MS (EI) m/z 306 (M⁺+1).

Example 21

3-(6-Fluoro-1H-indol-3-ylmethylene)-3,4,5,6-tetrahydro[2,3']bipyridinyl from 6-fluoroindole-3-carbaldehyde

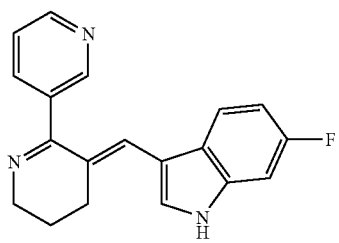

Yield: 50%. ¹H NMR (CD₃OD) δ 8.67 (m, 2H), 7.97 (m, 1H), 7.66 (m, 1H), 7.58 (m, 1H), 7.21 (m, 1H), 7.12 (m, 1H), 6.92 (m, 1H), 6.82 (m, 1H), 3.73 (m, 2H), 2.87 (m, 2H), 1.95 (m, 2H); MS (EI) m/z 306 (M⁺+1).

Example 22

3-(7-Methoxy-1H-indol-3-ylmethylene)-3,4,5,6-tetrahydro[2,3']bipyridinyl from 7-methoxyindole-3-carbaldehyde

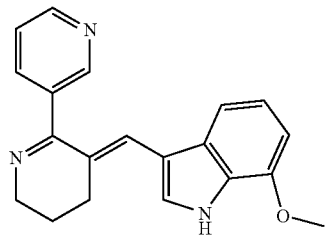

Yield: 60%. ¹H NMR (CD₃OD) δ 8.67 (m, 2H), 7.98 (m, 1H), 7.58 (m, 2H), 6.97 (m, 2H), 6.78 (m, 1H), 6.68 (m, 1H), 3.95 (s, 3H), 3.75 (m, 2H), 2.85 (m, 2H), 1.95 (m, 2H); MS (EI) m/z 318 (M⁺+1).

Example 23

3-(4-Methoxy-1H-indol-3-ylmethylene)-3,4,5,6-tetrahydro[2,3']bipyridinyl from 4-methoxyindole-3-carbaldehyde

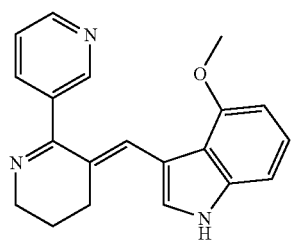

Yield: 55%. ¹H NMR (CDCl₃) δ 8.84 (m, 1H), 8.68 (m, 1H), 7.88 (m, 1H), 7.70 (m, 1H), 7.37 (m, 2H), 7.13 (m, 1H), 6.98 (m, 1H), 6.49 (m, 1H), 3.85 (m, 2H), 3.74 (s, 3H), 2.76 (m, 2H), 1.92 (m, 2H); MS (EI) m/z 318 (M$^+$+1).

Example 24

3-(5,6-Dihydro-4H-[2,3']-bipyridinyl-3-ylidenemethyl)-9-methyl-9H-carbazole from 9-methyl-9H-carbazole-3-carbaldehyde

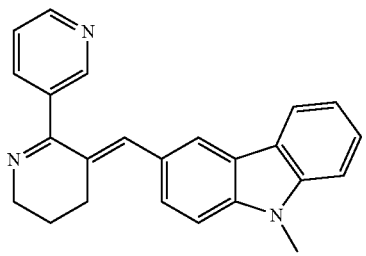

Yield: 40%. $^1$H NMR (CD$_3$OD) δ 9.20 (m, 2H), 8.77 (m, 1H), 8.51 (m, 1H), 8.24 (m, 1H), 8.15 (m, 1H), 7.85 (m, 1H), 7.63 (m, 4H), 7.32 (m, 1H), 3.97 (m, 4H), 3.32 (m, 2H), 3.09 (m, 2H), 2.28 (m, 2H); MS (EI) m/z 352 (M$^+$+1).

Example 25

3-(6-Methoxy-1H-indol-3-ylmethylene)-3,4,5,6-tetrahydro[2,3']bipyridinyl from 6-methoxyindole-3-carbaldehyde

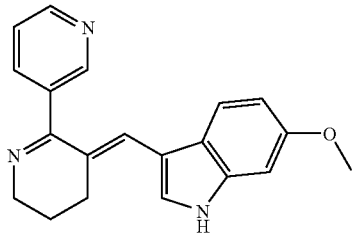

Yield: 60%. $^1$H NMR (DMSO-d$_6$) δ 8.64 (m, 2H), 7.86 (m, 1H), 7.56 (m, 1H), 7.47 (m, 1H), 7.10 (m, 1H), 6.89 (m, 1H), 6.67 (m, 1H), 6.64 (m, 1H), 3.74 (s, 3H), 3.68 (m, 2H), 3.74 (s, 3H), 2.71 (m, 2H), 1.77 (m, 2H); MS (EI) m/z 318 (M$^+$+1).

Example 26

3-(1H-Pyrrolo[2,3-b]pyridin-3-ylmethylene)-3,4,5,6-tetrahydro[2,3']bipyridinyl from 1H-pyrrolo[2,3-b]pyridin-3-carbaldehyde

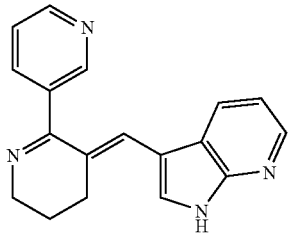

Yield: 35%. $^1$H NMR (CD$_3$OD) δ 8.67 (m, 2H), 8.24 (m, 1H), 7.97 (m, 1H), 7.75 (m, 2H), 7.57 (m, 1H), 7.13 (m, 1H), 6.88 (m, 1H), 3.78 (m, 2H), 2.88 (m, 2H), 1.94 (m, 2H); MS (EI) m/z 289 (M$^+$+1).

Example 27

3-(1H-Indazol-3-ylmethylene)-3,4,5,6-tetrahydro[2,3']bipyridinyl from 1H-indazol-3-carbaldehyde

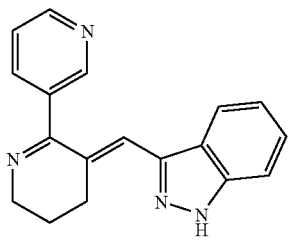

Yield: 45%. $^1$H NMR (DMSO-d$_6$) δ 8.65 (m, 2H), 7.90 (m, 1H), 7.55 (m, 1H), 7.48 (m, 2H), 7.35 (m, 1H), 7.10 (m, 1H), 6.81 (m, 1H), 3.76 (m, 2H), 3.13 (m, 2H), 1.75 (m, 2H); MS (EI) m/z 289 (M$^+$+1).

Example 28

3-(3H-Imidazol-4-ylmethylene)-3,4,5,6-tetrahydro[2,3']bipyridinyl from 3H-imidazole-4-carbaldehyde

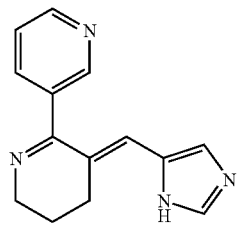

Yield: 55%. $^1$H NMR (CD$_3$OD) δ 8.77 (m, 1H), 8.72 (m, 1H), 8.02 (m, 1H), 7.86 (s, 1H), 7.65 (m, 2H), 6.96 (s, 1H), 3.83 (m, 2H), 3.01 (m, 2H), 2.07 (m, 2H); MS (EI) m/z 239 (M$^+$+1).

Example 29

3-(1-Methyl-1H-pyrrol-3-ylmethylene)-3,4,5,6-tetrahydro[2,3']bipyridinyl from 1-methyl-1H-pyrrole-3-carbaldehyde

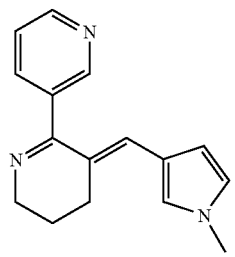

Yield: 40%. $^1$H NMR (CD$_3$OD) δ 8.61 (m, 2H), 7.87 (m, 1H), 7.52 (m, 1H), 6.92 (m, 1H), 6.69 (m, 1H), 6.48 (m, 1H), 6.24 (m, 1H), 3.70 (m, 2H), 3.67 (s, 3H), 2.79 (m, 2H), 1.90 (m, 2H); MS (EI) m/z 252 (M$^+$+1).

Example 30

3-(5-Fluoro-1H-indol-3-ylmethylene)-3,4,5,6-tetrahydro[2,3']bipyridinyl from 6-fluoroindole-3-carbaldehyde

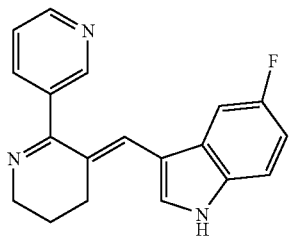

$^1$H NMR (CD$_3$OD) δ 8.68 (m, 2H), 7.98 (m, 1H), 7.73 (s, 1H), 7.60 (m, 1H), 7.39 (m, 1H), 6.89 (m, 2H), 3.75 (m, 2H), 2.87 (m, 2H), 1.95 (m, 2H); MS (EI) m/z 306 (M$^+$+1).

Example 31

3-(6-Methyl-1H-indol-3-ylmethylene)-3,4,5,6-tetrahydro-[2,3']bipyridinyl from 6-methyl-indole-3-carbaldehyde

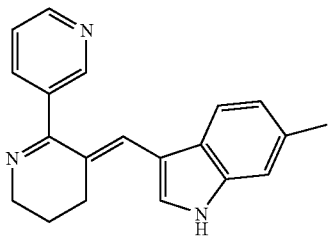

Yield: 55%. $^1$H NMR (CD$_3$OD) δ 8.68 (m, 2H), 7.98 (m, 1H), 7.60 (m, 2H), 7.20 (s, 1H), 7.11 (d, J=6.0 Hz, 1H), 6.89 (s, 1H), 6.86 (m, 1H), 3.76 (m, 2H), 2.85 (m, 2H), 2.41 (s, 3H), 1.95 (m, 2H); MS (EI) m/z 302 (M$^+$+1).

Example 32

3-(7-Methyl-1H-indol-3-ylmethylene)-3,4,5,6-tetrahydro[2,3']bipyridinyl from 7-methylindole-3-carbaldehyde

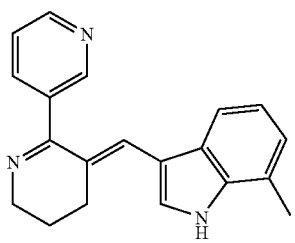

Yield: 55%. $^1$H NMR (CD$_3$OD) δ 8.67 (m, 2H), 7.98 (m, 1H), 7.65 (s, 1H), 7.59 (m, 1H), 7.06 (m, 1H), 6.95 (m, 3H), 3.77 (m, 2H), 2.88 (m, 2H), 2.50 (s, 3H), 1.96 (m, 2H); MS (EI) m/z 302 (M$^+$+1).

Example 33

3-(5-Benzyloxy-1H-indol-3-ylmethylene)-3,4,5,6-tetrahydro[2,3']bipyridinyl from 6-benzyloxyindole-3-carbaldehyde

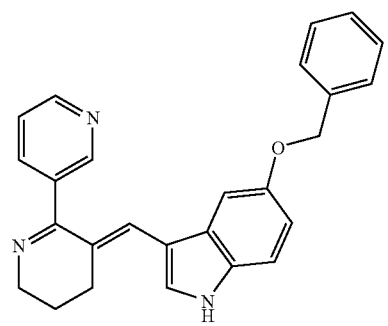

Yield: 50%. $^1$H NMR (CD$_3$OD) δ 8.70 (m, 2H), 7.95 (m, 1H), 7.61 (m, 2H), 7.32 (m, 6H), 6.91 (m, 2H), 6.73 (m, 1H), 5.01 (s, 2H), 3.75 (m, 2H), 2.83 (m, 2H), 1.94 (m, 2H); MS (EI) m/z 394 (M$^+$+1).

Example 34

3-(2-Methyl-5-nitro-1H-indol-3-ylmethylene)-3,4,5,6-tetrahydro-[2,3']bipyridinyl from 2-methyl-6-nitroindole-3-carbaldehyde

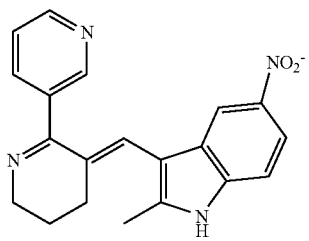

Yield: 40%. $^1$H NMR (CD$_3$OD) δ 8.86 (m, 1H), 8.65 (m, 1H), 8.28 (m, 1H), 8.04 (m, 2H), 7.56 (m, 1H), 7.42 (m, 1H), 6.73 (s, 1H), 3.91 (m, 2H), 2.69 (m, 2H), 1.94 (m, 2H); MS (EI) m/z 347 (M$^+$+1).

Example 35

7-(5,6-Dihydro-4H-[2,3']bipyridinyl-3-ylidenemethyl)-4-methyl-3,4-dihydro-2H-benzo[1,4]oxazine from 4-methyl-3,4-dihydro-2H-benzo[1,4]oxazine-7-carbaldehyde

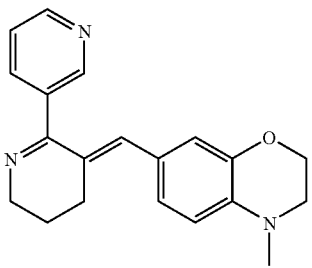

Yield: 62%. $^1$H NMR (CDCl$_3$) δ 8.72-8.61 (m, 2H), 7.80-7.77 (m, 1H), 7.32-7.24 (m, 1H), 6.84-6.47 (m, 4H), 4.29-4.24 (m, 2H), 3.84-3.81 (m, 2H), 3.33-3.28 (m, 2H), 2.92-2.81 (s, 5H), 1.84-1.78 (m, 2H); MS (EI) m/z 320 (M$^+$+1).

Example 36

3-(5,6-Dihydro-4H-[2,3']bipyridinyl-3-ylidenemethyl)-10-methyl-10H-phenothiazine from 10-methyl-10H-phenothiazine-3-carbaldehyde

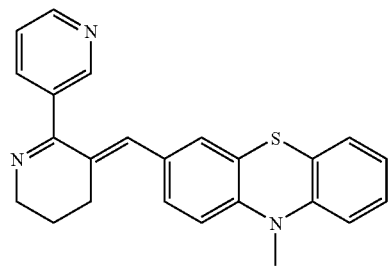

Yield: 55%. $^1$H NMR (CDCl$_3$) δ 8.72 (m, 1H), 8.64-8.62 (m, 1H), 7.82-7.79 (m, 1H), 7.35-7.31 (m, 1H), 7.20-7.09 (m, 4H), 6.94 (t, J=7.4, 1H), 6.83-6.76 (m, 2H), 6.51 (s, 1H), 3.86 (t, J=5.5, 2H), 3.38 (s, 3H), 2.85-2.80 (m, 2H), 1.87-1.79 (m, 2H); MS (EI) m/z 384 (M$^+$+1).

Example 37

3-[4-(4-Methylpiperazin-1-yl)benzylidene]-3,4,5,6-tetrahydro[2,3']bipyridinyl from 4-(4-methylpiperazin-1-yl)benzaldehyde

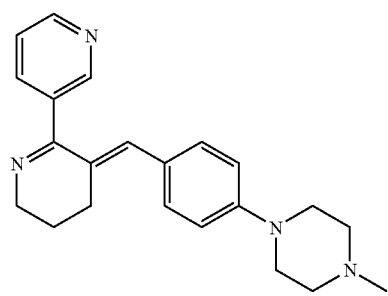

Yield: 28%. $^1$H NMR (CDCl$_3$) δ 8.73-8.61 (m, 2H), 7.80-7.44 (m, 1H), 7.32-7.21 (m, 3H), 6.91-6.85 (m, 2H), 6.55 (s, 1H), 3.84-3.81 (m, 2H), 3.29-3.25 (m, 4H), 2.85-2.84 (m, 2H), 2.59-2.54 (m, 4H), 2.35 (s, 3H), 1.83-1.79 (m, 2H); MS (EI) m/z 347 (M$^+$+1).

Example 38

3-(4-Morpholin-4-yl-benzylidene)-3,4,5,6-tetrahydro[2,3']bipyridinyl from 4-morpholin-4-ylbenzaldehyde

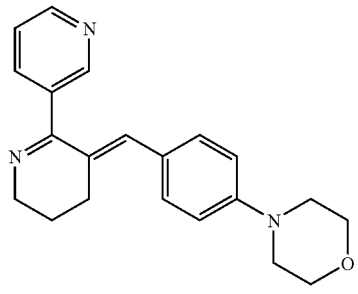

Yield: 55%. $^1$H NMR (CDCl$_3$) δ 8.73-8.62 (m, 2H), 7.35-7.24 (m, 3H), 6.89-6.85 (m, 2H), 6.56 (s, 1H), 3.87-3.84 (m, 6H), 3.23-3.19 (m, 4H), 2.86-2.84 (m, 2H), 1.85-1.82 (m, 2H); MS (EI) m/z 334 (M$^+$+1).

Example 39

3-(1H-Benzimidazol-5-ylmethylene)-3,4,5,6-tetrahydro[2,3']bipyridinyl from 1H-benzimidazole-5-carbaldehyde

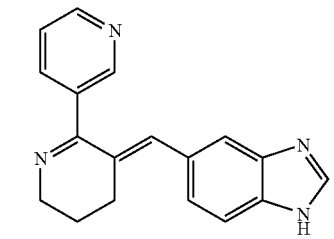

Aldehyde Preparation:

The aldehyde was prepared according to: Talaty, C. N.; Zenker, N.; Callery, P. S. *J. Heterocyclic Chem.* 1976, 13, 1121. Data: $^1$H NMR (DMSO-d$_6$) δ 12.89 (bs, 1H), 10.02 (s, 1H), 8.43 (s, 1H), 8.17 (m, 1H), 7.73 (m, 2H).

Condensation:

According to representative procedure A. Data: Yield: 45%. $^1$H NMR (CDCl$_3$) δ 8.86-8.85 (m, 1H), 8.77-8.75 (m, 1H), 8.18 (s, 1H), 8.01 (dt, J=8.5, 1.9, 1H), 7.75-7.72 (m, 2H), 7.56-7.52 (m, 1H), 7.35-7.32 (m, 1H), 6.92 (s, 1H), 4.00 (t, J=5.5, 2H), 3.06-3.02 (m, 2H), 2.82-2.76 (bs, 1H), 2.01-1.94 (m, 2H); MS (EI) m/z 289 (M$^+$+1).

Example 40

[5-(5,6-Dihydro-4H-[2,3']bipyridinyl-3-ylidenemethyl)benzofuran-2-yl]phenylmethanone from 2-benzoylbenzofuran-5-carbaldehyde

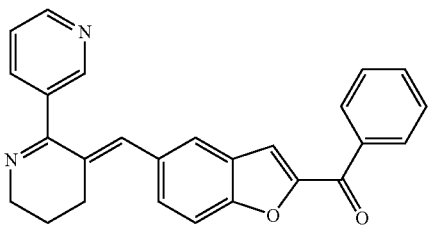

Yield: 23%. $^1$H NMR (CDCl$_3$) δ 8.78 (d, J=1.3, 1H), 8.66 (m, 1H), 8.05 (d, J=7.1, 1H), 8.04 (d, J=1.4, 1H), 7.86 (dt, J=7.8, 1.9, 1H), 7.68-7.52 (m, 6H), 7.42 (dd, 1H, J=8.7, 1.6), 7.36 (dd, 1H, 7.6, 4.9), 6.77 (s, 1H), 3.92 (t, J=5.5, 2H), 2.90-2.85 (m, 2H), 1.90-1.82 (m, 2H); MS (EI) m/z 393 (M$^+$+1).

Example 41

6-(5,6-Dihydro-4H-[2,3']bipyridinyl-3-ylidenemethyl)chromen-2-one from 2-oxo-2H-chromene-6-carbaldehyde

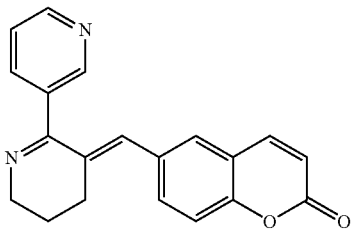

Yield: 31%. $^1$H NMR (CDCl$_3$) δ 8.76 (d, J=1.6, 1H), 8.66 (dd, J=4.9, 1.6, 1H), 7.84 (dt, J=7.8, 1.9, 1H), 7.68 (d, J=9.5, 1H), 7.49-7.32 (m, 4H), 6.66 (s, 1H), 6.46 (d, J=9.6, 1H), 3.92 (t, J=5.6, 2H), 2.86-2.81 (m, 2H), 1.90-1.82 (m, 2H); MS (EI) m/z 317 (M$^+$+1).

Example 42

5-(5,6-Dihydro-4H-[2,3']bipyridinyl-3-ylidenemethyl)-1,3-dihydrobenzimidazol-2-one from 2-oxo-2,3-dihydro-1H-benzimidazole-5-carbaldehyde

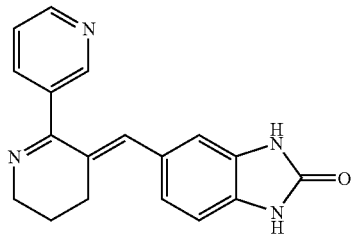

Aldehyde Preparation:

The aldehyde was prepared according to: Schmidt, G.; Zeiler, H.-J.; Metzger, K. G. U.S. Pat. No. 4,748,163 (May 31, 1998). Data: $^1$H NMR (DMSO-d$_6$) δ 11.05 (bs, 1H), 10.88 (bs, 1H), 9.78 (s, 1H), 7.63 (d, J=8.2, 1H), 7.36 (s, 1H), 7.01 (d, J=8.2, 1H).

Condensation:

According to representative procedure A. Data: Yield: 37%. $^1$H NMR (CDCl$_3$/CD$_3$OD) δ 10.67 (bm, 2H), 8.62-8.59 (m, 2H), 7.84 (m, 1H), 7.45-7.41 (m, 1H), 6.96-6.92 (m, 3H), 6.54 (s, 1H), 3.72 (t, J=5.3, 2H), 2.80-2.77 (m, 2H), 1.75-1.69 (m, 2H); MS (EI) m/z 305 (M$^+$+1).

Example 43

3-(1H-Benztriazol-5-ylmethylene)-3,4,5,6-tetrahydro[2,3']bipyridinyl from 1H-benztriazole-5-carbaldehyde

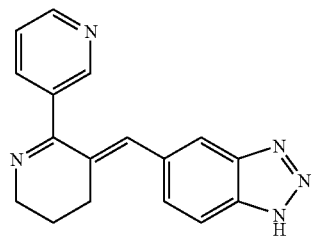

Aldehyde Preparation:

The aldehyde was prepared according to: Schmidt, G.; Zeiler, H.-J.; Metzger, K. G. U.S. Pat. No. 4,748,163 (May 31, 1998). Data: $^1$H NMR (DMSO-d$_6$) δ 10.17 (s, 1H), 8.64 (s, 1H), 8.03 (d, J=8.5, 1H), 7.91 (dd, J=8.4, 1.1, 1H).

Condensation:

According to representative procedure A. Data: Yield: 20%. $^1$H NMR (CDCl$_3$) δ 8.66-8.57 (m, 2H), 7.99-7.83 (m, 3H), 7.58-7.52 (m, 1H), 7.50-7.36 (m, 1H), 6.82 (s, 1H), 3.87-3.84 (m, 2H), 2.91-2.86 (m, 2H), 1.87-1.80 (m, 2H); MS (EI) m/z 290 (M$^+$+1).

Example 44

3-(2-Morpholin-4-ylbenzylidene)-3,4,5,6-tetrahydro[2,3']bipyridinyl from 2-morpholin-4-ylbenzaldehyde

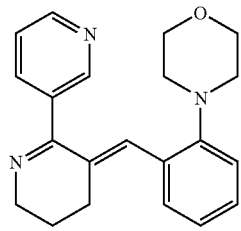

Yield: 14%. $^1$H NMR (CDCl$_3$) δ 8.64 (d, J=1.6, 1H), 8.58 (dd, J=4.9, 1.7, 1H), 7.71 (dt, J=7.8, 2.0, 1H), 7.29-7.20 (m, 4H), 7.00 (t, J=7.5, 1H), 6.92-6.90 (m, 1H), 6.74 (s, 1H), 3.86 (t, J=5.6, 2H), 3.51 (t, J=4.4, 4H), 2.76 (t, J=4.9, 6H), 2.82-2.64 (m, 2H), 1.76-1.72 (m, 2H); MS (EI) m/z 334 (M$^+$+1).

Example 45

3-(1H-Indazol-5-ylmethylene)-3,4,5,6-tetrahydro[2,3']bipyridinyl from 1H-indazole-5-carbaldehyde

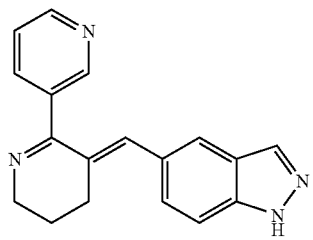

Aldehyde Preparation:

The aldehyde was prepared according to: DeLucca, G. V. U.S. Pat. No. 6,313,110 B1 (Nov. 6, 2001). Data: $^1$H NMR (CDCl$_3$) δ 9.91 (s, 1H), 8.25 (s, 1H), 8.17 (s, 1H), 7.83 (dd, J=8.5, 1.5, 1H), 7.60 (d, J=8.5, 1H).

Condensation:

According to representative procedure A. Data: Yield: 65%. $^1$H NMR (CDCl$_3$) δ 8.80 (d, J=1.7, 2H), 8.68-6.66 (m, 1H), 8.10 (s, 1H), 7.90-7.86 (m, 1H), 7.75 (s, 1H), 7.46-7.28

(m, 4H), 6.79 (s, 1H), 3.92 (t, J=5.6, 2H), 2.94-2.89 (m, 2H), 1.91-1.83 (m, 2H); MS (EI) m/z 289 (M$^+$+1).

Example 46

3-(1H-Indazol-6-ylmethylene)-3,4,5,6-tetrahydro[2,3']bipyridinyl from 1H-indazole-6-carbaldehyde

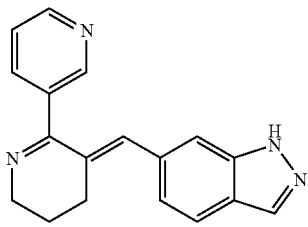

Aldehyde Preparation:

The aldehyde was prepared according to: DeLucca, G. V. U.S. Pat. No. 6,313,110 B1 (Nov. 6, 2001). Data: $^1$H NMR (CDCl$_3$) δ 10.15 (s, 1H), 8.20 (s, 1H), 8.05 (m, 1H), 7.91 (d, J=8.8, 1H), 7.70 (dd, J=8.7, 1.6, 1H)

Condensation:

According to representative procedure A. Data: Yield: 62%. $^1$H NMR (CDCl$_3$/CD$_3$OD) δ 8.81 (m, 1H), 8.73-8.70 (m, 1H), 7.87-7.77 (m, 2H), 7.54-7.50 (m, 1H), 7.19-7.16 (m, 1H), 6.88 (s, 1H), 3.98 (t, J=5.5, 2H), 3.03-2.98 (m, 2H), 2.10-1.95 (m, 2H); MS (EI) m/z 289 (M$^+$+1).

Example 47

3-(1H-Indazol-4-ylmethylene)-3,4,5,6-tetrahydro[2,3']bipyridinyl from 1H-indazol-4-carboxaldehyde

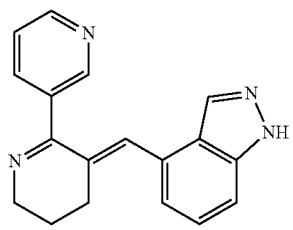

Aldehyde Preparation:

The aldehyde, 1H-indazol-4-carboxaldehyde, was prepared from 3-bromo-2-methylaniline according to the method described for examples 45 and 46: Data: $^1$H NMR (DMSO-d$_6$) δ 13.58 (s, 1H), 10.24 (s, 1H); 8.56 (s, 1H), 7.97 (d, J=8.5, 1H), 7.85 (dd, J=7.0, 1.0, 1H), 7.62 (dd, J=7.0, 1.5, 1H).

Condensation:

According to representative procedure A. Data: Yield: 76%. $^1$H NMR (CDCl$_3$) δ 8.87 (t, J=1.4, 1H), 8.67 (m, 1H), 7.93 (m, 1H), 7.88 (s, 1H), 7.36 (m, 3H), 7.13 (m, 1H), 7.02 (s, 1H) 3.95 (t, J=5.5, 2H), 2.82 (m, 2H), 1.83 (m, 2H); MS (EI) m/z 289 (M$^+$+1).

Example 48

3-[2-(4-Methylpiperazin-1-yl)benzylidene]-3,4,5,6-tetrahydro[2,3']bipyridinyl from 2-(4-methylpiperazin-1-yl)benzaldehyde

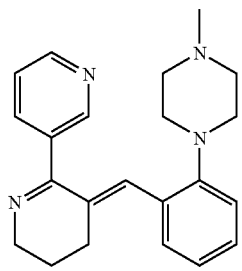

Yield: 45%. $^1$H NMR (CDCl$_3$) δ 8.74 (m, 1H), 8.66 (m, 1H), 7.80 (dt, J=7.9, 2.0, 1H), 7.37-7.27 (m, 4H), 7.08-6.98 (m, 2H), 6.81 (s, 1H), 3.94 (t, J=5.6, 2H), 2.89-2.81 (m, 6H), 2.27 (s, 3H), 1.89-1.78 (m, 2H); MS (EI) m/z 347 (M$^+$+1).

Example 49

6-(5,6-Dihydro-4H-[2,3']bipyridinyl-3-ylidenemethyl)-3H-benzoxazol-2-one from 3-hydroxy-4-nitrobenzaldehyde

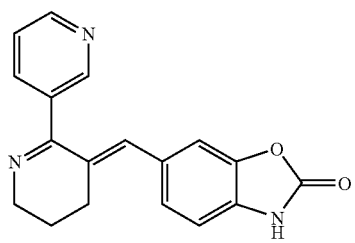

5-(5,6-Dihydro-4H-[2,3']bipyridinyl-3-ylidenemethyl)-2-nitrophenol was prepared by the condensation of anabasine and 3-hydroxy-4-nitrobenzaldehyde according to the representative procedure A. Data: $^1$H NMR (CDCl$_3$) δ 8.75 (d, J=1.7, 2H), 8.67 (dd, J=4.9, 1.6, 1H), 8.08 (d, J=8.8, 1H), 7.84 (dt, J=7.9, 1.9, 1H), 7.39-7.35 (m, 1H), 7.09 (d, J=1.7, 1H), 6.87 (dd, J=8.8, 1.8, 1H), 6.60 (s, 1H), 3.94 (t, J=5.6, 2H), 2.85-2.80 (m, 2H), 1.91-1.83 (m, 2H); MS (EI) m/z 310 (M$^+$+1). A suspension of the nitrophenol (47.2 mg, 0.153 mmol) and tin II chloride dihydrate (256 mg, 1.17 mmol, 7.7 eq) in ethanol (3.2 mL) was warmed to 60° C. 300 μL (0.0161 mmol, 0.11 eq) of a solution of sodium borohydride, prepared by dissolving 2 mg of the hydride in 1 mL of ethanol, was added over 10 min to the semi-suspension. After 2 h, the reaction mixture was allowed to cool to rt, was diluted with ethyl acetate (30 mL) and saturated potassium bicarbonate (30 mL), and was maintained for 1 h. The aqueous layer was extracted with ethyl acetate (20 mL) and dichloromethane (2×20 mL) and the combined organic layers were dried over sodium sulfate. The crude aminophenol (38.6 mg) was dissolved in dimethylformamide (3.2 mL), was treated with carbonyldiimidazole (26.9 mg, 0.166 mmol, 1.2 eq) and the reaction mixture was maintained for 16 h. The contents of the reaction were poured onto ½ saturated brine (50 mL) and extracted with ethyl acetate (2×20 mL) and dichloromethane (2×20 mL) and the combined organic layers were dried over sodium sulfate. The residue was purified by chromatography [0/1 to 1/3 ethyl acetate/(70/30/1 ethyl acetate/methanol/ammonium hydroxide)] to give 24.6 mg (53%) of the title compound as an orange solid. Data: $^1$H NMR (CDCl$_3$) δ 8.75 (s, 1H), 8.62 (m, 2H), 7.96-7.90 (m, 1H), 7.56-7.49 (m, 1H), 7.30-7.05 (m, 3H), 6.65-6.63 (m, 1H), 3.84-3.78 (m, 2H), 2.93-2.84 (m, 2H), 1.92-1.84 (m, 2H); MS (EI) m/z 306 (M$^+$+1).

Example 50

3-(4-Pyrrolidin-1-yl-benzylidene)-3,4,5,6-tetrahydro[2,3']bipyridinyl from 4-pyrrolidin-1-ylbenzaldehyde

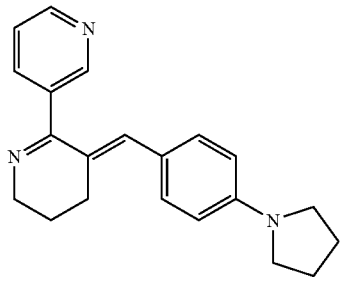

Yield: 44%. $^1$H NMR (CD$_3$Cl) δ 8.74-8.61 (m, 2H), 7.80 (m, 1H), 7.31-7.22 (m, 3H), 6.54-6.51 (m, 3H), 3.83-3.81 (m, 2H), 3.31-3.29 (m, 4H), 2.87-2.85 (m, 2H), 2.02-1.75 (m, 6H); MS (EI) m/z 318 (M$^+$+1).

Example 51

3-(3-Nitro-4-pyrrolidin-1-ylbenzylidene)-3,4,5,6-tetrahydro[2,3']bipyridinyl from 3-nitro-4-pyrrolidin-1-ylbenzaldehyde

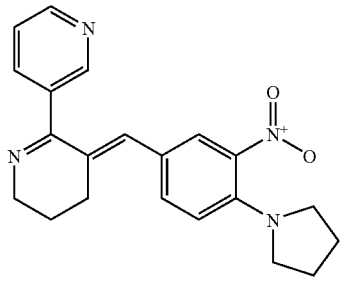

Yield: 39%. $^1$H NMR (CDCl$_3$) δ 8.73 (dd, J=2.1, 0.7, 1H), 8.64 (dd, J=4.9, 1.7, 1H), 7.81 (dt, J$_d$=7.8, J$_t$=2.1, 1H), 7.77 (d, J=2.1, 1H), 7.32 (m, 2H), 6.87 (d, J=8.9, 1H), 6.51 (s, 1H), 3.86 (t, J=5.5, 2H), 3.25 (m, 4H), 2.85 (m, 2H), 2.00 (m, 5H), 1.85 (m, 2H); MS (EI) m/z 363 (M$^+$+1).

Example 52

3-(3-Amino-4-pyrrolidin-1-ylbenzylidene)-3,4,5,6-tetrahydro[2,3']bipyridinyl from 3-nitro-4-pyrrolidin-1-ylbenzaldehyde

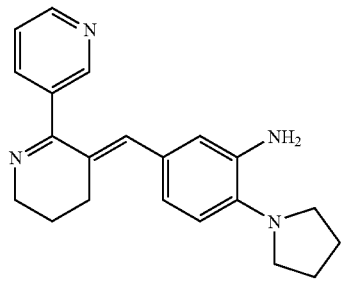

Tin (II) chloride dihydrate (1.32 g, 5.85 mmol, 7.5 eq) was added to a solution of the nitro amine (282 mg, 0.778 mmol) in ethanol (14 mL) and the slurry was warmed to 60° C. A solution of sodium borohydride in ethanol (2 mg/mL, 1.5 mL, 0.079 mmol, 0.1 eq) was added dropwise over 10 min to the solution and the reaction mixture was maintained for 2 h at 60° C. Upon cooling, the reaction mixture was poured onto saturated, aqueous sodium carbonate (25 mL) and ethyl acetate (25 mL) and maintained overnight with vigorous stiffing. The layers were separated and the aqueous layer extracted with ethyl acetate (2×25 mL). The combined organic layers were dried (sodium sulfate) and concentrated. The residue was purified by chromatography [1/0 to 4/1 to 1/1 ethyl acetate/(70/30/1 ethylacetate/methanol/ammonium hydroxide)] to provide 102 mg (39%) of the amine as an oil. Data: $^1$H NMR (CDCl$_3$) δ 8.73 (d, J=1.5, 1H), 8.62 (dd, J=4.8, 1.7, 1H), 7.80 (dt, J$_d$=7.8, J$_t$=1.9, 1H), 7.31 (ddd, J=8.4, 4.8, 0.7, 1H), 6.92 (d, J=8.1, 1H), 6.72 (m, 2H), 6.53 (s, 1H), 3.85 (t, J=5.5, 2H), 3.82 (bs, 1H), 3.09 (m, 4H), 2.86 (m, 2H), 1.93 (m, 4H), 1.83 (m, 2H); MS (EI) m/z 333 (M$^+$+1).

Example 53

3-(3-Amino-4-piperidin-1-ylbenzylidene)-3,4,5,6-tetrahydro[2,3']bipyridinyl from 3-nitro-4-piperidin-1-ylbenzaldehyde

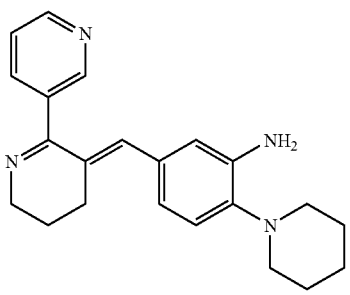

Yield: 51%. $^1$H NMR (CDCl$_3$) δ 8.73 (t, J=1.5, 1H), 8.62 (dd, J=4.9, 1.7, 1H), 7.80 (dt, J$_d$=7.8, J$_t$=1.9, 1H), 7.31 (ddd, J=7.8, 4.9, 0.8, 1H), 6.94 (d, J=8.0, 1H), 6.71 (m, 2H), 6.53 (s, 1H), 3.94 (bs, 1H), 3.85 (t, J=5.5, 2H), 2.86 (m, 6H), 1.82 (m, 2H), 1.70 (m, 5H), 1.59 (m, 2H); MS (EI) m/z 347 (M⁺+1).

Example 54

3-(3-Amino-4-morpholin-4-ylbenzylidene)-3,4,5,6-tetrahydro[2,3']bipyridinyl from 3-nitro-4-morpholin-4-ylbenzaldehyde

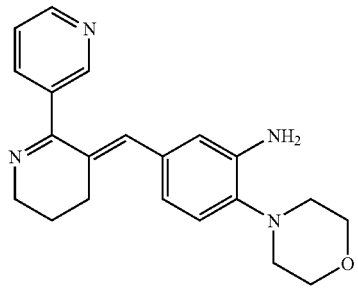

Yield: 68%. ¹H NMR (CDCl₃) δ 8.73 (s, 1H), 8.63 (d, J=3.7, 1H), 7.81 (dt, J$_d$=7.8, J$_t$=1.9, 1H), 7.32 (dd, J=7.5, 4.9, 1H), 6.96 (d, J=8.1, 1H), 6.72 (m, 2H), 6.54 (s, 1H), 3.95 (bs, 2H), 3.86 (m, 6H), 2.93 (m, 4H), 2.85 (m, 2H), 1.82 (m, 2H); MS (EI) m/z 348 (M⁺+1).

Example 55

3-(5-Chloro-1H-indol-3-ylmethylene)-3,4,5,6-tetrahydro[2,3']bipyridinyl dihydrochloride from 5-chloro-1H-indol-3-carboxaldehyde

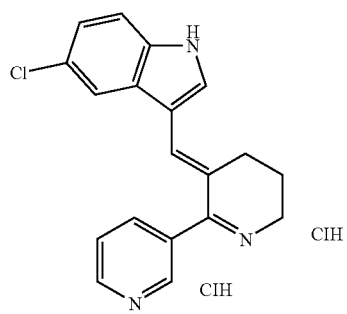

¹H NMR (DMSO-d₆) δ 8.96 (d, J=4.8, 1H), 8.92 (s, 1H), 8.36 (m, 1H), 8.22 (m, 1H), 7.81 (m, 1H), 7.59 (m, 1H), 7.54 (m, 2H), 7.24 (m, 1H), 3.78 (m, 2H), 2.91 (m, 2H), 2.10 (m, 2H); MS (EI) m/z 322 (M⁺+1).

Example 56

3-(3-Piperidin-1-ylbenzylidene)-3,4,5,6-tetrahydro[2,3']bipyridinyl from 3-piperidin-1-ylbenzaldehyde

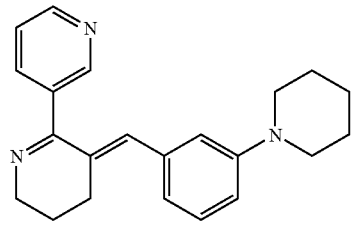

Yield: 44%. ¹H NMR (CDCl₃) δ 8.75 (t, J=1.4, 1H), 8.64 (dd, J=4.9, 1.7, 1H), 7.85 (dt, J$_d$=7.8, J$_t$=2.1, 1H), 7.29 (m, 3H), 6.88 (m, 1H), 6.74 (m, 2H), 6.65 (s, 1H), 3.88 (m, 2H), 3.14 (m, 3H), 2.85 (m, 2H), 1.84 (m, 2H), 1.67 (m, 3H), 1.61 (m, 3H); MS (EI) m/z 332 (M⁺+1).

Example 57

3-(Benzothiazol-5-ylmethylene)-3,4,5,6-tetrahydro[2,3']bipyridinyl from benzothiazol-5-carboxaldehyde

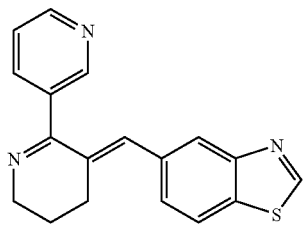

Aldehyde Preparation:

To a solution of 4-chloro-3-nitrobeznoic acid (20 g, 99.2 mmol, 1.0 eq) in dimethylformamide (400 mL) was added potassium carbonate (35 g, 254 mmol, 2.55 eq). The mixture was stirred 30 min and ethyl iodide (18.6 g, 119 mmol, 1.20 eq) was added. The reaction mixture was stirred at 50° C. for 4 h. Water (3 L) was added and the mixture was extracted with diethyl ether (2×500 mL). The organic extracts were combined, washed with brine (1 L), dried over anhydrous sodium sulfate and concentrated. The residue was crystallized from hexanes to provide 19.7 g (86%) of the ester. Data: ¹H NMR (500 MHz, CDCl₃) δ 8.51 (d, 1H), 8.17 (dd, 1H), 7.65 (d, 1H), 4.43 (q, 2H), 1.42 (t, 3H). Sulfur (1.60 g, 49.9 mmol, 0.58 eq) was dissolved in a solution of sodium sulfide nonahydrate (12.0 g, 50.0 mmol, 0.58 eq) in water (60 mL). This solution was combined with a solution of ethyl 4-chloro-3-nitrobenzoate (19.6 g, 85.4 mmol, 1.00 eq) in ethanol (100 mL). The resulting mixture was heated at reflux for 3 h. The hot reaction mixture was poured into water (600 mL) and stirred for 15 min. The product was isolated by filtration and recrystallized from ethanol to provide 16.45 g (77%) of the disulfide. Data: ¹H NMR (500 MHz, CDCl₃) δ 8.96 (d, 1H), 8.19 (dd, 1H), 7.88 (d, 1H), 4.43 (q, 2H), 1.41 (t, 3H). A mixture of diethyl 4,4'-dithiobis(3-nitrobenzoate) (11.2 g, 24.75 mmol, 1.00 eq) and zinc granules (15.0 g, 234 mmol, 9.47 eq) in formic acid (600 mL) was heated to reflux for 48 h. The mixture was cooled to room temperature and concentrated to dryness on vacuum rotary evaporator. The residue was partitioned between ethyl acetate (500 mL) and saturated aqueous sodium bicarbonate (500 mL). The organic layer was separated, dried over anhydrous sodium sulfate and concentrated on vacuum rotary evaporator. The residue was purified by chromatography on neutral Alumina (1/0 to 0/1 hexanes/dichloromethane) to provide 5.30 g (51%) of the benzthiazole ester. Data: $^1$H NMR (500 MHz, CDCl$_3$) δ 9.08 (s, 1H), 8.83 (d, 1H), 8.14 (dd, 1H), 8.02 (d, 1H), 4.45 (q, 2H), 1.44 (t, 3H); MS (EI) m/z 208 (M$^+$+1). Diisobutylaluminum hydride (1.0 M in dichloromethane, 6.0 mL, 6 mmol, 1.05 eq) was added over 15 min to a solution of the ester (1.18 g, 5.70 mmol) in dichloromethane (40 mL) at −35° C. The reaction mixture was allowed to warm to rt and was maintained overnight. Analysis of the reaction progress by thin layer chromatography revealed the presence of starting material. The reaction mixture was cooled to 0° C. and was treated with additional diisobutylaluminum hydride (6.0 mL, 6 mmol). After 4 h at rt, the reaction was quenched by the addition of water (10 mL) and the slurry was poured onto 5% sodium hydroxide and dichloromethane (200 mL) and maintained for 30 min with vigorous stirring. The organic layer was separated, washed with brine, dried (sodium sulfate), and concentrated. The residue was dissolved in dichloromethane (100 mL) and was treated with manganese (IV) oxide (3.0 g) and powdered 4 Å seives (3.0 g). The reaction mixture was filtered through Celite (100 mL dichloromethane rinse) after 14 h and the filtrate was extracted with 0.6 N aqueous sodium hydrogen sulite (2×150 mL). The combined aqueous layers were back-extracted with dichloromethane (50 mL), were made basic (pH 11) by the addition of 50% sodium hydroxide, and were extracted with ethyl acetate (2×100 mL). The ethyl acetate layers were dried (sodium sulfate) and concentrated to provide 268 mg (29%) of the aldehyde as a tan solid. Data: $^1$H NMR (CDCl$_3$) δ 10.18 (s, 1H), 9.13 (s, 1H), 8.61 (d, J=1.0, 1H), 8.11 (d, J=8.0, 1H), 8.01 (dd, J=8.5, 1.5, 1H).

Condensation:

According to procedure A. Data: Yield: 86%. $^1$H NMR (CD$_3$OD) δ 8.97 (s, 1H), 8.75 (s, 1H), 8.60 (s, 1H), 8.06 (d, J=0.6, 1H), 7.87 (d, J=8.4, 1H), 7.82 (dt, J$_d$=7.8, J$_t$=1.8, 1H), 7.30 (dd, J=7.8, 4.8, 1H), 7.26 (dd, J=8.4, 1.6, 1H), 6.76 (s, 1H), 3.86 (t, J=5.5, 2H), 2.85 (m, 2H), 1.79 (m, 2H); MS (EI) m/z 306 (M$^+$+1).

Example 58

3-(Benzothiazol-6-ylmethylene)-3,4,5,6-tetrahydro [2,3']bipyridinyl from Benzothiazol-6-carboxaldehyde

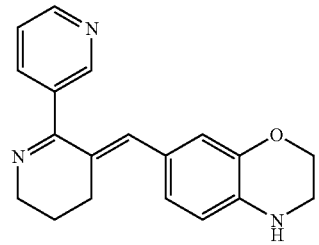

Aldehyde Preparation:

According to preparation detailed in example 57 from 3-chloro-4-nitrobenzoic acid. Data: $^1$H NMR (CDCl$_3$) δ 10.16 (s, 1H), 9.22 (s, 1H), 8.52 (d, J=1.5, 1H), 8.27 (d, J=8.5, 1H), 8.05 (dd, J=8.5, 1.5, 1H).

Condensation:

According to procedure A. Data: Yield: 63%. $^1$H NMR (CDCl$_3$) δ 9.02 (s, 1H), 8.78 (bs, 1H), 8.65 (bs, 1H), 8.10 (d, J=8.5, 1H), 7.91 (s, 1H), 7.86 (dt, J$_d$=7.8, J$_t$=1.9, 1H), 7.44 (dd, J=8.6, 1.5, 1H), 7.36 (dd, J=7.7, 4.8, 1H), 6.79 (s, 1H), 3.92 (t, J=5.7, 2H), 2.89 (m, 2H), 1.90 (m, 2H); MS (EI) m/z 306 (M$^+$+1).

Example 59

3-(3,4-Dihydro-2-benzo[1,4]oxazin-7-ylmethylene)-3,4,5,6-tetrahydro[2,3']bipyridinyl from 3,4-dihydro-2H-benzo[1,4]oxazin-7-carboxaldehyde

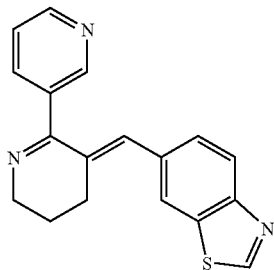

Aldehyde Preparation:

The phenol, 5-[1,3]dioxan-2-yl-2-nitrophenol, used as a starting material was prepared from 4-nitro-3-hydroxybenzaldehyde according to: Belliotti, T. R.; Wustrow, D. J.; Brink, W. A.; Zoski, K. T.; Shih, Y.-H.; Whetzel, S. Z.; Georgic, L. M.; Corbin, A. E.; Akunne, H. C.; Heffner, T. G.; Pugsley, T. A.; Wise, L. D. *J. Med. Chem.* 1999, 42, 5181. To a solution of the phenol (2.55 g, 11.3 mmol) in dimethylformamide (20 mL) was added potassium carbonate (2.56 g, 18.5 mmol, 1.6 eq) and ethyl bromoacetate (1.5 mL, 14 mmol, 1.2 eq). The reaction mixture was maintained for 18 h at rt and was poured onto ½ saturated brine and extracted with ethyl acetate (3×60 mL). The combined organic layers were washed with water and brine, were dried over sodium sulfate, and were concentrated to provide (5-[1,3]dioxan-2-yl-2-nitrophenoxy)acetic acid ethyl ester as a gold oil. The ester was dissolved in ethanol (63 mL) and was treated with a solution of calcium chloride (1.42 g, 9.66 mmol) in water (19 mL) and with zinc dust (11.0 g, 16.8 mmol). The grey suspension was heated at 100° C. for 3 h and was filtered (hot) through Celite (ethyl acetate wash). The filtrate was concentrated to approximately 25 mL and the slurry was transferred to a separatory funnel containing ethyl acetate (200 mL). The organic layer was separated and concentrated to provide 2.19 g of 6-[1,3] dioxan-2-yl-3,4-dihydro-1H-quinolin-2-one as an oil that solidified upon standing. The amide (2.19 g, 9.31 mmol) was added in portions to a suspension of lithium aluminum hydride (576 mg, 14.2 mmol, 1.5 eq) in tetrahydrofuran (50 mL) over 15 min. The reaction mixture was maintained for 3 h at rt and was quenched with a saturated, aqueous solution of sodium potassium tartrate (10 mL). The resultant slurry was maintained overnight and was diluted with water (40 mL) and extracted with dichloromethane (3×30 mL). The combined organic layers were dried over sodium sulfate, concentrated, and the residue was purified by chromatography (1/1 hexane/ethyl acetate) to provide 1.17 g (57%) of 6-[1,3]dioxan-2-yl-1,2,3,4-tetrahydroquinoline as a 10/1 mixture of the acetal/aldehyde. This amine served as a starting material for examples 59, 61, and 62. A portion of the mixture (144 mg) was dissolved in dichloromethane (5 mL), diluted with 1 N hydrochloric acid (5 mL), and was maintained for 14 h with vigorous stirring. The reaction was neutralized with solid sodium carbonate, extracted with dichloromethane (3×10 mL), and the combined organic layers were dried over sodium sulfate and concentrated. The residue was purified by chromatography (4/1 to 2/1 hexane/ethyl acetate) to provide 87.1 mg (82%) of the aldehyde as a solid. Data: $^1$H NMR (CDCl$_3$) δ 9.61 (s, 1H), 7.24 (m, 2H), 6.60 (d, J=8.8, 1H), 4.39 (bs, 1H), 4.17 (t, J=4.3, 2H), 3.44 (t, J=4.4, 2H).

Condensation:

According to procedure A. Data: Yield: 85%. $^1$H NMR (CDCl$_3$) δ 8.72 (s, 1H), 8.62 (s, 1H), 7.80 (dt, $J_d$=7.8, $J_t$=1.8, 1H), 7.31 (dd, J=7.5, 4.7, 1H), 6.84 (d, J=1.9, 1H), 6.72 (dd, J=8.2, 1.8, 1H), 6.53 (d, J=8.2, 1H), 6.48 (s, 1H), 4.24 (m, 2H), 3.83 (m, 2H), 3.44 (m, 2H), 2.85 (m, 2H), 1.82 (m, 2H); MS (EI) m/z 306 (M$^+$+1).

Example 60

3-(3,4-Dihydro-2H-benzo[1,4]oxazin-7-ylmethylene)-3,4,5,6-tetrahydro[2,3']bipyridinyl trihydrochloride from 3,4-dihydro-2H-benzo[1,4]oxazin-7-carboxaldehyde

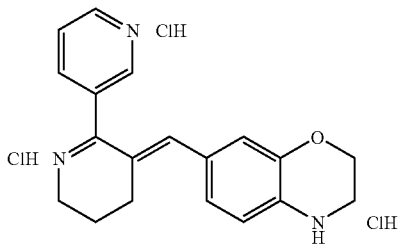

Yield: 75%. $^1$H NMR (CD$_3$OD) δ 9.28 (s, 1H), 9.18 (d, J=5.5, 1H), 8.87 (d, J=8.0, 1H), 8.35 (dd, J=8.0, 6.0, 1H), 7.23 (d, J=9.0, 1H), 7.18 (d, J=12, 2H), 6.76 (d, J=8.5, 1H), 5.50 (s, 1H), 4.21 (t, J=5.5, 2H), 3.87 (t, J=6.0, 2H), 3.54 (m, 2H), 3.11 (m, 2H), 2.21 (m, 2H); MS (EI) m/z 306 (M$^+$+1).

Example 61

3-(4-Cyclopropylmethyl-3,4-dihydro-2H-benzo[1,4]oxazin-7-ylmethylene)-3,4,5,6-tetrahydro[2,3']bipyridinyl from 3,4-dihydro-2H-benzo[1,4]oxazin-7-carboxaldehyde

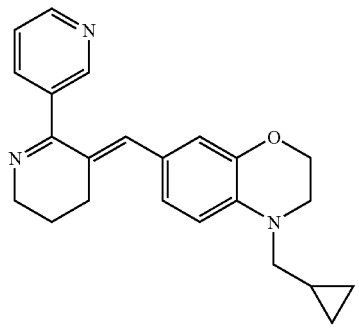

Aldehyde Preparation:

The amine from example 59 (338 mg, 1.53 mmol) was dissolved in dichloromethane (3.0 mL) and was treated with pyridine (0.19 mL, 2.3 mmol, 1.5 eq) and cycloproylcarbonyl chloride (0.17 mL, 1.9 mmol, 1.2 eq). After 3 h, the contents of the reaction were adsorbed onto a bed of silica gel and were purified by chromatography (1/1 hexane/ethyl acetate) to provide 481 mg of the tertiary amide. The amide (442 mg) was dissolved in tetrahydrofuran (8 mL) and was treated with lithium aluminum hydride (88.1 mg, 2.21 mmol). The reaction was quenched after 3 h with a saturated, aqueous solution of sodium potassium tartrate (10 mL) and the resultant slurry was extracted with dichloromethane (3×30 mL). The residue was dissolved in tetrahydrofuran (3 mL) and was diluted with 1 N hydrochloric acid (1 mL). After 6 h, the reaction mixture was neutralized with saturated potassium carbonate and extracted with dichloromethane (3×30 mL) and the combined organic layers were dried over sodium sulfate. The residue was purified by chromatography (3/7 hexane/ethyl acetate) to give 31.5 mg of the aldehyde as an inseparable mixture (2/1) of amine/amide. Data: $^1$H NMR (CDCl$_3$) δ 9.68 (s, 1H), 7.31 (m, 1H), 6.72 (m, 2H), 4.24 (m, 2H), 3.45 (m, 2H), 3.11 (m, 2H), 1.04 (m, 1H), 0.56 (m, 2H), 0.23 (m, 2H).

Condensation:

According to procedure A. Data: Yield: 19%. $^1$H NMR (CDCl$_3$) δ 8.72 (s, 1H), 8.61 (s, 1H), 7.79 (m, 1H), 7.29 (m, 1H), 6.77 (m, 3H), 6.48 (s, 1H), 4.24 (s, 2H), 3.82 (s, 2H), 3.46 (s, 2H), 3.16 (d, J=5.2, 2H), 2.86 (bs, 2H), 1.82 (bs, 2H), 1.26 (m, 1H), 0.56 (m, 2H), 0.21 (m, 2H); MS (EI) m/z 360 (M$^+$+1).

Example 62

3-(4-Ethyl-3,4-dihydro-2H-benzo[1,4]oxazin-7-ylmethylene)-3,4,5,6-tetrahydro[2,3']bipyridinyl from 3,4-dihydro-2H-benzo[1,4]oxazin-7-carboxaldehyde

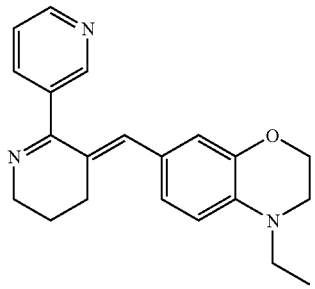

Aldehyde Preparation:

The amine from example 59 (160 mg, 0.723 mmol) was dissolved in tetrahydrofuran (4.5 mL) and was treated with sodium hydride (36 mg, 1.5 mmol). After 30 min, the reaction mixture was treated with iodoethane (0.15 mL, 1.9 mmol). The reaction was quenched with a water (10 mL) and the resultant slurry was extracted with dichloromethane (3×30 mL). The residue was dissolved in tetrahydrofuran (3 mL) and was diluted with 1 N hydrochloric acid (1 mL). After 2 h, the reaction mixture was neutralized with saturated potassium carbonate and extracted with dichloromethane (3×30 mL) and the combined organic layers were dried over sodium sulfate. The residue was purified by chromatography (3/7 hexane/ethyl acetate) to give 35.0 mg of the aldehyde. Data: $^1$H NMR (CDCl$_3$) δ 9.67 (s, 1H), 7.37 (dd, J=8.4, 1.9, 1H), 7.27 (d, J=1.8, 1H), 6.69 (d, J=8.4, 1H), 4.22 (t, J=4.4, 2H), 3.44 (m, 4H), 1.20 (t, J=7.1, 3H).

Condensation:

According to procedure A. Data: Yield: 86%. $^1$H NMR (CDCl$_3$) δ 8.73 (s, 1H), 8.61 (s, 1H), 7.80 (dt, J$_d$=7.8, J$_f$=1.9, 1H), 7.30 (dd, J=7.6, 4.8, 1H), 7.20 (m, 1H), 6.86 (d, J=2.0, 1H), 6.80 (dd, J=8.5, 2.0, 1H), 6.62 (d, J=8.4, 1H), 6.48 (s, 1H), 4.17 (m, 2H), 3.82 (t, J=5.4, 2H), 3.37 (m, 4H), 2.86 (m, 2H), 1.88 (m, 2H), 1.15 (t, J=7.0, 3H); MS (EI) m/z 334 (M$^+$+1).

Example 63

3-(1-Phenyl-1H-pyrrol-2-ylmethylene)-3,4,5,6-tetrahydro[2,3']bipyridinyl from 1-phenyl-1H-pyrrol-2-carboxaldehyde

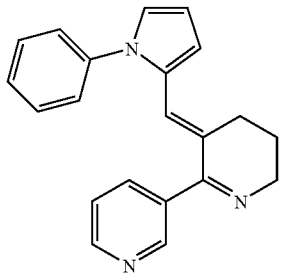

Yield: 6%. MS (EI) m/z 314 (M$^+$+1).

Example 64

3-[2-(5,6-Dihydro-4H-[2,3']bipyridinyl-3-ylidenemethyl)pyrrol-1-yl]benzonitrile from 1-(3-cyanophenyl)-1H-pyrrol-2-carboxaldehyde

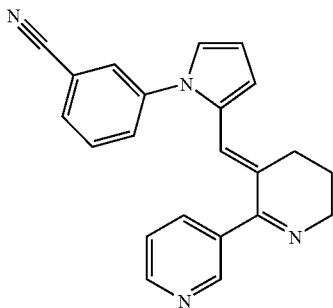

Yield: 22%. $^1$H NMR (CDCl$_3$) δ 8.50-8.48 (m, 1H), 8.43 (d, J=1.6, 1H), 7.76 (d, J=7.9, 1H), 7.69 (d, J=7.8, 1H), 7.58-7.54 (m, 2H), 7.49-7.48 (m, 1H), 7.42-7.40 (m, 1H), 7.12-7.11 (m, 1H), 6.79-6.78 (m, 1H), 6.45 (t, J=3.4, 1H), 6.18 (s, 1H), 3.77-3.73 (m, 2H), 2.87-2.83 (m, 2H), 1.93 (m, 2H); MS (EI) m/z 339 (M$^+$+1).

Example 65

3-(2-Cyclohexylmethyl-2H-pyrazol-3-ylmethylene)-3,4,5,6-tetrahydro[2,3']bipyridinyl from 2-cyclohexylmethyl-2H-pyrazole-3-carbaldehyde

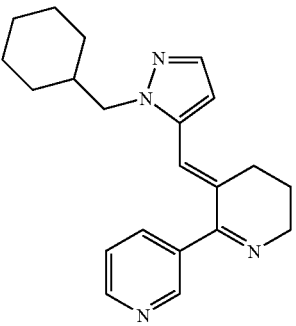

Aldehyde Preparation:

To a solution of pyrazole (1.00 g, 14.7 mmol) in of dimethylformamide (10 mL) was added sodium hydride (60% oil dispersion, 450 mg, 11 mmol). After 5 min, bromomethylcyclohexane (2.4 mL, 17 mmol) was added by syringe and the mixture was maintained overnight. The reaction mixture was quenched with methanol, diluted with water, and extracted with ether (2×). The combined organic layers were dried over magnesium sulfate and concentrated in vacuo. The residue was purified by chromatography (95/5 hexanes/ethyl acetate) to provide 500 mg (27%) of 1-cyclohexylmethyl-1H-pyrazole. To a solution of 1-cyclohexylmethyl-1H-pyrazole (490 mg, 3.00 mmol) in tetrahydrofuran (10 mL) at −78° C. was added a 2.5 M solution of n-butyllithium in hexanes (1.5 mL, 3.8 mmol). The reaction mixture was maintained at −78° C. for 1 h and was treated with dimethylformamide (1.0 mL, 13 mmol). The reaction mixture was allowed to warm to rt, maintained overnight, and was quenched with methanol. The reaction mixture was diluted with water and was extracted with ether (2×). The combined organic layers were dried over magnesium sulfate and concentrated in vacuo. The residue was purified by chromatography (95/5 hexanes/ethyl acetate) to provide 390 mg (68%) of 2-cyclohexylmethyl-2H-pyrazole-3-carbaldehyde.

Condensation:

According to procedure A. Data: Yield: 34%. $^1$H NMR (CDCl$_3$) δ 8.75 (d, J=1.4, 1H), 8.68-8.66 (m, 1H), 7.83-7.79 (m, 1H), 7.51 (d, J=1.6, 1H), 7.38-7.27 (m, 1H), 6.47-6.44 (m, 1H), 3.88 (t, J=5.6, 2H), 3.75 (d, J=7.2, 2H), 2.80-2.75 (m, 2H), 1.91-1.83 (m, 2H), 1.64-1.58 (m, 4H), 1.41-1.37 (m, 2H), 1.16-1.06 (m, 3H), 0.84-0.76 (m, 2H); MS (EI) m/z 335 (M$^+$+1).

Example 66

3-(2-Cyclopentyl-2H-pyrazol-3-ylmethylene)-3,4,5,6-tetrahydro[2,3']bipyridinyl from 2-cyclopentyl-2H-pyrazole-3-carbaldehyde

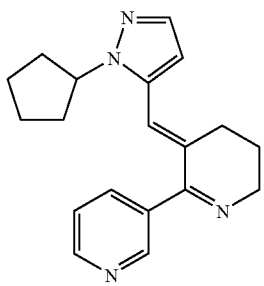

Aldehyde Preparation:

The aldehyde was prepared in a manner analogous to example 65.

Condensation:

According to representative procedure A. Data: Yield: 5%. MS (EI) m/z 307 (M$^+$+1).

Example 67

3-[1-(4-Chlorophenyl)-1H-pyrrol-2-ylmethylene]-3,4,5,6-tetrahydro[2,3']bipyridinyl from 1-(4-Chlorophenyl)-1H-pyrrol-2-carboxaldehyde

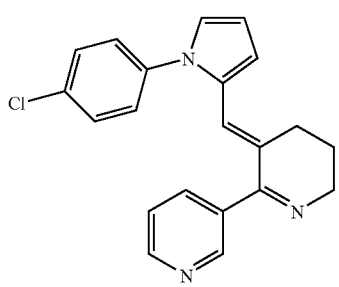

Yield: 2%. $^1$H NMR (MeOD) δ 8.50-8.48 (m, 1H), 8.44-8.43 (m, 1H), 7.73-7.70 (m, 1H), 7.39-7.33 (m, 3H), 7.15-7.10 (m, 2H), 7.07-7.06 (m, 1H), 6.76 (d, J=3.8, 1H), 6.43-6.41 (m, 1H), 6.18 (s, 1H), 3.76-3.72 (m, 2H), 2.87-2.82 (m, 2H), 1.95-1.86 (m, 2H); MS (EI) m/z 349 (M$^+$+1).

Example 68

3-[1-(4-Trifluoromethoxyphenyl)-1H-pyrrol-2-ylmethylene]-3,4,5,6-tetrahydro[2,3']bipyridinyl from 1-(4-trifluoromethoxy-phenyl)-1H-pyrrole-2-carbaldehyde

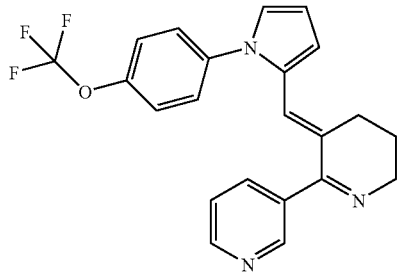

Yield: 6%. $^1$H NMR (CDCl$_3$) δ 8.45-8.43 (m, 2H), 7.76-7.72 (m, 1H), 7.36-7.24 (m, 5H), 7.11-7.09 (m, 1H), 6.79 (d, J=3.2, 1H), 6.45-6.43 (m, 1H), 6.21 (s, 1H), 3.77-3.73 (m, 2H), 2.89-2.84 (m, 2H), 1.94-1.88 (m, 2H); MS (EI) m/z 398 (M$^+$+1).

Representative Procedure B

Example 69

3-(4-piperazin-1-ylbenzylidene)-3,4,5,6-tetrahydro[2,3']bipyridinyl from 3-(4-iodobenzylidene)-3,4,5,6-tetrahydro[2,3']bipyridinyl

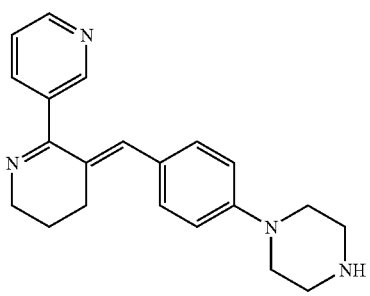

3-(4-Iodobenzylidene)-3,4,5,6-tetrahydro[2,3']bipyridinyl was prepared from anabaseine and 4-iodobenzaldehyde according to representative procedure A. Data: $^1$H NMR (CDCl$_3$) δ 8.61 (m, 2H), 7.92 (dd, J=7.2, 0.4, 1H), 7.73 (dd, J=8.8, 2, 2H), 7.52 (m, 1H), 7.12 (d, J=8.4, 2H), 6.56 (s, 1H), 3.82 (t, J=5.6, 2H), 2.84 (m, 2H), 1.85 (m, 2H); MS (EI) m/z 375 (M$^+$+1). In four 5 mL microwave reaction vessels was added the iodide (1.23 g, 3.29 mmol), 1-Boc-piperazine (835 mg, 4.48 mmol, 1.4 eq), tris(dibenzylideneacetone)dipalladium (0) (302 mg, 0.330 mmol, 0.1 eq), tri-tert-butylphosphine tetrafluoroborate (238 mg, 0.820 mmol, 0.25 eq), and sodium tert-butoxide (557 mg, 5.80 mmol, 1.8 eq). The vessel was evacuated, back-filled with argon gas, and the contents diluted with toluene (20 mL). The vessel was sealed and subjected to microwave irradiation at 160° C. for 300 s. The contents of the reaction were diluted with ethyl acetate (20 mL), were filtered through Celite (ethyl acetate wash), and were concentrated. The residue was purified by chromatography [1/0 to 4/1 ethyl acetate/(70/30/1 ethylacetate/methanol/ammonium hydroxide)] to provide a red oil. The oil was diluted with dichloromethane (10 mL) and treated with trifluoroacetic acid (5 mL). After 2 h, the contents of the reaction were added to a SCX column and was washed with methanol (50 mL). The product was eluted with 2 M ammonia in methanol to give 765 mg (70%) of the piperidine adduct as an oil. Data: $^1$H NMR (CD$_3$OD) δ 8.62 (broad s, 2H), 7.91 (m, 1H), 7.54 (m, 1H), 7.33 (d, J=8.8, 2H), 7.01 (d, J=8.9, 2H), 6.59 (s, 1H), 3.79 (m, 2H), 3.43 (m, 3H), 3.25 (m, 4H), 2.92 (m, 2H), 1.89 (m, 2H); MS (EI) m/z 333 (M$^+$+1).

Using this general procedure the following compounds were prepared:

Example 70

3-[4-(trans-2,5-Dimethylpiperazin-1-yl)benzylidene]-3,4,5,6-tetrahydro[2,3']bipyridinyl from 3-(4-iodobenzylidene)-3,4,5,6-tetrahydro[2,3']bipyridinyl

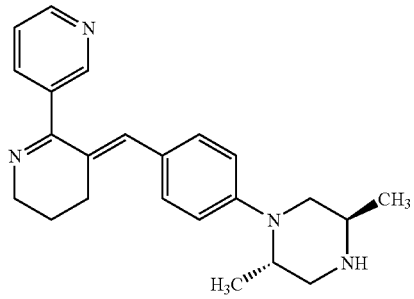

Yield: 24%. $^1$H NMR (CD$_3$OD) δ 8.61 (m, 2H), 7.91 (m, 1H), 7.53 (m, 1H), 7.31 (d, J=8.6, 2H), 7.11 (d, J=8.6, 2H), 6.57 (s, 1H), 3.80 (t, J=5.5, 2H), 3.11 (m, 4H), 2.89 (m, 2H), 2.61 (m, 2H), 1.57 (m, 2H), 1.09 (d, J=6.4, 3H), 0.94 (d, J=6.1, 3H); MS (EI) m/z 361 (M$^+$+1).

Example 71

3-[4-(cis-3,5-Dimethylpiperazin-1-yl)benzylidene]-3,4,5,6-tetrahydro[2,3']bipyridinyl from 3-(4-iodobenzylidene)-3,4,5,6-tetrahydro[2,3']bipyridinyl

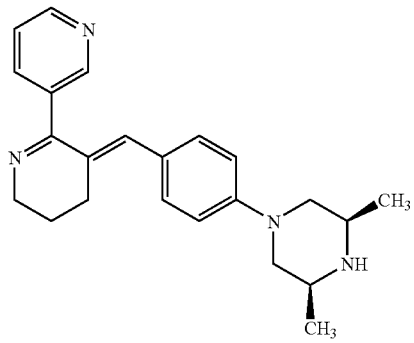

Yield: 76%. $^1$H NMR (CD$_3$OD) δ 8.60 (m, 2H), 7.89 (d, J=7.8, 1H), 7.52 (dd, J=7.8, 4.9, 1H), 7.27 (d, J=8.7, 2H), 6.95 (d, J=8.8, 2H), 6.51 (s, 1H), 3.77 (t, J=5.4, 1H), 3.69 (d, J=12.4, 2H), 2.98 (m, 2H), 2.90 (m, 2H), 2.33 (t, J=11.9, 2H), 1.86 (m, 2H), 1.16 (d, J=6.4, 6H); MS (EI) m/z 361 (M$^+$+1).

Example 72

3-(4-Thiomorpholin-4-ylbenzylidene)-3,4,5,6-tetrahydro[2,3']bipyridinyl from 3-(4-iodobenzylidene)-3,4,5,6-tetrahydro[2,3']bipyridinyl

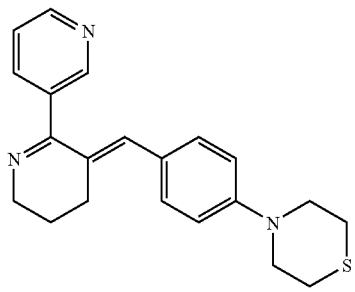

Yield: 91%. $^1$H NMR (CD$_3$OD) δ 8.61 (m, 2H), 7.90 (dt, J$_d$=7.9, J$_t$=1.8, 1H), 7.53 (ddd, J=7.8, 5.0, 0.8, 1H), 7.28 (d, J=8.9, 2H), 6.90 (d, J=9.0, 2H), 6.54 (s, 1H), 3.77 (t, J=5.4, 2H), 3.66 (m, 4H), 2.91 (m, 2H), 2.65 (m, 4H), 1.88 (m, 2H); MS (EI) m/z 350 (M$^+$+1).

Example 73

3-[4-(1-Oxo-1λ4-thiomorpholin-4-yl)-benzylidene]-3,4,5,6-tetrahydro-[2,3']bipyridinyl from 3-(4-thiomorpholin-4-ylbenzylidene)-3,4,5,6-tetrahydro[2,3'] bipyridinyl To a solution of the thio ether from example 72 (42.8 mg, 0.122 mmol) in dichloromethane (1 mL) was added m-chloroperoxybenzoic acid (63.0 mg, 0.281 mmol, 2.3 eq) After 15 h, the reaction mixture was poured onto saturated sodium bicarbonate (3 mL) and was extracted with dichloromethane (3×10 mL) and dried over sodium sulfate. The residue was purified by chromatography [3/7 ethyl acetate/(70/30/1 ethylacetate/methanol/ammonium hydroxide)] to provide 22.1 mg (49%) of the sulfoxide.

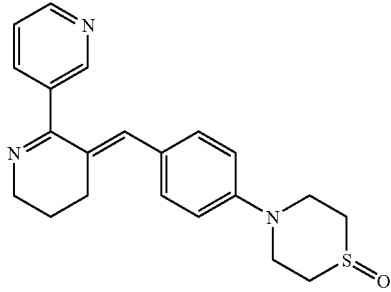

$^1$H NMR (CD$_3$OD) δ 8.73 (m, 1H), 8.63 (m, 1H), 7.82 (dt, J$_d$=7.8, J$_t$=1.9, 1H), 7.33 (dd, J=7.5, 4.8, 1H), 7.27 (d, J=8.8,

2H), 6.91 (d, J=8.9, 2H), 6.56 (s, 1H), 4.07 (m, 2H), 3.86 (t, J=5.5, 2H), 3.67 (m, 2H), 2.84 (m, 6H), 1.84 (m, 2H); MS (EI) m/z 366 (M⁺+1).

Example 74

3-[4-(1,1-Dioxo-1λ6-thiomorpholin-4-yl)-benzylidene]-3,4,5,6-tetrahydro-[2,3']bipyridinyl from 3-(4-thiomorpholin-4-ylbenzylidene)-3,4,5,6-tetrahydro[2,3']bipyridinyl To a solution of the thio ether from example 72 (43.5 mg, 0.122 mmol) in dichloromethane (1 mL) was added m-chloroperoxybenzoic acid (136 mg, 0.607 mmol, 4.9 eq) After 16 h, the reaction mixture was poured onto saturated sodium bicarbonate (3 mL) and was extracted with dichloromethane (3×10 mL) and dried over sodium sulfate. The residue was purified by chromatography [3/7 ethyl acetate/(70/30/1 ethylacetate/methanol/ammonium hydroxide)] to provide 2.1 mg (4%) of the sulfone.

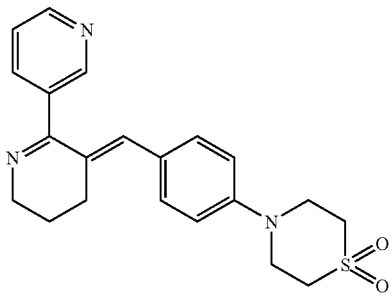

¹H NMR (CDCl₃) δ 8.74 (s, 1H), 8.63 (m, 1H), 7.84 (m, 1H), 7.34 (dd, J=7.8, 5.0, 1H), 7.28 (d, J=9.5, 2H), 6.91 (d, J=8.9, 2H), 6.57 (s, 1H), 4.08 (m, 2H), 3.86 (m, 3H), 3.67 (m, 2H), 2.78 (m, 5H), 1.85 (m, 2H); MS (EI) m/z 382 (M⁺+1).

Example 75

3-[4-(2,6-Dimethylmorpholin-4-yl)benzylidene]-3,4,5,6-tetrahydro[2,3']bipyridinyl from 3-(4-iodobenzylidene)-3,4,5,6-tetrahydro[2,3']bipyridinyl

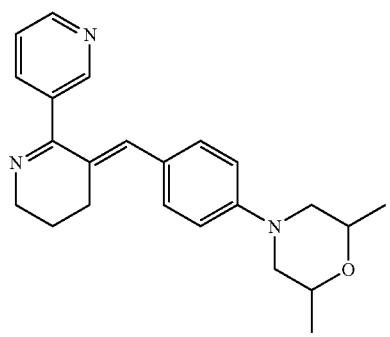

Yield: 96%. ¹H NMR (CD₃OD) δ 8.62 (m, 2H), 7.90 (dt, $J_d$=7.8, $J_f$=1.8, 1H), 7.54 (dd, J=7.8, 5.0, 1H), 7.29 (d, J=8.8, 2H), 6.94 (d, J=9.1, 2H), 6.89 (s, 1H), 3.77 (m, 2H), 3.67 (m, 3H), 3.34 (m, 2H), 2.95 (m, 2H), 2.35 (m, 1H), 1.90 (m, 2H), 1.24 (m, 6H); MS (EI) m/z 362 (M⁺+1).

Example 76

3-(4-[1,4]Diazepan-1-ylbenzylidene)-3,4,5,6-tetrahydro[2,3']bipyridinyl from 3-(4-iodobenzylidene)-3,4,5,6-tetrahydro[2,3']bipyridinyl

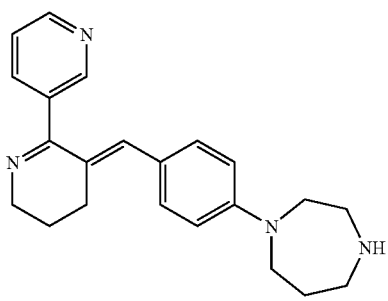

Yield: 69%. ¹H NMR (CD₃OD) δ 8.61 (dd, J=4.9, 1.5, 1H), 8.57 (d, J=1.5, 1H), 7.88 (dt, $J_d$=7.8, $J_f$=1.8, 1H), 7.51 (ddd, J=7.8, 4.9, 0.6, 1H), 7.26 (d, J=8.9, 2H), 6.77 (d, J=9.0, 2H), 6.50 (s, 1H), 3.68 (m, 6H), 3.13 (m, 2H), 2.93 (m, 4H), 2.04 (m, 2H), 1.89 (m, 3H); MS (EI) m/z 347 (M⁺+1).

Example 77

3-[3-(trans-2,5-Dimethylpiperazin-1-yl)benzylidene]-3,4,5,6-tetrahydro[2,3']bipyridinyl from 3-(3-iodobenzylidene)-3,4,5,6-tetrahydro[2,3']bipyridinyl

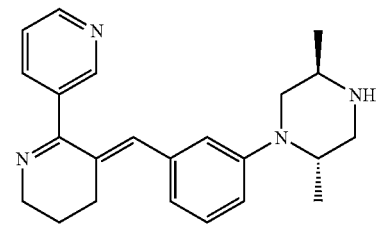

Yield: 24%. ¹H NMR (CD₃OD) δ 8.63 (bs, 2H), 7.94 (m, 1H), 7.54 (dd, J=7.6, 4.9, 1H), 7.38 (t, J=7.8, 1H), 7.16 (m, 3H), 6.63 (s, 1H), 3.83 (m, 2H), 3.35 (m, 2H), 3.20 (m, 2H), 2.87 (m, 4H), 1.86 (m, 2H), 1.28 (m, 3H), 1.19 (m, 3H), 0.94 (m, 3H); MS (EI) m/z 361 (M⁺+1).

Example 78

3-[3-(cis-3,5-Dimethylpiperazin-1-yl)benzylidene]-3,4,5,6-tetrahydro[2,3']bipyridinyl from 3-(3-iodobenzylidene)-3,4,5,6-tetrahydro[2,3']bipyridinyl

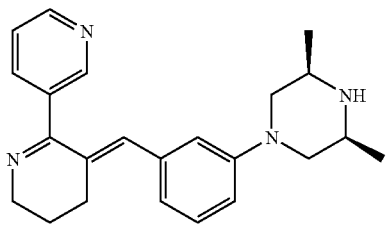

Yield: 29%. $^1$H NMR (CD$_3$OD) δ 8.62 (m, 2H), 7.95 (m, 1H), 7.54 (dd, J=7.8, 4.9, 1H), 7.31 (t, J=7.9, 1H), 6.96 (m, 3H), 6.63 (s, 1H), 3.80 (m, 3H), 3.38 (m, 4H), 2.86 (m, 2H), 2.63 (dd, J=13, 11, 2H), 1.86 (m, 2H), 1.34 (d, J=6.5, 6H); MS (EI) m/z 361 (M$^+$+1).

Example 79

3-(3-Thiomorpholin-4-yl-benzylidene)-3,4,5,6-tetrahydro[2,3']bipyridinyl from 3-(3-iodobenzylidene)-3,4,5,6-tetrahydro[2,3']bipyridinyl

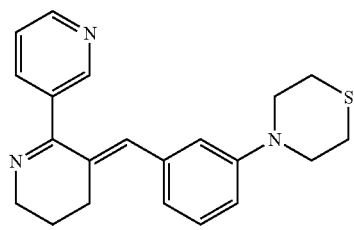

Yield: 54%. $^1$H NMR (CD$_3$OD) δ 8.63 (m, 2H), 7.94 (dt, J$_d$=7.9, J$_t$=1.7, 1H), 7.54 (ddd, J=7.8, 5.0, 0.8, 1H), 7.29 (m, 1H), 7.26 (t, J=8.1, 1H), 6.88 (m, 3H), 6.64 (s, 1H), 3.83 (t, J=5.4, 2H), 3.51 (m, 4H), 2.89 (m, 3H), 2.70 (m, 4H), 1.90 (m, 2H); MS (EI) m/z 350 (M$^+$+1).

Example 80

3-[3-(2,6-Dimethylmorpholin-4-yl)benzylidene]-3,4,5,6-tetrahydro[2,3']bipyridinyl from 3-(3-iodobenzylidene)-3,4,5,6-tetrahydro[2,3']bipyridinyl

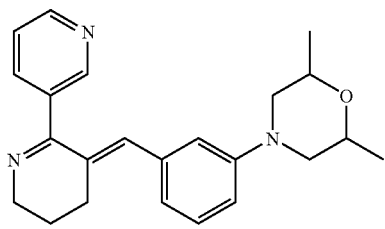

Yield: 83%. $^1$H NMR (CD$_3$OD) δ 8.63 (m, 2H), 7.94 (dt, J$_d$=7.8, J$_t$=1.8, 1H), 7.54 (ddd, J=7.8, 4.9, 0.6, 1H), 7.30 (m, 2H), 6.90 (m, 3H), 6.63 (s, 1H), 3.78 (m, 3H), 3.50 (m, 3H), 3.31 (m, 1H), 2.88 (m, 2H), 2.29 (t, J=1.8, 1H), 1.86 (m, 2H), 1.27 and 1.20 (two d, J=6.4 ea, 6H); MS (EI) m/z 362 (M$^+$+1).

Example 81

3-(3-[1,4]Diazepan-1-ylbenzylidene)-3,4,5,6-tetrahydro[2,3']bipyridinyl from 3-(3-iodobenzylidene)-3,4,5,6-tetrahydro[2,3']bipyridinyl

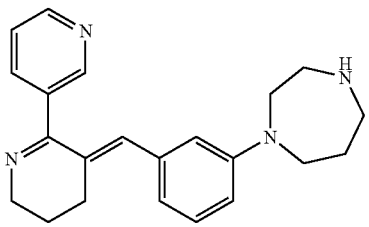

Yield: 48%. $^1$H NMR (CD$_3$OD) δ 8.61 (m, 2H), 7.92 (dt, J$_d$=7.8, J$_t$=1.8, 1H), 7.52 (dd, J=7.2, 4.3, 1H), 7.23 (t, J=8.0, 1H), 6.73 (m, 3H), 6.61 (s, 1H), 3.81 (m, 2H), 3.69 (m, 2H), 3.57 (m, 2H), 3.20 (m, 2H), 3.05 (m, 2H), 2.88 (m, 2H), 2.07 (m, 2H), 1.88 (m, 2H); MS (EI) m/z 347 (M$^+$+1).

Example 82

3-[3-(4-Phenylpiperazin-1-yl)benzylidene]-3,4,5,6-tetrahydro[2,3']bipyridinyl from 3-(3-iodobenzylidene)-3,4,5,6-tetrahydro[2,3']bipyridinyl

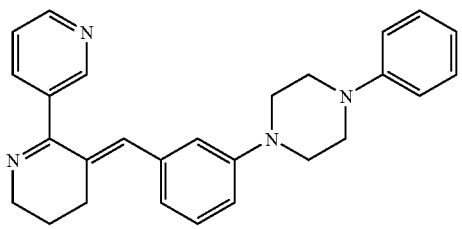

Yield: 55%. $^1$H NMR (CD$_3$OD) δ 8.63 (m, 2H), 7.93 (m, 1H), 7.52 (dd, J=7.8, 5.0, 1H), 7.33 (m, 5H), 7.00 (m, 3H), 6.89 (m, 3H), 6.64 (s, 1H), 3.83 (t, J=5.5, 2H), 3.30 (m, 8H), 2.90 (m, 2H), 1.86 (m, 2H); MS (EI) m/z 409 (M$^+$+1).

Example 83

3-{3-[4-(4-Fluorophenyl)piperazin-1-yl]benzylidene}-3,4,5,6-tetrahydro[2,3']bipyridinyl from 3-(3-iodobenzylidene)-3,4,5,6-tetrahydro[2,3']bipyridinyl

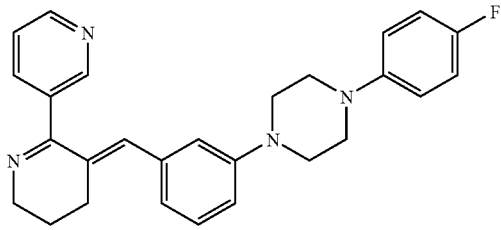

Yield: 53%. $^1$H NMR (CD$_3$OD) δ 8.63 (m, 2H), 7.93 (m, 1H), 7.53 (dd, J=7.8, 5.0, 1H), 7.33 (m, 3H), 7.02 (m, 5H), 6.90 (m, 1H), 6.64 (s, 1H), 3.83 (t, J=5.5, 2H), 3.29 (m, 8H), 2.87 (m, 2H), 1.87 (m, 2H); MS (EI) m/z 427 (M$^+$+1).

Example 84

3-(3-piperazin-1-ylbenzylidene)-3,4,5,6-tetrahydro[2,3']bipyridinyl from 3-(3-iodobenzylidene)-3,4,5,6-tetrahydro[2,3']bipyridinyl

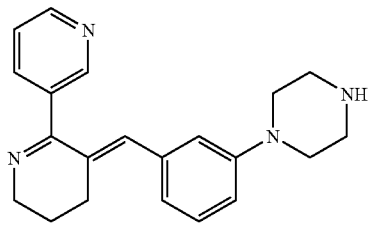

Yield: 19%. $^1$H NMR (CDCl$_3$) δ 8.61 (bs, 2H), 7.89 (m, 1H), 7.51 (m, 1H), 7.26 (m, 2H), 7.07 (m, 1H), 6.88 (m, 1H), 6.70 and 6.61 (two s, 1H tot), 3.81 (t, J=5.4, 2H), 3.30 (m, 6H), 3.15 (m, 2H), 2.87 (m, 2H), 1.85 (m, 2H); MS (EI) m/z 333 (M$^+$+1).

Example 85

3-{3-[(1S,4S)-2,5-Diazabicyclo[2.2.1]hept-2-yl]benzylidene}-3,4,5,6-tetrahydro[2,3']bipyridinyl from 3-(3-iodobenzylidene)-3,4,5,6-tetrahydro[2,3']bipyridinyl

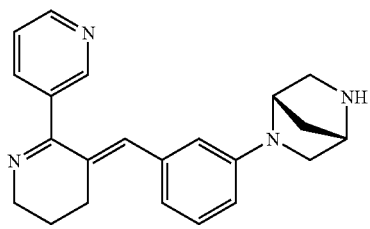

Yield: 22%. $^1$H NMR (CD$_3$OD) δ 8.59 (m, 2H), 7.89 (dt, J$_d$=7.9, J$_t$=1.8, 1H), 7.49 (m, 1H), 7.32 (m, 1H), 7.22 (t, J=7.9, 1H), 6.59 (m, 1H), 6.49 (s, 1H), 4.53 (s, 1H), 4.31 (s, 1H), 3.80 (m, 2H), 3.61 (m, 1H), 3.28 (m, 2H), 2.84 (m, 2H), 2.14 (m, 1H), 1.96 (m, 1H), 1.82 (m, 2H); MS (EI) m/z 345 (M$^+$+1).

Example 86

3-(3-[1,4]Oxazepan-4-ylbenzylidene)-3,4,5,6-tetrahydro[2,3']bipyridinyl from 3-(3-iodobenzylidene)-3,4,5,6-tetrahydro[2,3']bipyridinyl

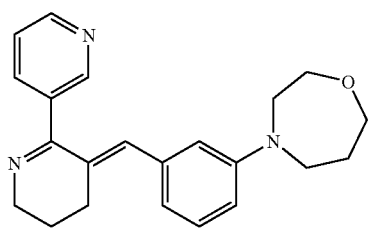

Yield: 27%. $^1$H NMR (CD$_3$OD) δ 8.63 (m, 2H), 7.93 (m, 1H), 7.53 (dd, J=7.3, 5.0, 1H), 7.20 (t, J=8.3, 1H), 6.73 (m, 1H), 6.64 (m, 2H), 6.63 (s, 1H), 3.81 (m, 4H), 3.64 (m, 6H), 2.89 (m, 2H), 1.98 (m, 2H), 1.86 (m, 2H); MS (EI) m/z 348 (M$^+$+1).

Example 87

3-[4-(4-Phenylpiperazin-1-yl)benzylidene]-3,4,5,6-tetrahydro[2,3']bipyridinyl from 3-(4-iodobenzylidene)-3,4,5,6-tetrahydro[2,3']bipyridinyl

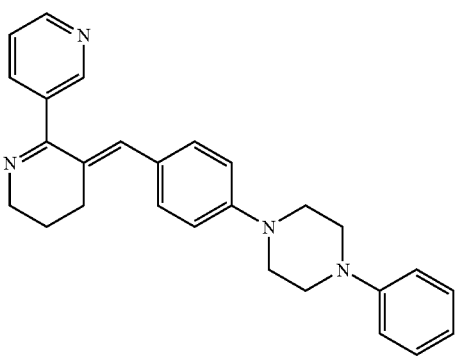

Yield: 40%. $^1$H NMR (CD$_3$OD) δ 8.63 (m, 2H), 7.92 (m, 1H), 7.55 (dd, J=7.7, 5.2, 1H), 7.34 (m, 2H), 7.25 (t, J=8.5, 2H), 7.01 (m, 3H), 6.86 (m, 1H), 6.63 (s, 1H), 3.80 (m, 2H), 3.43 (m, 3H), 3.30 (m, 6H), 2.95 (m, 2H), 1.91 (m, 2H); MS (EI) m/z 409 (M⁺+1).

Example 88

3-{-4-[4-(4-Fluorophenyl)piperazin-1-yl]benzylidene}-3,4,5,6-tetrahydro[2,3']bipyridinyl from 3-(4-iodobenzylidene)-3,4,5,6-tetrahydro[2,3']bipyridinyl

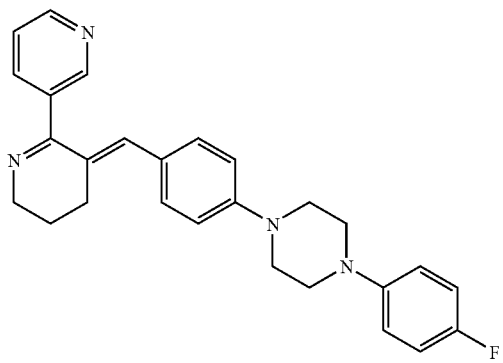

Yield: 75%. $^1$H NMR (CD$_3$OD) δ 8.61 (m, 2H), 7.89 (dt, J$_d$=7.9, J$_t$=1.8, 1H), 7.51 (ddd, J=7.8, 5.0, 0.6, 1H), 7.29 (d, J=8.8, 2H), 6.97 (m, 7H), 6.56 (s, 1H), 3.75 (t, J=5.5, 2H), 3.36 (m, 4H), 3.17 (m, 4H), 2.89 (m, 2H), 1.85 (m, 2H); MS (EI) m/z 427 (M⁺+1).

Example 89

3-{4-[(1S,4S)-2,5-Diazabicyclo[2.2.1]hept-2-yl]benzylidene}-3,4,5,6-tetrahydro[2,3']bipyridinyl from 3-(4-iodobenzylidene)-3,4,5,6-tetrahydro[2,3']bipyridinyl

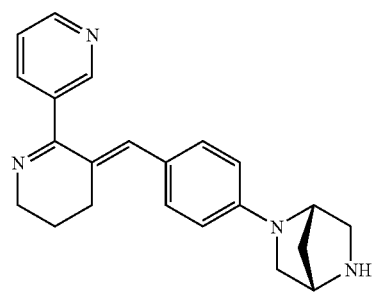

Yield: 64%. $^1$H NMR (CDCl$_3$) δ 8.57 (m, 2H), 7.85 (dt, J$_d$=7.9, J$_t$=1.7, 1H), 7.48 (ddd, J=7.9, 5.0, 0.9, 1H), 7.22 (d, J=8.8, 2H), 6.58 (d, J=8.8, 2H), 6.48 (s, 1H), 4.45 (3, 1H), 3.93 (s, 1H), 3.73 (t, J=5.5, 2H), 3.57 (dd, J=9.7, 2.2, 1H), 3.12 (m, 1H), 3.04 (s, 2H), 2.87 (m, 2H) 1.98 (m, 1H), 1.85 (m, 3H); MS (EI) m/z 345 (M⁺+1).

Example 90

3-(4-[1,4]Oxazepan-4-ylbenzylidene)-3,4,5,6-tetrahydro[2,3']bipyridinyl from 3-(4-iodobenzylidene)-3,4,5,6-tetrahydro[2,3']bipyridinyl

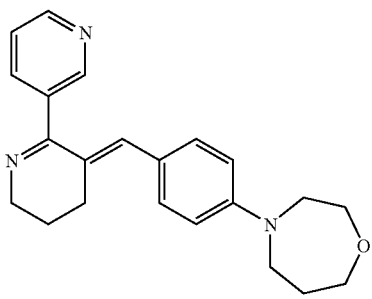

Yield: 46%. $^1$H NMR (CD$_3$OD) δ 8.65 (t, J=3.5, 1H), 8.61 (d, J=1.5, 1H), 7.91 (m, 1H), 7.54 (dd, J=7.6, 5.0, 1H), 7.30 (d, J=8.8, 2H), 6.77 (d, J=8.8, 2H), 6.62 (s, 1H), 3.78 (m, 4H), 3.66 (s, 5H), 2.94 (m, 2H), 1.94 (m, 5H); MS (EI) m/z 348 (M⁺+1).

Example 91

3-[4-(3-Methylpiperazin-1-yl)benzylidene]-3,4,5,6-tetrahydro[2,3']bipyridinyl from 3-(4-iodobenzylidene)-3,4,5,6-tetrahydro[2,3']bipyridinyl

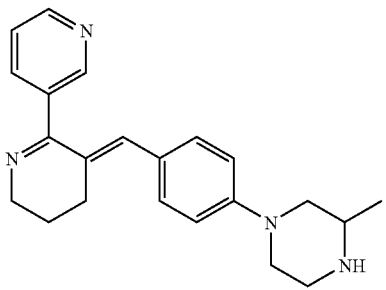

Yield: 39%. $^1$H NMR (CD$_3$OD) δ 8.61 (m, 2H), 7.89 (dt, J$_d$=8.1, J$_t$=1.7, 1H), 7.51 (ddd, J=7.8, 5.0, 0.6, 1H), 7.27 (d, J=8.8, 2H), 6.95 (d, J=8.9, 2H), 6.52 (s, 1H), 3.77 (t, J=5.5, 2H), 3.69 (m, 1H), 3.12 (m, 1H), 2.95 (m, 4H), 2.76 (m, 1H), 2.43 (dd, J=12.3, 10.4, 1H), 1.85 (m, 2H), 1.17 (d, J=6.4, 3H); MS (EI) m/z 347 (M⁺+1).

Example 92

3-[4-(2-Methylpiperazin-1-yl)benzylidene]-3,4,5,6-tetrahydro[2,3']bipyridinyl from 3-(4-iodobenzylidene)-3,4,5,6-tetrahydro[2,3']bipyridinyl

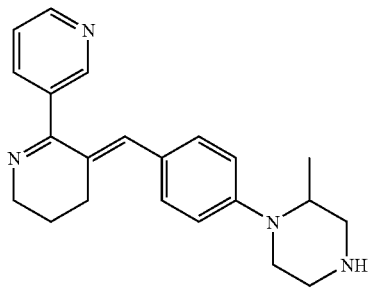

Yield: 10%. $^1$H NMR (CDCl$_3$) δ 8.61 (m, 2H), 7.90 (m, 1H), 7.53 (dd, J=7.8, 4.9, 1H), 7.28 (d, J=8.6, 2H), 6.93 (d, J=8.8, 2H), 6.53 (s, 1H), 4.06 (m, 1H), 3.77 (m, 2H), 3.32 (m, 2H), 3.05 (m, 2H), 2.91 (m, 5H), 1.87 (m, 2H), 1.08 (d, J=6.5, 3H); MS (EI) m/z 347 (M⁺+1).

Example 93

3-[3-(4-Ethylpiperazin-1-yl)benzylidene]-3,4,5,6-tetrahydro[2,3']bipyridinyl from 3-(3-iodobenzylidene)-3,4,5,6-tetrahydro[2,3']bipyridinyl

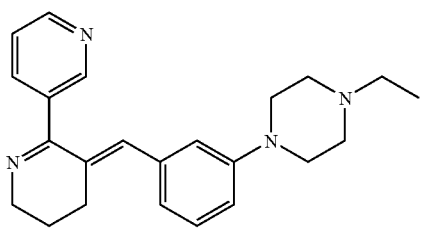

Yield: 47%. $^1$H NMR (CDCl$_3$) δ 8.63 (m, 2H), 7.94 (m, 1H), 7.52 (m, 1H), 7.28 (t, J=7.8, 1H), 6.96 (m, 1H), 6.89 (m, 2H), 6.63 (s, 1H), 3.83 (t, J=5.4, 2H), 3.32 (m, 2H), 2.88 (m, 2H), 2.80 (m, 3H), 2.66 (q, J=7.4, 2H), 2.49 (m, 2H), 1.86 (m, 2H), 1.20 (m, 3H); MS (EI) m/z 361 (M⁺+1).

Example 94

3-[4-(4-Ethylpiperazin-1-yl)benzylidene]-3,4,5,6-tetrahydro[2,3']bipyridinyl from 3-(4-iodobenzylidene)-3,4,5,6-tetrahydro[2,3']bipyridinyl

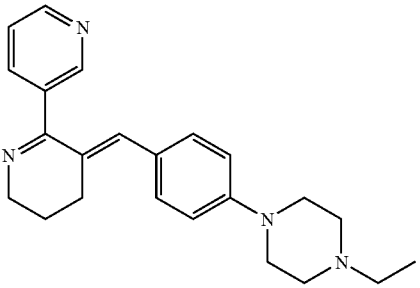

Yield: 77%. $^1$H NMR (CD$_3$OD) δ 8.61 (m, 2H), 7.89 (m, 1H), 7.51 (dd, J=7.6, 4.8, 1H), 7.28 (d, J=8.6, 2H), 6.94 (d, J=8.7, 2H), 6.54 (s, 1H), 3.76 (t, J=5.0, 2H), 3.29 (m, 4H), 2.89 (m, 2H), 2.65 (m, 4H), 2.52 (q, J=7.2, 2H), 1.85 (m, 2H), 1.15 (t, J=7.1, 3H); MS (EI) m/z 361 (M⁺+1).

Representative Procedure C

Example 95

3-[1-(4-Chlorobenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

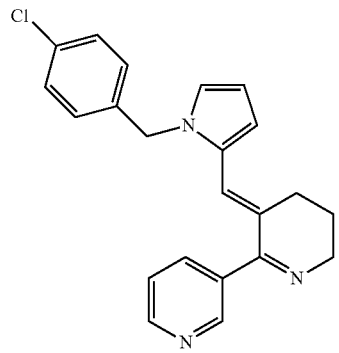

To a solution of 3-(1H-pyrrol-2-ylmethylene)-3,4,5,6-tetrahydro-[2,3']bipyridinyl [example 4] (0.330 g, 1.40 mmol) in DMF (5 mL) was added NaH (60% oil dispersion, 120 mg, 3.00 mmol, 2.1 eq). The mixture was stirred for 5 min and was treated with 4-chlorobenzyl chloride (0.450 g, 2.80 mmol, 2 eq) via syringe. The mixture was stirred at rt for 15 min and was quenched with MeOH. The reaction mixture was diluted with water, extracted with ether (2×), and the combined organic layers were dried over magnesium sulfate. The crude product was purified by chromatography [1/1 to 0/1 ethyl acetate/(70/30/1 ethyl acetate/methanol/ammonium hydroxide)] to provide 130 mg (26%) of product. $^1$H NMR (MeOD) δ 8.61-8.59 (m, 1H), 8.40 (d, J=1.4, 1H), 7.56-7.52 (m, 1H), 7.36-7.32 (m, 1H), 7.18 (d, J=8.4, 2H), 7.06 (d, J=1.4, 1H), 6.63 (d, J=8.3, 2H), 6.32-6.28 (m, 2H), 4.95 (s, 2H), 3.69-3.65 (m, 2H), 2.74-2.70 (m, 2H), 1.86-1.80 (m, 2H); MS (EI) m/z 363 (M⁺+1).

Using this general procedure the following compounds were prepared:

Example 96

3-[1-(4-Fluorobenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

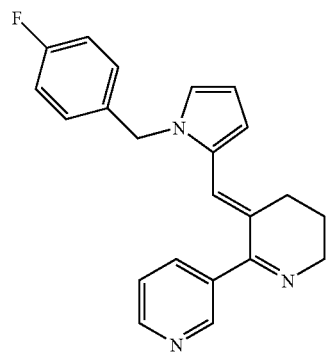

Yield: 11%. ¹H NMR (MeOD) δ 8.62-8.59 (m, 1H), 8.40 (d, J=1.6, 1H), 7.61-7.57 (m, 1H), 7.41-7.37 (m, 1H), 7.08 (d, J=2.2, 1H), 6.95-6.89 (m, 2H), 6.68-6.64 (m, 3H), 6.32-6.30 (m, 2H), 4.97 (s, 2H), 3.71-3.67 (m, 2H), 2.76-2.72 (m, 2H), 1.93-1.80 (m, 2H); MS (EI) m/z 346 (M⁺+1).

Example 97

3-[1-(4-Trifluoromethylbenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

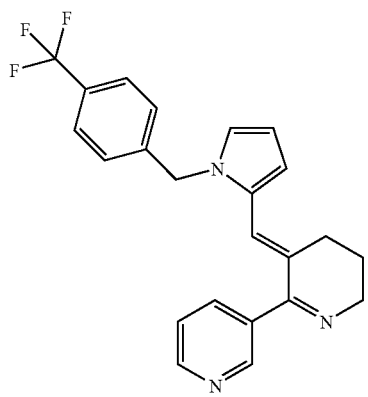

Yield: 31%. ¹H NMR (MeOD) δ 8.58-8.56 (m, 1H), 8.41 (d, J=1.4, 1H), 7.51-7.48 (m, 3H), 7.29-7.25 (m, 1H), 7.10-7.09 (m, 1H), 6.83 (d, J=8.0, 2H), 6.66-6.65 (m, 1H), 6.35-6.33 (m, 1H), 6.25 (s, 1H), 5.07 (s, 2H), 3.69-3.65 (m, 2H), 2.75-2.71 (m, 2H), 1.83-1.78 (m, 2H); MS (EI) m/z 396 (M⁺+1).

Example 98

3-[1-(4-Chlorobenzyl)-1H-pyrazol-3-ylmethylene]-3,4,5,6-tetrahydro[2,3']bipyridinyl from 3-(2H-pyrazol-3-ylmethylene)-3,4,5,6-tetrahydro[2,3']bipyridinyl

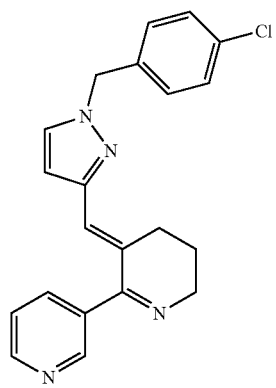

MS (EI) m/z 363 (M⁺+1).

Example 99

3-[1-(4-Fluorobenzyl)-1H-pyrazol-3-ylmethylene]-3,4,5,6-tetrahydro[2,3']bipyridinyl from 3-(2H-pyrazol-3-ylmethylene)-3,4,5,6-tetrahydro[2,3']bipyridinyl

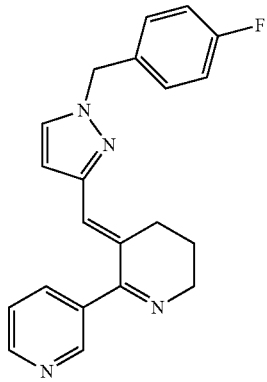

MS (EI) m/z 347 (M⁺+1).

Example 100

3-[1-(2,6-Dichlorobenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

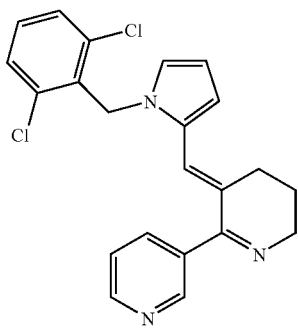

Yield: 37%. $^1$H NMR (MeOD) δ 8.63-8.59 (m, 2H), 7.91-7.87 (m, 1H), 7.54-7.49 (m, 1H), 7.39-7.30 (m, 3H), 6.68 (s, 1H), 6.63-6.62 (m, 1H), 6.56 (d, J=2.9, 1H), 6.21-6.19 (m, 1H), 5.10 (s, 2H), 3.76-3.72 (m, 2H), 2.83-2.79 (m, 2H), 1.91-1.83 (m, 2H); MS (EI) m/z 397 (M$^+$+1).

Example 101

3-[1-(3,4-Dichlorobenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

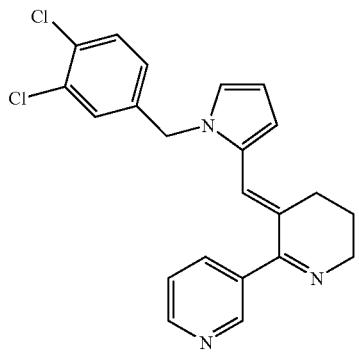

Yield: 3%. $^1$H NMR (MeOD) δ 8.59-8.57 (m, 1H), 8.41 (d, J=1.7, 1H), 7.56-7.52 (m, 1H), 7.37-7.30 (m, 2H), 7.07 (d, J=1.4, 1H), 6.82 (s, 1H), 6.67 (d, J=3.8, 1H), 6.57-6.54 (m, 1H), 6.35-6.33 (m, 1H), 6.21 (s, 1H), 5.00 (s, 2H), 3.71-3.68 (m, 2H), 2.78-2.74 (m, 2H), 1.90-1.81 (m, 2H); MS (EI) m/z 396, 398 (M$^+$+1).

Example 102

3-[1-(4-Trifluoromethoxybenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3'] bipyridinyl

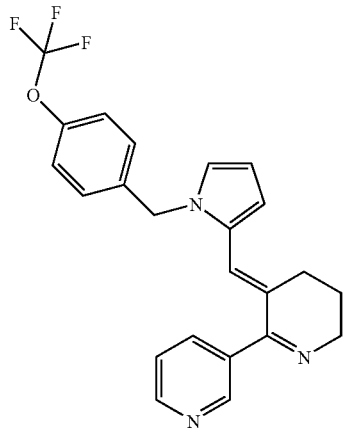

Yield: 19%. $^1$H NMR (MeOD) δ 8.61-8.59 (m, 1H), 8.42 (d, J=1.8, 1H), 7.55-7.51 (m, 1H), 7.35-7.31 (m, 1H), 7.12-708 (m, 3H), 6.74 (d, J=8.5, 2H), 6.64 (d, J=3.7, 1H), 6.33-6.30 (m, 2H), 4.99 (s, 2H), 3.69-3.65 (m, 2H), 2.74-2.70 (m, 2H), 1.85-1.77 (m, 2H); MS (EI) m/z 412 (M$^+$+1).

Example 103

3-(1-Biphenyl-4-ylmethyl-1H-pyrrol-2-ylmethylene)-3,4,5,6-tetrahydro[2,3']bipyridinyl from 3-(1H-pyrrol-3-ylmethylene)-3,4,5,6-tetrahydro[2,3']bipyridinyl

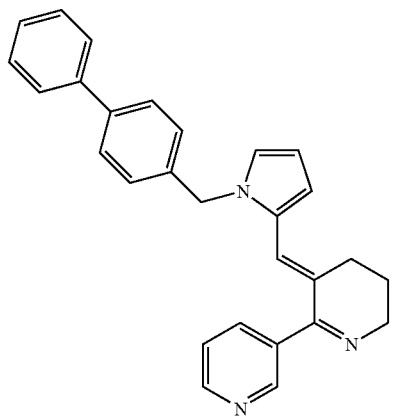

Yield: 6%. $^1$H NMR (MeOD) δ 8.56-8.54 (m, 1H), 8.40 (d, J=1.5, 1H), 7.58-7.55 (m, 2H), 7.51-7.25 (m, 7H), 7.07 (d, J=1.4, 1H), 6.68 (d, J=8.2, 2H), 6.63-6.61 (m, 1H), 6.37 (s, 1H), 6.33-6.31 (m, 1H), 4.96 (s, 2H), 3.65-3.62 (m, 2H), 2.72-2.68 (m, 2H), 1.81-1.78 (m, 2H); MS (EI) m/z 404 (M⁺+1).

Example 104

3-[1-(2-Fluorobenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

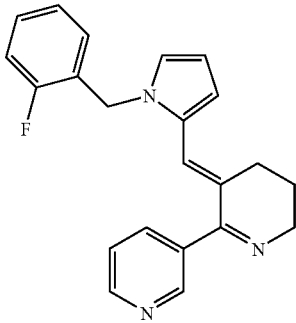

Yield: 12%. ¹H NMR (MeOD) δ 8.59-8.57 (m, 1H), 8.39 (d, J=1.6, 1H), 7.57-7.53 (m, 1H), 7.37-7.32 (m, 1H), 7.28-7.22 (m, 1H), 7.09 (d, J=1.5, 1H), 7.03-6.97 (m, 2H), 6.67 (d, J=3.2, 1H), 6.48-6.43 (t, J=7.5, 1H), 6.35-6.32 (m, 2H), 5.03 (s, 2H), 3.71-3.67 (m, 2H), 2.79-2.74 (m, 2H), 1.89-1.81 (m, 2H); MS (EI) m/z 346 (M⁺+1).

Example 105

3-(1-Methylpropyl-1H-pyrrol-2-ylmethylene)-3,4,5,6-tetrahydro[2,3']bipyridinyl from 3-(1H-pyrrol-3-ylmethylene)-3,4,5,6-tetrahydro[2,3']bipyridinyl

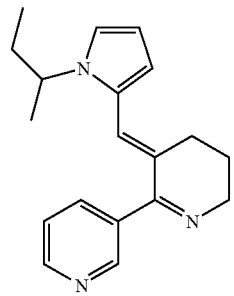

Yield: 4%. ¹H NMR (MeOD) δ 8.65-8.61 (m, 2H), 7.94-7.90 (m, 1H), 7.57-7.53 (m, 1H), 6.99-6.97 (m, 1H), 6.58-6.55 (m, 2H), 6.28-6.25 (m, 1H), 3.82-3.73 (m, 3H), 2.85-2.80 (m, 2H), 1.94-1.88 (m, 2H), 1.62-1.54 (m, 2H), 1.28 (d, J=6.7, 3H), 0.63 (t, J=7.4, 3H); MS (EI) m/z 294 (M⁺+1).

Example 106

3-(1-Pyridin-4-ylmethyl-1H-pyrrol-2-ylmethylene)-3,4,5,6-tetrahydro[2,3']bipyridinyl from 3-(1H-pyrrol-3-ylmethylene)-3,4,5,6-tetrahydro[2,3']bipyridinyl

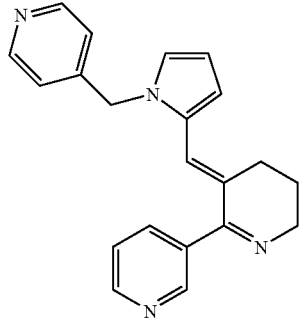

Yield: 55%. ¹H NMR (MeOD) δ 8.59-8.57 (m, 1H), 8.40-8.37 (m, 3H), 7.52-7.48 (m, 1H), 7.30-7.25 (m, 1H), 7.11-7.10 (m, 1H), 6.72-6.67 (m, 2H), 6.37-6.35 (m, 1H), 6.19 (s, 1H), 5.07 (s, 2H), 3.70-3.66 (m, 2H), 2.76-2.72 (m, 2H), 1.86-1.78 (m, 2H); MS (EI) m/z 329 (M⁺+1).

Example 107

3-[1-(1-Ethylpropyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

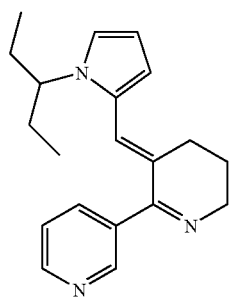

Yield: 2%. ¹H NMR (MeOD) δ 8.65-8.60 (m, 2H), 7.94-7.90 (m, 1H), 7.58-7.53 (m, 1H), 6.94-6.93 (m, 1H), 6.94-6.93 (m, 1H), 6.58-6.57 (m, 2H), 6.31-6.29 (m, 1H), 3.76 (t, J=5.3, 2H), 3.53-3.47 (m, 1H), 2.85-2.81 (m, 2H), 1.95-1.87 (m, 2H), 1.71-1.54 (m, 4H), 0.59 (t, J=7.3, 6H); MS (EI) m/z 308 (M$^+$+1).

Example 108

3-[1-(2-Chloro-6-fluorobenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

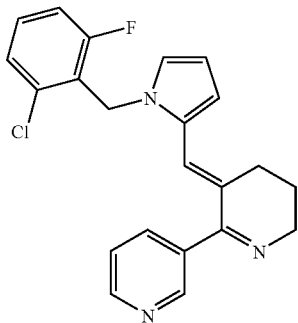

Yield: 38%. $^1$H NMR (MeOD) δ 8.64-8.61 (m, 1H), 8.57 (d, J=2.2, 1H), 7.86-7.82 (m, 1H), 7.51-7.46 (m, 1H), 7.33-7.26 (m, 1H), 7.16-7.13 (m, 1H), 7.02-6.95 (m, 1H), 6.88 (s, 1H), 6.66 (s, 1H), 6.53 (d, J=3.5, 1H), 6.21-6.19 (m, 1H), 5.02 (s, 2H), 3.71-3.67 (m, 2H), 2.77-2.73 (m, 2H), 1.84-1.80 (m, 2H); MS (EI) m/z 381 (M$^+$+1).

Example 109

3-(1-Pentafluorophenylmethyl-1H-pyrrol-2-ylmethylene)-3,4,5,6-tetrahydro[2,3']bipyridinyl from 3-(1H-pyrrol-3-ylmethylene)-3,4,5,6-tetrahydro[2,3']bipyridinyl

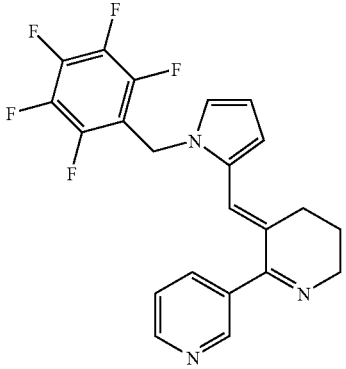

Yield: 11%. $^1$H NMR (MeOD) δ 8.66-8.64 (m, 1H), 8.56 (s, 1H), 7.90-7.86 (m, 1H), 7.55-7.51 (m, 1H), 7.04 (d, J=1.3, 1H), 6.60-6.57 (m, 2H), 6.28-6.26 (m, 1H), 5.10 (s, 1H), 3.74-3.70 (m, 2H), 2.79-2.75 (m, 2H), 1.91-1.85 (m, 2H); MS (EI) m/z 418 (M$^+$+1).

Example 110

3-[1-(2,4,5-Trifluorobenzyl)-1H-pyrrol-2-ylmethylene]-3,4,5,6-tetrahydro[2,3']bipyridinyl from 3-(1H-pyrrol-3-ylmethylene)-3,4,5,6-tetrahydro[2,3']bipyridinyl

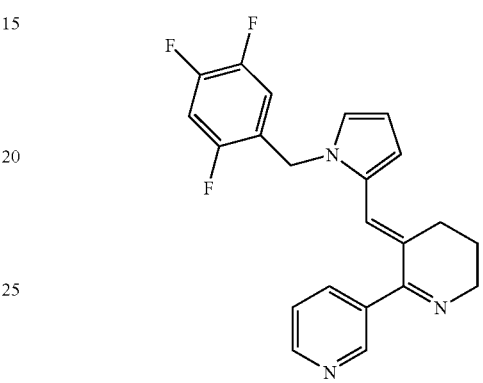

Yield: 36%. $^1$H NMR (MeOD) δ 8.61-8.59 (m, 1H), 8.41 (s, 1H), 7.67-7.63 (m, 1H), 7.42-7.38 (m, 1H), 7.13-7.08 (m, 2H), 6.66 (s, 1H), 6.35-6.33 (m, 2H), 6.26 (s, 1H), 4.99 (s, 2H), 3.72-3.68 (m, 2H), 2.78-2.76 (m, 2H), 1.87-1.83 (m, 2H); MS (EI) m/z 382 (M$^+$+1).

Example 111

3-(1-Ethyl-1H-pyrazol-3-ylmethylene)-3,4,5,6-tetrahydro[2,3']bipyridinyl from 3-(2H-pyrazol-3-ylmethylene)-3,4,5,6-tetrahydro[2,3']bipyridinyl

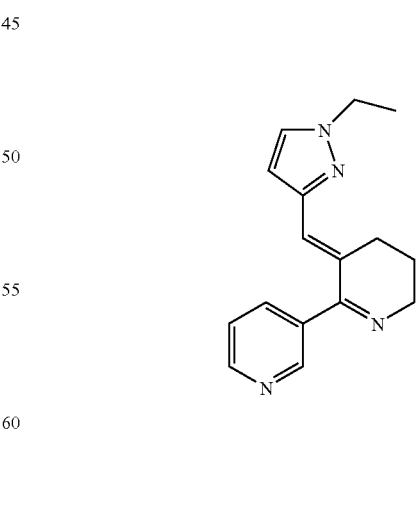

Yield: 3%. $^1$H NMR (CDCl$_3$) δ 8.73 (d, J=1.5, 1H), 8.62-8.60 (m, 1H), 7.82 (d, J=2.0, 1H), 7.40 (d, J=2.3, 1H), 7.33-7.29 (m, 1H), 6.64 (s, 1H), 6.40 (d, J=2.3, 1H), 4.17 (q, J=7.3, 1H), 3.88-3.82 (m, 2H), 2.94-2.89 (m, 2H), 1.91-1.84 (m, 2H), 1.48 (t, J=7.3, 3H); MS (EI) m/z 267 (M⁺+1).

Example 112

3-[1-(2-Methylpropyl)-1H-pyrazol-3-ylmethylene]-3,4,5,6-tetrahydro[2,3']bipyridinyl from 3-(2H-pyrazol-3-ylmethylene)-3,4,5,6-tetrahydro[2,3']bipyridinyl

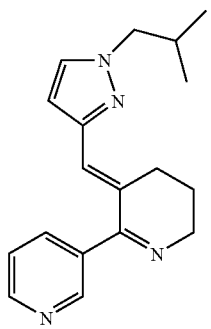

Yield: 10%. ¹H NMR (CDCl₃) δ 8.70 (d, J=1.6, 1H), 8.59-8.57 (m, 1H), 7.79-7.76 (m, 1H), 7.34 (d, J=2.2, 1H), 7.29-7.26 (m, 1H), 6.61 (s, 1H), 6.37 (d, J=2.3, 1H), 3.86 (d, J=7.3, 2H), 3.82-3.79 (m, 2H), 2.91-2.86 (m, 2H), 2.24-2.05 (m, 1H), 1.85-1.81 (m, 2H), 0.86 (d, J=6.7, 6H); MS (EI) m/z 295 (M⁺+1).

Example 113

3-(1-Cyclopropylmethyl-1H-pyrazol-3-ylmethylene)-3,4,5,6-tetrahydro[2,3']bipyridinyl from 3-(2H-pyrazol-3-ylmethylene)-3,4,5,6-tetrahydro[2,3']bipyridinyl

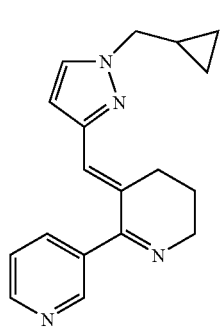

Yield: 5%. ¹H NMR (CDCl₃) δ 8.72 (d, J=1.5, 1H), 8.61-8.59 (m, 1H), 7.81-7.78 (m, 1H), 7.50 (d, J=2.3, 1H), 7.32-7.28 (m, 1H), 6.63 (s, 1H), 6.40 (d, J=2.4, 1H), 3.96 (d, J=7.1, 2H), 3.82 (t, J=5.5, 2H), 2.93-2.88 (m, 2H), 1.87-1.83 (m, 2H), 1.26-1.22 (m, 1H), 0.64-0.60 (m, 2H), 0.38-0.32 (m, 2H); MS (EI) m/z 293 (M⁺+1).

Example 114

3-(1-Cyclobutylmethyl-1H-pyrazol-3-ylmethylene)-3,4,5,6-tetrahydro-[2,3']bipyridinyl from 3-(2H-pyrazol-3-ylmethylene)-3,4,5,6-tetrahydro[2,3']bipyridinyl

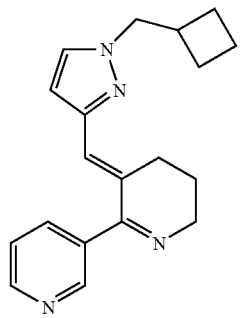

Yield: 4%. ¹H NMR (CDCl₃) δ 8.62 (d, J=1.5, 1H), 8.50-8.47 (m, 1H), 7.71-7.67 (m, 1H), 7.25 (d, J=2.2, 1H), 7.20-7.16 (m, 1H), 6.52 (s, 1H), 6.26 (d, J=2.3, 1H), 3.98 (d, J=7.3, 2H), 3.72-3.69 (m, 2H), 2.82-2.77 (m, 2H), 2.68-2.61 (m, 1H), 1.97-1.87 (m, 2H), 1.82-1.61 (m, 6H); MS (EI) m/z 307 (M⁺+1).

Example 115

3-(1-Cyclohexylmethyl-1H-pyrazol-3-ylmethylene)-3,4,5,6-tetrahydro[2,3']bipyridinyl from 3-(2H-pyrazol-3-ylmethylene)-3,4,5,6-tetrahydro[2,3']bipyridinyl

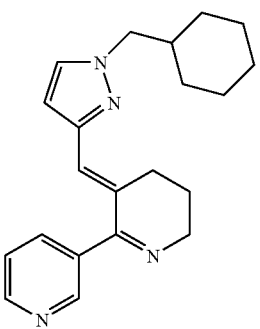

Yield: 2%. ¹H NMR (CDCl₃) δ 8.72 (d, J=1.5, 1H), 8.61-8.59 (m, 1H), 7.81-7.78 (m, 1H), 7.33 (d, J=2.2, 1H), 7.32-7.28 (m, 1H), 6.64 (s, 1H), 6.38 (d, J=2.3, 1H), 3.90 (d, J=7.3, 2H), 3.84-3.80 (m, 2H), 2.92-2.87 (m, 2H), 1.89-1.81 (m, 2H), 1.71-1.54 (m, 5H), 1.23-1.10 (m, 4H), 0.98-0.90 (m, 2H); MS (EI) m/z 335 (M$^+$+1).

Example 116

3-(1-Cyclopentyl-1H-pyrazol-3-ylmethylene)-3,4,5,6-tetrahydro[2,3']bipyridinyl from 3-(2H-pyrazol-3-ylmethylene)-3,4,5,6-tetrahydro[2,3']bipyridinyl

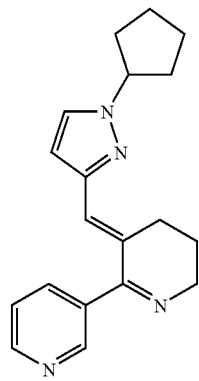

Yield: 2%. $^1$H NMR (CDCl$_3$) δ 8.71 (d, J=1.5, 1H), 8.60-8.58 (m, 1H), 7.81-7.77 (m, 1H), 7.40 (d, J=2.3, 1H), 7.31-7.28 (m, 1H), 6.62 (s, 1H), 6.35 (d, J=2.4, 1H), 4.63-4.58 (m, 1H), 3.82-3.79 (m, 2H), 2.92-2.87 (m, 2H), 2.15-1.63 (m, 10H); MS (EI) m/z 307 (M$^+$+1).

Example 117

3-[5-Bromo-2-(4-chlorobenzyl)-2H-pyrazol-3-ylmethylene]-3,4,5,6-tetrahydro[2,3']bipyridinyl from 3-(2H-pyrazol-3-ylmethylene)-3,4,5,6-tetrahydro[2,3']bipyridinyl

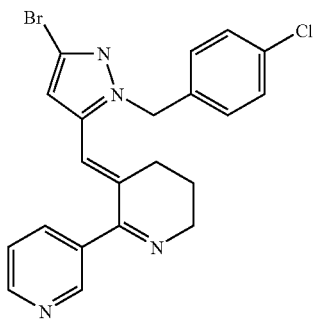

Yield: 4%. $^1$H NMR (CDCl$_3$) δ 8.75-8.74 (m, 1H), 8.62-8.60 (m, 1H), 7.85-7.81 (m, 1H), 7.34-7.29 (m, 4H), 7.17-7.14 (m, 2H), 6.46 (s, 1H), 5.24 (s, 2H), 3.86-3.82 (m, 2H), 3.06-3.01 (m, 2H), 1.85-1.78 (m, 2H); MS (EI) m/z 443, 445 (M$^+$+1).

Representative Procedure D

Example 118

3-{4-[(1S,4S)-5-Ethyl-2,5-Diazabicyclo[2.2.1]hept-2-yl]benzylidene}-3,4,5,6-tetrahydro[2,3']bipyridinyl from 3-{4-[(1S,4S)-2,5-diazabicyclo[2.2.1]hept-2-yl]benzylidene}-3,4,5,6-tetrahydro[2,3']bipyridinyl

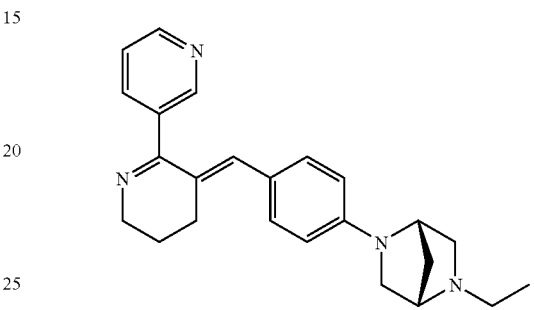

To a solution of the amine (51.6 mg, 0.150 mmol) in acetonitrile (1 mL) was added potassium carbonate (33.3 mg, 0.241, 1.6 eq) and iodoethane (13 μL, 0.16 mmol, 1.1 eq). After 12 h, the reaction mixture was adsorbed on a bed of silica gel and was purified by chromatography [1/1 to 0/1 ethyl acetate/(70/30/1 ethylacetate/methanol/ammonium hydroxide)] to provide 40.6 mg (73%) of the adduct as an oil. Data: $^1$H NMR (CD$_3$OD) δ 8.59 (m, 2H), 7.89 (dt, J$_d$=7.8, J$_t$=1.8, 1H), 7.52 (dd, J=7.5, 5.0, 1H), 7.26 (d, J=8.7, 2H), 6.74 (d, J=8.8, 2H), 6.51 (s, 1H), 3.75 (t, J=5.4, 2H), 3.61 (m, 2H), 3.53 (t, J=6.3, 2H), 2.91 (q, J=6.4, 2H), 2.76 (m, 2H), 2.60 (m, 2H), 2.38 (s, 3H), 2.02 (m, 2H), 1.86 (m, 3H); MS (EI) m/z 373 (M$^+$+1).

Using this general procedure the following compounds were prepared:

Example 119

3-[4-(4-Cyclopropylmethylpiperazin-1-yl)benzylidene]-3,4,5,6-tetrahydro[2,3']bipyridinyl from 3-[4-(4-piperazin-1-yl)benzylidene]-3,4,5,6-tetrahydro[2,3']bipyridinyl

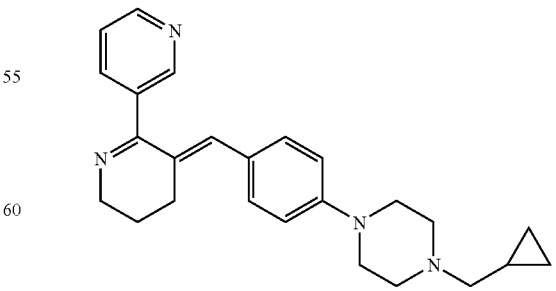

Yield: 37%. $^1$H NMR (CDCl$_3$) δ 8.74 (m, 1H), 8.62 (m, 1H), 7.81 (dt, J$_d$=7.8, J$_t$=2.0, 1H), 7.32 (dd, J=7.8, 4.9, 1H), 7.25 (d, J=8.8, 2H), 6.88 (d, J=8.8, 2H), 6.55 (s, 1H), 3.84 (t, J=5.4, 2H), 3.29 (m, 4H), 2.86 (m, 2H), 2.68 (m, 4H), 2.31 (q, J=7.2, 2H), 1.83 (m, 2H), 0.91 (m, 1H), 0.53 (m, 2H), 0.12 (m, 2H); MS (EI) m/z 387 (M⁺+1).

Example 120

3-[4-(4-Cyclopentylpiperazin-1-yl)benzylidene]-3,4,5,6-tetrahydro[2,3']bipyridinyl from 3-[4-(4-piperazin-1-yl)benzylidene]-3,4,5,6-tetrahydro[2,3']bipyridinyl

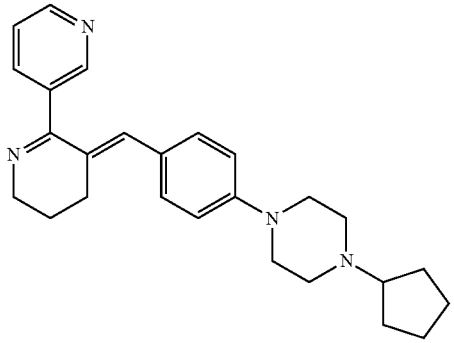

Yield: 31%. ¹H NMR (CDCl₃) δ 8.73 (m, 1H), 8.62 (m, 1H), 7.81 (dt, $J_d$=7.8, $J_t$=1.9, 1H), 7.32 (ddd, J=7.9, 4.9, 0.6, 1H), 7.25 (dd, J=7.7, 5.3, 2H), 6.89 (dd, J=8.6, 6.1, 2H), 6.55 (s, 1H), 3.85 (m, 2H), 3.25 (m, 4H), 2.85 (m, 2H), 2.65 (m, 3H), 2.53 (m, 2H), 1.91-1.55 (m, 10H); MS (EI) m/z 401 (M⁺+1).

Example 121

3-{4-[(1S,4S)-5-Methyl-2,5-Diazabicyclo[2.2.1]hept-2-yl]benzylidene}-3,4,5,6-tetrahydro[2,3']bipyridinyl from 3-{4-[(1S,4S)-2,5-diazabicyclo[2.2.1]hept-2-yl]benzylidene}-3,4,5,6-tetrahydro[2,3']bipyridinyl

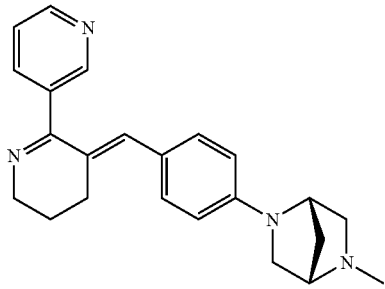

Yield: 13%. ¹H NMR (CDCl₃) δ 8.58 (m, 2H), 7.87 (m, 1H), 7.51 (m, 1H), 7.23 (two d, J=8.8 ea, 2H), 6.60 (two d, J=8.8 ea, 2H), 6.48 (s, 1H), 4.36 (s, 1H), 3.74 (m, 2H), 3.55 (s, 1H), 3.40 (m, 1H), 3.31 (m, 2H), 2.80 (m, 4H), 2.38 and 2.37 (two s, 3H), 1.92 (m, 6H); MS (EI) m/z 359 (M⁺+1).

Example 122

3-{4-[(1S,4S)-5-Cyclopropylmethyl-2,5-Diazabicyclo[2.2.1]hept-2-yl]benzylidene}-3,4,5,6-tetrahydro[2,3']bipyridinyl from 3-{4-[(1S,4S)-2,5-diazabicyclo[2.2.1]hept-2-yl]benzylidene}-3,4,5,6-tetrahydro[2,3']bipyridinyl

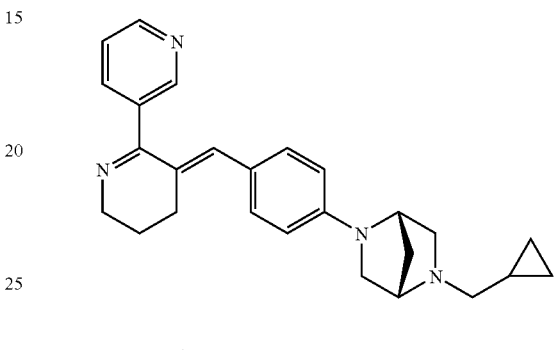

Yield: 49%. ¹H NMR (CD₃OD) δ 8.44 (dd, J=4.9, 1.4, 1H), 8.40 (d, J=1.4, 1H), 7.71 (dt, $J_d$=7.9, $J_t$=2.0, 1H), 7.34 (ddd, J=7.8, 5.0, 0.7, 1H), 7.08 (d, J=8.7, 2H), 6.44 (d, J=8.8, 2H), 6.34 (s, 1H), 4.25 (s, 1H), 3.78 (s, 1H), 3.57 (t, J=5.5, 2H), 3.21 (m, 2H), 2.90 (dd, J=10.2, 1.7, 1H), 2.71 (m, 3H), 2.35 (m, 2H), 1.77 (m, 5H), 0.74 (m, 1H), 0.37 (m, 2H), 0.02 (m, 2H); MS (EI) m/z 399 (M⁺+1).

Example 123

3-[4-(4-Methyl[1,4]diazepan-1-yl)benzylidene]-3,4,5,6-tetrahydro[2,3']bipyridinyl from 3-[4-([1,4]diazepan-1-yl)benzylidene]-3,4,5,6-tetrahydro[2,3']bipyridinyl

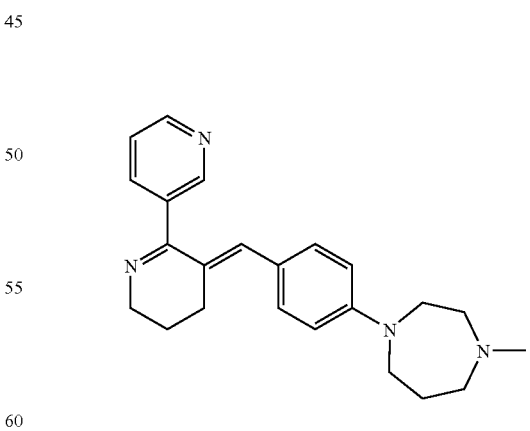

Yield: 16%. ¹H NMR (CD₃OD) δ 8.60 (dd, J=4.9, 1.6, 1H), 8.57 (dd, J=2.1, 0.7, 1H), 7.87 (dt, $J_d$=7.8, $J_t$=1.9, 1H), 7.50 (ddd, J=7.8, 4.9, 0.7, 1H), 7.22 (d, J=8.7, 2H), 6.58 (d, J=8.8, 2H), 6.48 (s, 1H), 3.74 (t, J=5.5, 2H), 3.67 (s, 1H), 3.35 (m, 2H), 2.89 (m, 3H), 2.55 (m, 3H), 1.91 (m, 5H), 1.06 (t, J=7.2, 3H); MS (EI) m/z 361 (M⁺+1).

Example 124

3-[4-(4-Cyclopropylmethyl[1,4]diazepan-1-yl)benzylidene]-3,4,5,6-tetrahydro[2,3']bipyridinyl from 3-[4-([1,4]diazepan-1-yl)benzylidene]-3,4,5,6-tetrahydro[2,3']bipyridinyl

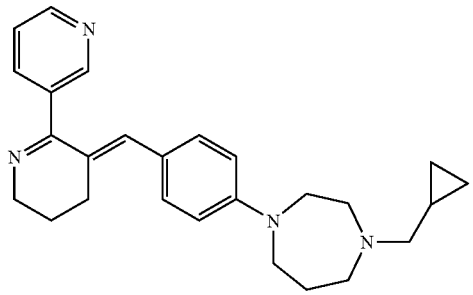

Yield: 20%. ¹H NMR (CD₃OD) δ 8.64 (m, 2H), 7.93 (dt, $J_d$=7.8, $J_t$=1.9, 1H), 7.56 (ddd, J=7.2, 4.4, 0.6, 1H), 7.32 (d, J=8.8, 2H), 6.80 (d, J=9.0, 2H), 6.61 (s, 1H), 3.76 (m, 4H), 3.57 (t, J=6.2, 2H), 3.14 (m, 2H), 2.96 (m, 4H), 2.75 and 2.67 (two d, J=6.9 ea, 2H), 2.10 (m, 2H), 1.94 (m, 2H), 1.01 (m, 1H), 0.64 (m, 2H), 0.28 (m, 2H); MS (EI) m/z 401 (M⁺+1).

Example 125

3-[4-(4-Cyclopentyl[1,4]diazepan-1-yl)-benzylidene]-3,4,5,6-tetrahydro[2,3']bipyridinyl from 3-[4-([1,4]diazepan-1-yl)benzylidene]-3,4,5,6-tetrahydro[2,3']bipyridinyl

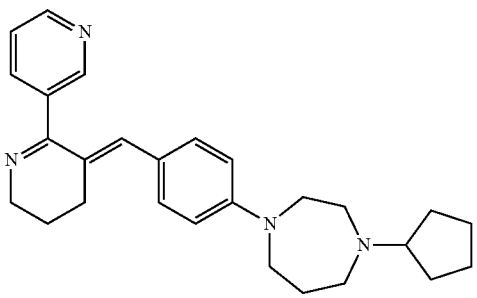

Yield: 13%. ¹H NMR (CD₃OD) δ 8.59 (m, 2H), 7.84 (m, 1H), 7.46 (dd, J=7.8, 4.9, 1H), 7.25 (d, J=8.4, 2H), 6.71 (d, J=8.8, 2H), 6.51 (s, 1H), 3.58 (m, 7H), 3.17 (m, 2H), 2.88 (m, 5H), 2.07 (m, 2H), 1.73 (m, 4H); MS (EI) m/z 415 (M⁺+1).

Example 126

3-[4-(4-Isobutyl-[1,4]diazepan-1-yl)-benzylidene]-3,4,5,6-tetrahydro-[2,3']bipyridinyl from 3-[4-([1,4]diazepan-1-yl)benzylidene]-3,4,5,6-tetrahydro[2,3']bipyridinyl

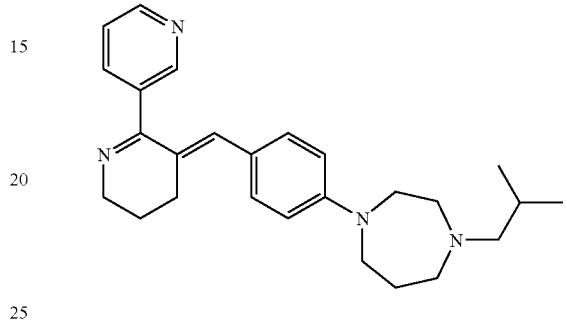

Yield: 11%. ¹H NMR (CDCl₃) δ 8.74 (m, 1H), 8.62 (dd, J=4.8, 1.7, 1H), 7.81 (dt, $J_d$=7.7, $J_t$=2.1, 1H), 7.32 (ddd, J=5.7, 4.9, 1.1, 1H), 7.23 (d, J=8.8, 2H), 6.66 (d, J=8.9, 2H), 6.53 (s, 1H), 3.83 (t, J=5.4, 2H), 3.53 (m, 4H), 2.87 (m, 2H), 2.74 (m, 2H), 2.56 (m, 2H), 1.88 (m, 6H), 0.87 (d, J=6.6, 6H); MS (EI) m/z 403 (M⁺+1).

Example 127

3-{4-[(1S,4S)-5-(2-Methylpropyl)-2,5-diazabicyclo[2.2.1]hept-2-yl]benzylidene}-3,4,5,6-tetrahydro[2,3']bipyridinyl from 3-{4-[(1S,4S)-2,5-diazabicyclo[2.2.1]hept-2-yl]benzylidene}-3,4,5,6-tetrahydro[2,3']bipyridinyl

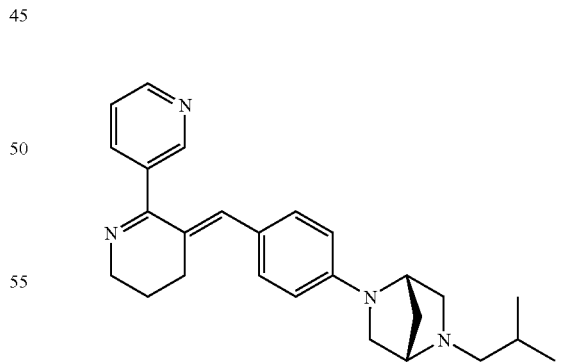

Yield: 54%. ¹H NMR (CDCl₃) δ 8.73 (d, J=1.5, 1H), 8.69 (dd, J=4.9, 1.6, 1H), 7.95 (dt, $J_d$=7.8, $J_t$=1.9, 1H), 7.40 (dd, J=7.9, 5.0, 1H), 7.29 (d, J=8.2, 2H), 6.73 (s, 1H), 6.54 (d, J=8.8, 2H), 4.31 (s, 1H), 3.86 (t, J=5.5, 2H), 3.68 (s, 1H), 3.41

(s, 2H), 3.13 (s, 1H), 2.92 (m, 3H), 2.60 (m, 1H), 2.35 (m, 2H), 2.11 (m, 1H), 1.92 (m, 3H), 1.67 (m, 1H), 0.90 (d, J=6.6, 6H); MS (EI) m/z 401 (M$^+$+1).

Example 128

3-{4-[(1S,4S)-5-Cyclopentyl-2,5-diazabicyclo[2.2.1]hept-2-yl]benzylidene}-3,4,5,6-tetrahydro[2,3']bipyridinyl from 3-{4-[(1S,4S)-2,5-diazabicyclo[2.2.1]hept-2-yl]benzylidene}-3,4,5,6-tetrahydro[2,3']bipyridinyl

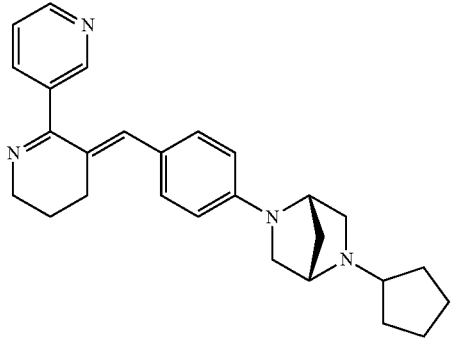

Yield: 42%. $^1$H NMR (CDCl$_3$) δ 8.73 (s, 2H), 8.00 (m, 2H), 7.45 (dd, J=7.5, 4.8, 1H), 7.35 (d, J=8.6, 2H), 6.82 (s, 1H), 6.61 (d, J=8.7, 2H), 4.56 (s, 1H), 4.34 (s, 1H), 3.88 (m, 3H), 3.64 (m, 2H), 3.30 (m, 1H), 2.96 (s, 4H), 2.65 (m, 1H), 2.19 (m, 1H), 2.00 (m, 8H); MS (EI) m/z 413 (M$^+$+1).

Example 129

3-[4-(4-Ethyl[1,4]diazepan-1-yl)benzylidene]-3,4,5,6-tetrahydro[2,3']bipyridinyl from 3-[4-([1,4]diazepan-1-yl)benzylidene]-3,4,5,6-tetrahydro[2,3']bipyridinyl

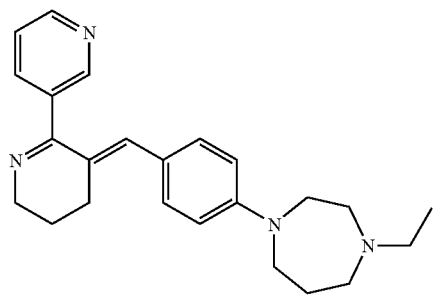

Yield: 66%. $^1$H NMR (CDCl$_3$) δ 8.72 (d, J=1.6, 1H), 8.67 (dd, J=4.9, 1.6, 1H), 7.90 (dt, J$_d$=7.8, J$_t$=1.9, 1H), 7.38 (ddd, J=7.8, 4.9, 0.6, 1H), 7.28 (d, J=8.8, 2H), 6.68 (d, J=9.1, 2H), 6.67 (s, 1H), 3.84 (t, J=5.5, 2H), 3.72 (m, 2H), 3.56 (t, J=6.3, 2H), 2.92 (m, 5H), 2.75 (m, 4H), 2.15 (m, 2H), 1.90 (m, 2H), 1.18 (t, J=7.1, 3H); MS (EI) m/z 375 (M$^+$+1).

Representative Procedure E

Example 130

Cyclopropyl-{4-[4-(5,6-dihydro-4H-[2,3']bipyridinyl-3-ylidenemethyl)phenyl]piperazin-1-yl}methanone from 3-[4-(4-piperazin-1-yl)benzylidene]-3,4,5,6-tetrahydro[2,3']bipyridinyl

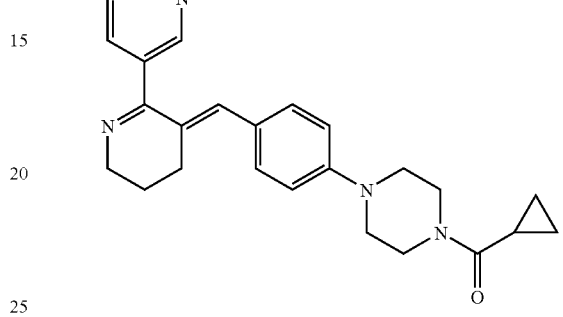

To a solution of the amine (95.0 mg, 0.286 mmol) in dichloromethane (1 mL) was added pyridine (36 μL, 0.45 mmol, 1.6 eq), cycloproylcarbonyl chloride (33 μL, 0.36 mmol, 1.3 eq), and a crystal of dimethylaminopyridine. After 20 h, the reaction mixture was adsorbed on a bed of silica gel and was purified by chromatography [1/0 to 1/1 ethyl acetate/(70/30/1 ethylacetate/methanol/ammonium hydroxide)] to provide 2.7 mg (46%) of the adduct as an oil. Data: $^1$H NMR (CD$_3$OD) δ 8.60 (m, 2H), 7.88 (dt, J$_d$=7.8, J$_t$=1.7, 1H), 7.50 (dd, J=7.8, 5.0, 1H), 7.28 (d, J=8.7, 2H), 6.95 (d, J=8.7, 2H), 6.52 (s, 1H), 3.88 (m, 2H), 3.74 (m, 4H), 3.26 (m, 4H), 2.88 (m, 2H), 1.97 (m, 1H), 1.84 (m, 2H), 0.88 (m, 4H); MS (EI) m/z 401 (M$^+$+1).

Using this general procedure the following compounds were prepared:

Example 131

1-{4-[4-(5,6-Dihydro-4H-[2,3']bipyridinyl-3-ylidenemethyl)phenyl]piperazin-1-yl}propan-1-one from 3-[4-(4-piperazin-1-yl)benzylidene]-3,4,5,6-tetrahydro[2,3']bipyridinyl

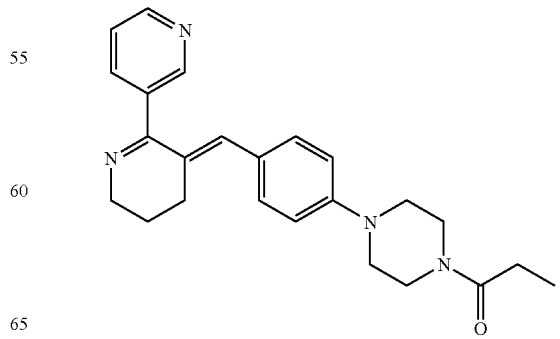

Yield: 47%. ¹H NMR (CD₃OD) δ 8.60 (m, 2H), 7.88 (dt, J_d=7.8, J_t=1.9, 1H), 7.50 (dd, J=7.8, 5.0, 1H), 7.27 (d, J=8.8, 2H), 6.95 (d, J=8.8, 2H), 6.52 (s, 1H), 3.76 (t, J=5.5, 2H), 3.67 (m, 4H), 3.25 (m, 4H), 2.88 (m, 2H), 2.44 (q, J=7.5, 2H), 1.84 (m, 2H), 1.13 (t, J=7.4, 3H); MS (EI) m/z 389 (M⁺+1).

Example 132

1-{4-[4-(5,6-Dihydro-4H-[2,3']bipyridinyl-3-ylidenemethyl)phenyl]piperazin-1-yl}-2,2,2-trifluoroethanone from 3-[4-(4-piperazin-1-yl)benzylidene]-3,4,5,6-tetrahydro[2,3']bipyridinyl

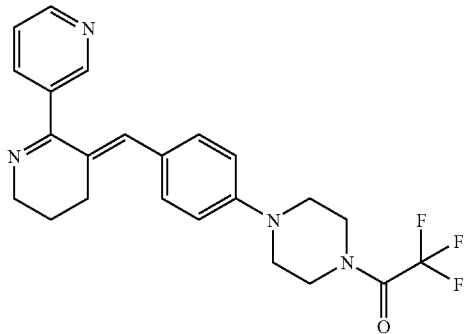

Yield: 42%. ¹H NMR (CDCl₃) δ 8.66 (m, 1H), 8.55 (dd, J=4.9, 1.8, 1H), 7.74 (dt, J_d=7.8, J_t=2.0, 1H), 7.25 (ddd, J=7.8, 4.8, 0.7, 1H), 7.19 (d, J=8.7, 2H), 6.82 (d, J=8.8, 2H), 6.49 (s, 1H), 3.78 (m, 5H), 3.69 (m, 2H), 3.22 (m, 4H), 2.77 (m, 2H), 1.75 (m, 2H), 1.11 (d, J=6.1, 4H); MS (EI) m/z 429 (M⁺+1).

Example 133

Cyclopropyl-{(1S,4S)-5-[4-(5,6-dihydro-4H-[2,3']bipyridinyl-3-ylidenemethyl)phenyl]-2,5-diazabicyclo[2.2.1]hept-2-yl}methanone from 3-{4-[(1S,4S)-2,5-diazabicyclo[2.2.1]hept-2-yl]benzylidene}-3,4,5,6-tetrahydro[2,3']bipyridinyl

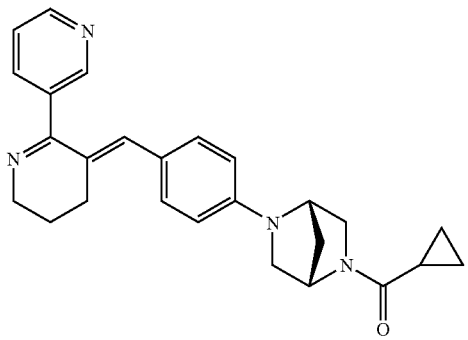

Yield: 59%. ¹H NMR (CDCl₃) δ 8.72 (s, 1H), 8.60 (m, 1H), 7.80 (dt, J_d=7.8, J_t=1.8, 1H), 7.31 (dd, J=7.7, 4.8, 1H), 7.21 (m, 2H), 6.53 (m, 3H), 5.00 (s, 1H), 4.54 (s, 1H), 3.82 (t, J=5.5, 2H), 3.56 (m, 3H), 3.24 (m, 1H), 2.85 (m, 2H), 2.02 (m, 3H), 1.82 (m, 2H), 0.92 (m, 2H), 0.73 (m, 2H); MS (EI) m/z 413 (M⁺+1).

Example 134

Cyclopropyl-{4-[4-(5,6-dihydro-4H-[2,3']bipyridinyl-3-ylidenemethyl)phenyl][1,4]diazepan-1-yl}methanone from 3-[4-([1,4]diazepan-1-yl)benzylidene]-3,4,5,6-tetrahydro[2,3']bipyridinyl

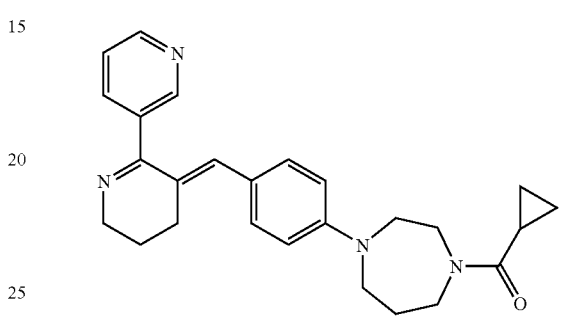

Yield: 54%. ¹H NMR (CDCl₃) δ 8.73 (m, 1H), 8.62 (dd, J=4.9, 1.6, 1H), 7.81 (dt, J_d=7.8, J_t=1.0, 1H), 7.31 (dd, J=7.3, 4.8, 1H), 7.23 (dd, J=8.9, 2.8, 2H), 6.61 (dd, J=8.9, 1.8, 2H), 6.52 (s, 1H), 3.83 (t, J=5.4, 3H), 3.74 (dd, J=10.1, 4.6, 2H), 3.56 (m, 6H), 2.86 (m, 2H), 2.01 (m, 3H), 1.83 (m, 2H), 1.25 (m, 2H), 0.76 (m, 2H); MS (EI) m/z 415 (M⁺+1).

Example 135

1-{(1S,4S)-5-[4-(5,6-Dihydro-4H-[2,3']bipyridinyl-3-ylidenemethyl)phenyl]-2,5-diazabicyclo[2.2.1]hept-2-yl}-2,2,2-trifluoroethanone from 3-{-4-[(1S,4S)-2,5-diazabicyclo[2.2.1]hept-2-yl]benzylidene}-3,4,5,6-tetrahydro[2,3']bipyridinyl

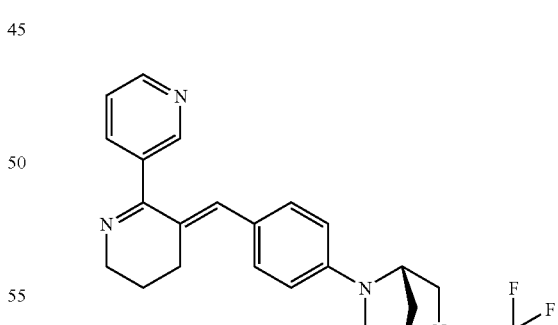

Yield: 47%. ¹H NMR (CDCl₃) δ 8.74 (m, 1H), 8.63 (dd, J=4.8, 1.6, 1H), 7.82 (m, 1H), 7.33 (dd, J=7.8, 4.9, 1H), 7.27 and 7.23 (two d, J=8.3 ea, 2H), 6.55 (s, 1H), 6.53 (d, J=8.5, 2H), 5.08 and 4.84 (two s, 1H tot), 4.58 and 4.55 (two s, 1H tot), 3.84 (t, J=5.5, 1H), 3.68 (m, 3H), 3.26 (m, 1H), 2.85 (m, 2H), 2.09 (m, 3H), 1.84 (m, 2H); MS (EI) m/z 441 (M⁺+1).

Example 136

1-{(1S,4S)-5-[4-(5,6-Dihydro-4H-[2,3']bipyridinyl-3-ylidenemethyl)phenyl]-2,5-diazabicyclo[2.2.1]hept-2-yl}propan-1-one from 3-{4-[(1S,4S)-2,5-diazabicyclo[2.2.1]hept-2-yl]benzylidene}-3,4,5,6-tetrahydro[2,3']bipyridinyl

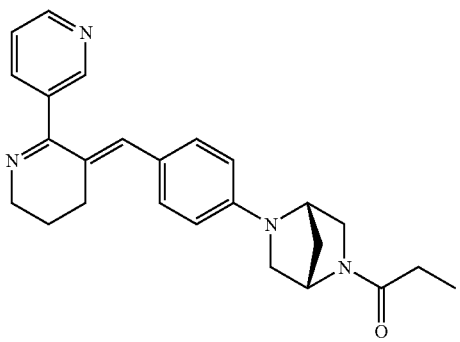

Yield: 74%. ¹H NMR (CDCl₃) δ 8.73 (s, 1H), 8.62 (dd, J=4.8, 1.5, 1H), 7.81 (m, 1H), 7.32 (dd, J=7.8, 4.8, 1H), 7.24 and 7.21 (two d, J=8.5 ea, 2H), 6.52 (m, 3H), 5.02 (s, 0.6H), 4.52 (s, 1H), 4.47 (s, 0.4H), 3.84 (t, J=5.4, 2H), 3.55 (m, 3H), 3.23 and 3.15 (two d, J=9.0, 1H), 2.86 (m, 2H), 2.08 (m, 2H), 1.84 (m, 2H), 1.10 (m, 3H); MS (EI) m/z 401 (M⁺+1).

Example 137

1-{4-[4-(5,6-Dihydro-4H-[2,3']bipyridinyl-3-ylidenemethyl)phenyl][1,4]diazepan-1-yl}-2,2,2-trifluoroethanone from 3-[4-([1,4]diazepan-1-yl)benzylidene]-3,4,5,6-tetrahydro[2,3']bipyridinyl

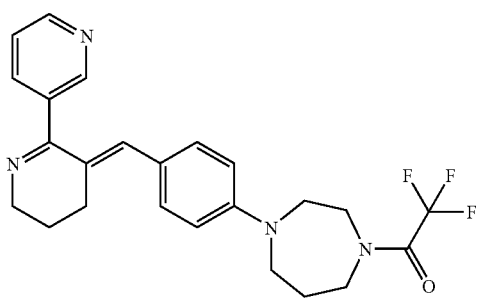

Yield: 49%. ¹H NMR (CDCl₃) δ 8.73 (s, 1H), 8.65 (d, J=3.4, 1H), 7.85 (d, J=7.6, 1H), 7.35 (dd, J=7.5, 4.8, 1H), 7.27 (d, J=7.9, 2H), 6.70 (d, J=7.4, 2H), 6.60 (s, 1H), 3.85 (s, 1H), 3.73 (s, 1H), 3.61 (m, 4H), 3.48 (m, 1H), 3.13 (q, J=7.4, 2H), 2.88 (m, 2H), 2.07, (m, 2H), 1.88 (m, 2H), 1.32 (m, 3H); MS (EI) m/z 443 (M⁺+1).

Example 138

1-{4-[4-(5,6-Dihydro-4H-[2,3']bipyridinyl-3-ylidenemethyl)phenyl][1,4]diazepan-1-yl}propan-1-one from 3-[4-([1,4]diazepan-1-yl)benzylidene]-3,4,5,6-tetrahydro[2,3']bipyridinyl

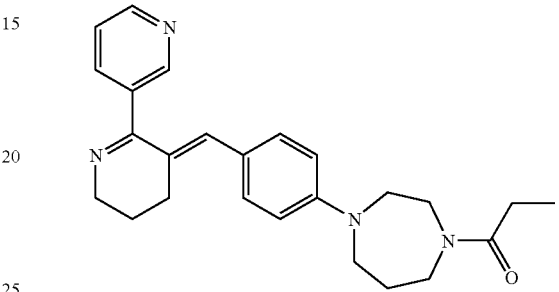

Yield: 73%. ¹H NMR (CDCl₃) δ 8.73 (s, 1H), 8.62 (m, 1H), 7.81 (d, J=7.7, 1H), 7.32 (dd, J=7.5, 4.8, 1H), 7.23 (d, J=7.2, 2H), 6.68 and 6.67 (two d, J=8.6 ea, 2H), 6.52 (s, 1H), 3.83 (t, J=5.2, 2H), 3.75 (m, 1H), 3.60 (m, 6H), 3.41 (m, 2H), 2.86 (s, 2H), 2.34 and 2.26 (two q, J=7.4 ea, 2H), 2.00 (m, 3H), 1.84 (m, 2H), 1.17 and 1.08 (two t, J=7.5 ea, 3H); MS (EI) m/z 403 (M⁺+1).

Example 139

Cyclopropyl-{(1S,4S)-5-[3-(5,6-dihydro-4H-[2,3']bipyridinyl-3-ylidenemethyl)phenyl]-2,5-diazabicyclo[2.2.1]hept-2-yl}methanone from 3-{3-[(1S,4S)-2,5-diazabicyclo[2.2.1]hept-2-yl]benzylidene}-3,4,5,6-tetrahydro[2,3']bipyridinyl

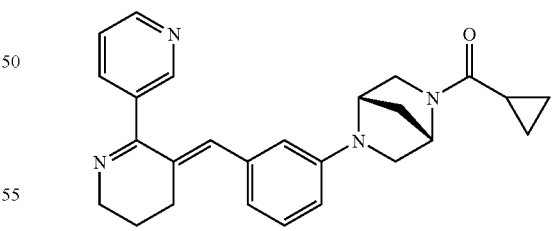

Yield: 30%. ¹H NMR (CDCl₃) δ 8.76 (s, 1H), 8.64 (d, J=3.5, 1H), 7.83 (m, 1H), 7.34 (dd, J=7.7, 4.9, 1H), 7.15 (m, 2H), 6.70 (d, J=7.6, 1H), 6.61 (s, 1H), 6.51 (m, 1H), 6.42 and 6.38 (two s, 1H tot), 5.00 and 4.78 (two s, 1H tot), 4.49 and 4.41 (two s, 1H tot) 3.89 (t, J=5.4, 2H), 3.60 (m, 3H), 3.19 (m, 1H), 2.84 (m, 2H), 2.04 and 1.82 (two m, 6H tot), 1.39 (m, 1H), 0.94 (m, 2H), 0.73 (m, 2H); MS (EI) m/z 413 (M⁺+1).

Example 140

1-{(1S,4S)-5-[3-(5,6-Dihydro-4H-1-[2,3']bipyridinyl-3-ylidenemethyl)phenyl]-2,5-diazabicyclo[2.2.1]hept-2-yl}-2,2,2-trifluoroethanone from 3-{3-[(1S,4S)-2,5-diazabicyclo[2.2.1]hept-2-yl]benzylidene}-3,4,5,6-tetrahydro[2,3']bipyridinyl

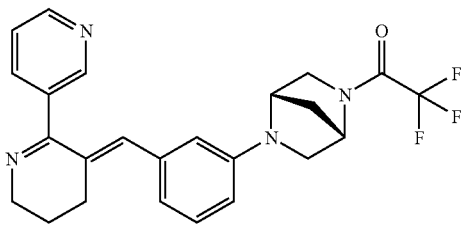

Yield: 18%. $^1$H NMR (CDCl$_3$) δ 8.76 (d, J=2.1, 1H), 8.64 (dd, J=4.9, 1.7, 1H), 7.83 (m, 1H), 7.29 (m, 4H), 6.68 (m, 2H), 6.38 (s, 1H), 5.06 and 4.81 (two s, 1H), 4.52 and 4.49 (two s, 1H), 3.89 (t, J=5.6, 3H), 3.68 (m, 3H), 3.17 (m, 1H), 2.84 (m, 2H), 1.83 (m, 2H); MS (EI) m/z 441 (M$^+$+1).

Example 141

Cyclopropyl-{4-[3-(5,6-dihydro-4H-[2,3']bipyridinyl-3-ylidenemethyl)phenyl]-[1,4]diazepan-1-yl}methanone from 3-[3-([1,4]diazepan-1-yl)benzylidene]-3,4,5,6-tetrahydro[2,3']bipyridinyl

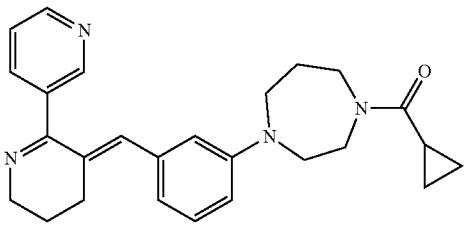

Yield: 38%. $^1$H NMR (CDCl$_3$) δ 8.76 (m, 1H), 8.63 (m, 1H), 7.80 (m, 1H), 7.22 (m, 3H), 6.52 (m, 3H), 6.44 and 6.41 (two s, 1H), 4.41 (m, 1H), 3.89 (s, 2H), 3.60 (m, 1H), 3.51 (s, 2H), 3.10 (m, 1H), 2.82 (s, 2H), 2.04 (m, 4H), 1.82 (m, 3H), 1.12 (m, 4H); MS (EI) m/z 415 (M$^+$+1).

Example 142

1-{4-[3-(5,6-Dihydro-4H-[2,3']bipyridinyl-3-ylidenemethyl)phenyl][1,4]diazepan-1-yl}-2,2,2-trifluoroethanone from 3-[3-([1,4]diazepan-1-yl)benzylidene]-3,4,5,6-tetrahydro[2,3']bipyridinyl

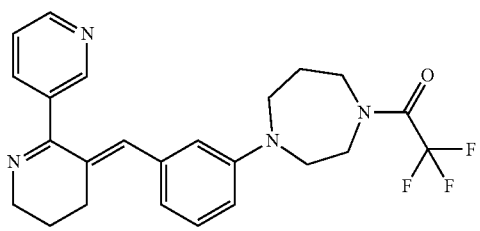

Yield: 10%. $^1$H NMR (CDCl$_3$) δ 8.76 (m, 1H), 8.64 (dd, J=4.9, 1.7, 1H), 7.83 (m, 1H), 7.25 (m, 3H), 6.67 (m, 3H), 6.53 (s, 1H), 3.89 (m, 4H), 3.69 (m, 2H), 3.58 (m, 3H), 2.84 (m, 3H), 1.84 (m, 4H); MS (EI) m/z 443 (M$^+$+1).

Example 143

1-{4-[3-(5,6-Dihydro-4H-[2,3']bipyridinyl-3-ylidenemethyl)phenyl]-[1,4]diazepan-1-yl}propan-1-one from 3-[3-([1,4]diazepan-1-yl)benzylidene]-3,4,5,6-tetrahydro[2,3']bipyridinyl

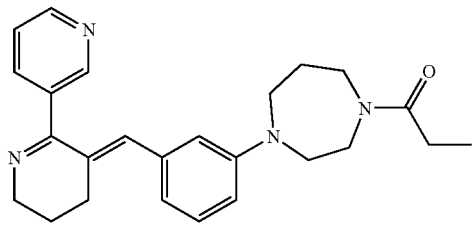

Yield: 23%. $^1$H NMR (CDCl$_3$) δ 8.76 (d, J=0.6, 1H), 8.64 (dd, J=4.8, 1.5, 1H), 7.84 (dt, J$_d$=7.8, J$_t$=2.0, 1H), 7.34 (dd, J=7.8, 4.9, 1H), 7.22 and 7.20 (two d, J=8.0, 2H), 6.67 and 6.62 (two d, J=7.0, 2H), 6.53 (s, 1H), 3.89 (t, J=5.5, 2H), 3.57 (m, 4H), 2.84 (m, 2H), 2.61 (m, 3H), 2.36 (m, 2H), 1.89 (m, 4H), 1.15 (t, J=7.4, 3H); MS (EI) m/z 403 (M$^+$+1).

Representative Procedure F

Example 144

3-(Benzo[1,3]dioxol-5-ylmethylene)-5'-methyl-3,4,5,6-tetrahydro[2,3']bipyridinyl from 5-methylnicotinic acid methyl ester

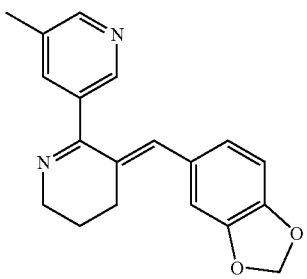

Substituted Anabaseine Preparation:
To a solution of diisopropylamine (4.4 mL, 31.4 mmol) in tetrahydrofuran (20 mL) at −78° C. was added a 2.5 M solution of n-butyllithium in hexanes (12 mL, 30 mmol). The solution was allowed to warm to rt over 30 min and was re-cooled to −78° C. A solution of 1-diethylaminomethyl-piperidin-2-one (3.87 g, 21.0 mmol) in tetrahydrofuran (10 mL) was added to the lithium diisopropylamide via syringe. The reaction mixture was maintained at −78° C. for 1 h and was treated with a solution of 5-methylnicotinic acid methyl ester (2.12 g, 14.0 mmol) in tetrahydrofuran (20 mL) via syringe. The reaction mixture was allowed to warm to rt and was maintained overnight. The reaction mixture was quenched with water (30 mL) and was extracted with ether (2×). The combined organic layers were dried over magnesium sulfate and concentrated in vacuo. The residue was purified by chromatography [1/0 to 1/1 ethyl acetate/(70/30/1 ethyl acetate/methanol/ammonium hydroxide)] to provide 560 mg (13%) of 1-diethylaminomethyl-3-[hydroxy-(5-methylpyridin-3-yl)methylene]piperidin-2-one. To a solution of the piperidin-2-one (550 mg, 1.8 mmol) in acetone (10 mL) was added conc. hydrochloric acid (2 L) and the reaction mixture was heated at 100° C. overnight. The reaction mixture was allowed to cool to rt, diluted with isopropyl alcohol, and allowed to stand at 0° C. The product was isolated by filtration, thus providing 400 mg (85%) of 5'-methyl-3,4,5,6-tetrahydro[2,3']bipyridinyl dihydrochloride.

Condensation:

According to procedure A. Data: Yield: 6%. $^1$H NMR (CDCl$_3$) δ 8.52 (d, J=1.8, 1H), 8.46 (d, J=1.4, 1H), 7.63 (s, 1H), 6.84 (s, 1H), 6.80 (s, 1H), 6.78 (d, J=1.0, 1H), 6.57 (s, 1H), 5.99 (s, 2H), 3.87-3.83 (m, 2H), 2.84-2.79 (m, 2H), 2.37 (s, 3H), 1.85-1.81 (m, 2H); MS (EI) m/z 307 (M$^+$+1).

Using this general procedure the following compounds were prepared:

Example 145

3-(1H-Indol-3-ylmethylene)-5'-methyl-3,4,5,6-tetrahydro[2,3']bipyridinyl from 5-methylnicotinic acid methyl ester

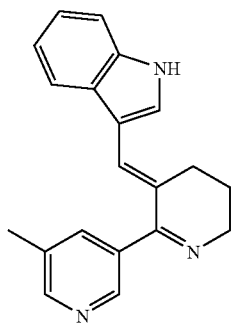

Yield: 2%. $^1$H NMR (CDCl$_3$) δ 8.57 (s, 1H), 8.46 (s, 1H), 7.69 (s, 1H), 7.41 (s, 1H), 7.37 (d, J=8.7, 1H), 7.34 (d, J=8.9, 1H), 7.16 (t, J=7.1, 1H), 7.06 (d, J=7.7, 1H), 3.80-3.76 (m, 2H), 2.76-2.72 (m, 2H), 2.36 (s, 3H), 1.91-1.83 (m, 2H); MS (EI) m/z 302 (M$^+$+1).

Example 146

5'-Methyl-3-(1H-pyrrol-2-ylmethylene)-3,4,5,6-tetrahydro[2,3']bipyridinyl from 5-methylnicotinic acid methyl ester

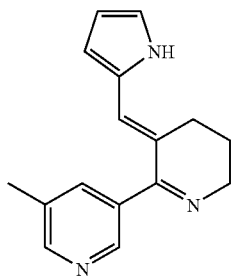

Yield: 8%. $^1$H NMR (CDCl$_3$) δ 9.85 (s, 1H), 8.42 (d, J=1.7, 1H), 8.29 (d, J=1.5, 1H), 7.62 (s, 1H), 6.88 (s, 1H), 6.52 (s, 2H), 6.31 (s, 1H), 3.78-3.74 (m, 2H), 2.78-2.73 (m, 2H), 1.88-1.84 (m, 2H); MS (EI) m/z 252 (M$^+$+1).

Example 147

3-(Benzo[1,3]dioxol-5-ylmethylene)-5'-fluoro-3,4,5,6-tetrahydro[2,3']bipyridinyl from 5-fluoronicotinic acid methyl ester

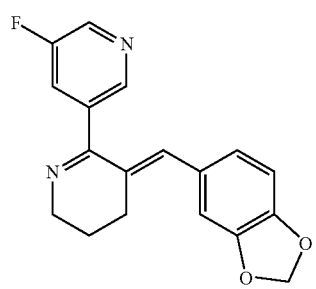

Yield: 7%. $^1$H NMR (CDCl$_3$) δ 8.54 (s, 1H), 8.48 (d, J=2.3, 1H), 7.57-7.52 (m, 1H), 6.83 (s, 1H), 6.81-6.75 (m, 2H), 6.53 (s, 1H), 5.98 (s, 2H), 3.87-3.83 (m, 2H), 2.83-2.78 (m, 2H), 1.86-1.77 (m, 2H); MS (EI) m/z 311 (M$^+$+1).

Example 148

5'-Fluoro-3-(1H-indol-3-ylmethylene)-3,4,5,6-tetrahydro[2,3']bipyridinyl from 5-fluoronicotinic acid methyl ester

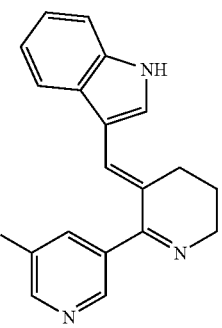

Yield: 3%. $^1$H NMR (CDCl$_3$) δ 8.80 (s, 1H), 8.66 (d, J=1.5, 1H), 8.55 (d, J=2.8, 1H), 7.68-7.63 (m, 1H), 7.48-7.42 (m, 3H), 7.25 (t, J=7.1, 1H), 7.15 (t, J=7.0, 1H), 6.99 (s, 1H), 3.87-3.83 (m, 2H), 2.83-2.80 (m, 2H), 1.94-1.87 (m, 2H); MS (EI) m/z 306 (M$^+$+1).

Example 149

5'-Fluoro-3-(1H-pyrrol-2-ylmethylene)-3,4,5,6-tetrahydro[2,3']bipyridinyl from 5-fluoronicotinic acid methyl ester

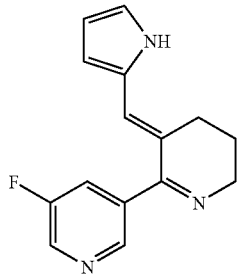

Yield: 2%. $^1$H NMR (CDCl$_3$) δ 8.48 (d, J=2.8, 1H), 8.39 (d, J=2.5, 1H), 7.61-7.54 (m, 1H), 6.89 (s, 1H), 6.53 (s, 1H), 6.48 (s, 1H), 6.35 (s, 1H), 3.79-3.75 (m, 2H), 2.79-2.75 (m, 2H), 1.88-1.81 (m, 2H); MS (EI) m/z 256 (M$^+$+1).

Example 150

3-(2,3-Dihydrobenzo[1,4]dioxin-6-ylmethylene)-5'-fluoro-3,4,5,6-tetrahydro[2,3']bipyridinyl from 5-fluoronicotinic acid methyl ester

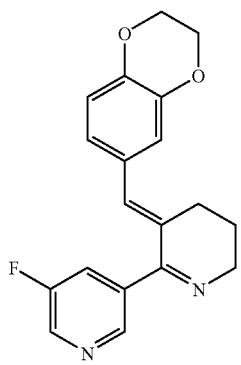

Yield: 3%. $^1$H NMR (CDCl$_3$) δ 8.56 (s, 1H), 8.49 (d, J=2.7, 1H), 7.62-7.55 (m, 1H), 6.88-6.81 (m, 3H), 6.52 (s, 1H), 4.27 (s, 4H), 3.85-3.82 (m, 2H), 2.83-2.79 (m, 2H), 1.84-1.80 (m, 2H); MS (EI) m/z 325 (M$^+$+1).

Example 151

3-(1-Cyclopropylmethyl-1H-pyrrol-2-ylmethylene)-5'-fluoro-3,4,5,6-tetrahydro[2,3']bipyridinyl from 5-fluoronicotinic acid methyl ester

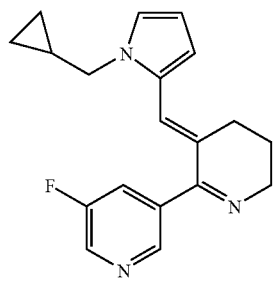

Yield: 11%. $^1$H NMR (CDCl$_3$) δ 8.58 (d, J=1.6, 1H), 8.52 (d, J=2.8, 1H), 7.61-7.57 (m, 1H), 6.89-6.87 (m, 1H), 6.55 (s, 2H), 6.28-6.26 (m, 1H), 3.84-3.81 (m, 2H), 3.58 (d, J=6.6, 2H), 2.81-2.76 (m, 2H), 1.89-1.83 (m, 2H), 0.98-0.93 (m, 1H), 0.56-0.49 (m, 2H), 0.14-0.11 (m, 2H); MS (EI) m/z 310 (M$^+$+1).

Example 152

5'-Fluoro-3-(4-morpholin-4-ylbenzylidene)-3,4,5,6-tetrahydro[2,3']bipyridinyl from 5-fluoronicotinic acid methyl ester

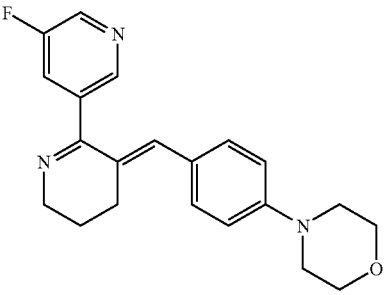

Yield: 3%. $^1$H NMR (CDCl$_3$) δ 8.56-8.54 (m, 1H), 8.46 (s, 1H), 7.73-7.68 (m, 1H), 7.28 (d, J=8.8, 2H), 6.93 (d, J=8.9, 2H), 6.53 (s, 1H), 3.82-3.76 (m, 6H), 3.21-3.17 (m, 4H), 2.91-2.87 (m, 2H), 1.89-1.81 (m, 2H); MS (EI) m/z 352 (M⁺+1).

Example 153

3-(1H-Indol-3-ylmethylene)-6'-trifluoromethyl-3,4,5,6-tetrahydro[2,3']bipyridinyl from 6-trifluoromethylnicotinic acid methyl ester

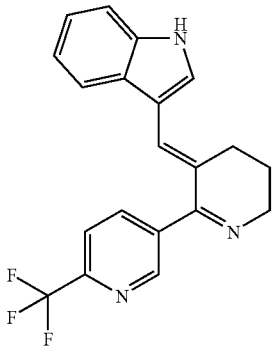

Yield: 6%. ¹H NMR (CDCl₃) δ 8.86 (s, 1H), 8.13 (d, J=7.0, 1H), 7.90 (d, J=7.8, 1H), 7.63 (s, 1H), 7.58 (s, 1H), 7.44 (d, J=8.0, 1H), 7.34 (d, J=8.0, 1H), 7.21 (t, J=7.2, 1H), 7.10 (t, J=7.7, 1H), 6.99 (s, 1H), 3.84-3.80 (m, 2H), 2.91-2.87 (m, 2H), 2.20-1.98 (m, 2H); MS (EI) m/z 356 (M⁺+1).

Representative Procedure G

Example 154

3-(2,3-Dihydrobenzo[1,4]dioxin-6-ylmethylene)-3,4,5,6-tetrahydro[2,3']bipyridinyl Dihydrochloride from 2,3-dihydrobenzo[1,4]dioxine-6-carbaldehyde

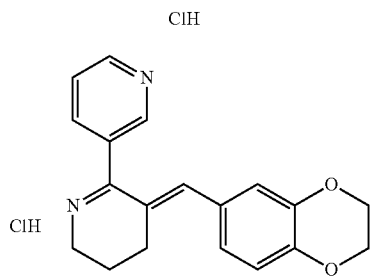

To a solution of 249 mg (1.07 mmol) of anabaseine dihydrochloride in absolute ethanol (5 mL) was added 357 mg (2.17 mmol, 2.0 eq) of the aldehyde and 6 drops of concentrated HCl. The mixture was kept at 60° C. for 14 h and was then diluted with 30 ml of ethyl acetate. The reaction mixture was allowed to cool to rt and the resultant precipitate was collected by filtration and washed with ethyl acetate to afford 314 mg (78%) of the corresponding product. Data: ¹H NMR (DMSO-d₆) δ 8.89 (m, 1H), 8.81 (m, 1H), 8.07 (m, 1H), 7.68 (m, 1H), 7.18 (m, 2H), 6.98 (m, 1H), 4.28 (m, 4H), 3.78 (m, 2H), 2.95 (m, 2H), 2.03 (m, 2H). MS (EI) m/z 307 (M⁺+1).

Using this general procedure the following compounds were prepared:

Example 155

3-(5'Bromo[2,2']bipyrrolyl-5-ylmethylene)-3,4,5,6-tetrahydro[2,3']bipyridinyl Dihydrochloride from 5'-bromo[2,2']bithiophenyl-5-carbaldehyde

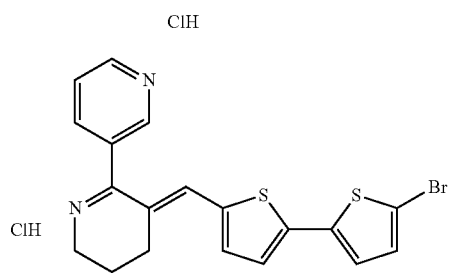

Yield: 50%. ¹H NMR (DMSO-d₆) δ 8.91 (m, 1H), 8.83 (m, 1H), 8.09 (m, 1H), 7.73 (m, 2H), 7.57 (m, 1H), 7.50 (m, 1H), 7.45 (m, 1H), 7.33 (m, 1H), 3.77 (m, 2H), 2.92 (m, 2H), 2.13 (m, 2H); MS (EI) m/z 415, 417 (M⁺+1).

Example 156

5-(5,6-Dihydro-4H-[2,3']bipyridinyl-3-ylidenemethyl)thiophene-2-carboxylic acid Dihydrochloride from 5-formylthiophene-2-carboxylic acid

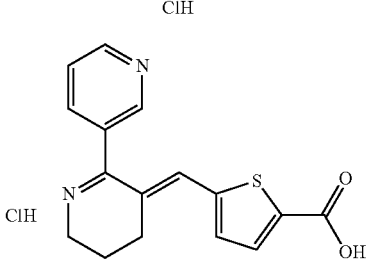

Yield: 55%. $^1$H NMR (DMSO-$d_6$) δ 8.95 (m, 1H), 8.88 (m, 1H), 8.20 (m, 1H), 7.79 (m, 2H), 7.61 (m, 1H), 3.92 (m, 2H), 3.13 (m, 2H), 2.29 (m, 2H); MS (EI) m/z 299 (M$^+$+1).

Example 157

3-[5-(4-Bromophenyl)thiophen-2-ylmethylene]-3,4,5,6-tetrahydro[2,3']bipyridinyl Dihydrochloride from 5-(4-bromophenyl)thiophene-2-carbaldehyde

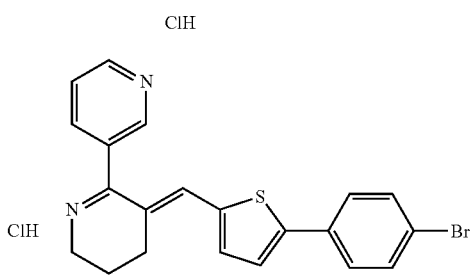

Yield: 50%. $^1$H NMR (DMSO-$d_6$) δ 8.89 (m, 1H), 8.81 (m, 1H), 8.08 (m, 1H), 7.82 (m, 2H), 7.72 (m, 3H), 7.42 (m, 2H), 7.02 (s, 1H), 3.78 (m, 2H), 3.18 (m, 2H), 2.26 (m, 2H); MS (EI) m/z 393, 395 (M$^+$+1).

Example 158

3-[1-(Toluene-4-sulfonyl)-1H-indol-3-ylmethylene]-3,4,5,6-tetrahydro[2,3']bipyridinyl Dihydrochloride from 1-toluenesulfonyl-1H-indole-3-carbaldehyde

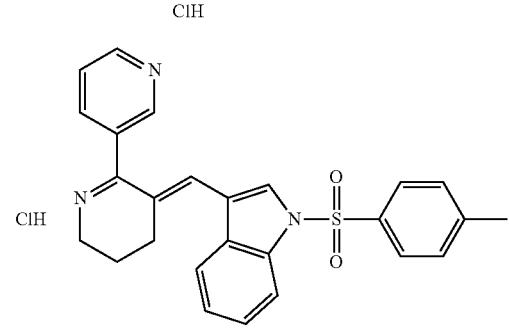

Yield: 55%. $^1$H NMR (DMSO-$d_6$) δ 8.92 (m, 2H), 8.32 (m, 1H), 8.13 (m, 1H), 8.02 (m, 2H), 7.97 (m, 1H), 7.73 (m, 2H), 7.46 (m, 3H), 7.29 (m, 2H), 3.83 (m, 2H), 3.07 (m, 2H), 2.48 (s, 3H), 2.26 (m, 2H); MS (EI) m/z 442 (M$^+$+1).

Example 159

3-[1-Methanesulfonyl-1H-indol-3-ylmethylene]-3,4,5,6-tetrahydro[2,3']bipyridinyl Dihydrochloride from 1-methanesulfonyl-1H-indole-3-carbaldehyde

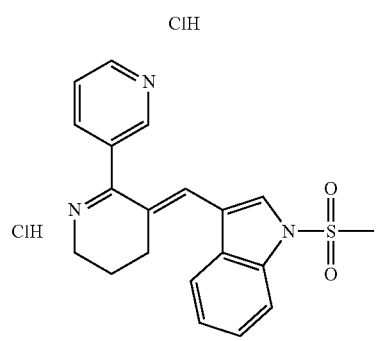

Yield: 55%. $^1$H NMR (DMSO-$d_6$) δ 8.94 (m, 1H), 8.89 (m, 1H), 8.15 (m, 2H), 7.92 (m, 1H), 7.74 (m, 1H), 7.48 (m, 4H), 3.82 (m, 2H), 3.68 (s, 3H), 3.43 (m, 2H), 2.12 (m, 2H); MS (EI) m/z 442 (M$^+$+1).

Example 160

3-(Thiophen-2-ylmethylene)-3,4,5,6-tetrahydro[2,3']bipyridinyl Dihydrochloride from thiophene-2-carbaldehyde

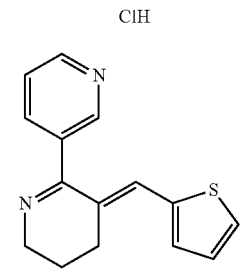

Yield: 50%. $^1$H NMR (CD$_3$OD) δ 9.00 (m, 2H), 8.32 (m, 1H), 8.13 (m, 1H), 7.90 (m, 1H), 7.67 (m, 2H), 7.33 (m, 1H), 3.90 (m, 2H), 3.10 (m, 2H), 2.28 (m, 2H); MS (EI) m/z 255 (M$^+$+1).

Example 161

3-(5-Propylthiophen-2-ylmethylene)-3,4,5,6-tetrahydro[2,3']bipyridinyl Dihydrochloride from 5-propylthiophene-2-carbaldehyde

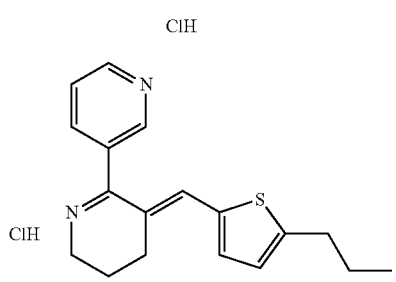

Yield: 50%. $^1$H NMR (DMSO-d$_6$) δ 8.90 (m, 2H), 8.10 (m, 1H), 7.71 (m, 1H), 7.40 (m, 1H), 7.21 (m, 1H), 7.04 (m, 1H), 3.75 (m, 2H), 2.90 (m, 4H), 2.10 (m, 2H), 1.69 (m, 2H), 0.92 (dd, J=6.0 Hz, 3H); MS (EI) m/z 297 (M$^+$+1).

Example 162

3-(5-Bromothiophen-2-ylmethylene)-3,4,5,6-tetrahydro[2,3']bipyridinyl Dihydrochloride from 5-bromothiophene-2-carbaldehyde

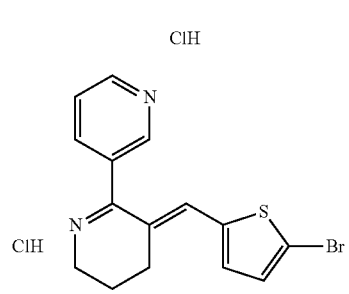

Yield: 40%. $^1$H NMR (DMSO-d$_6$) δ 8.90 (m, 2H), 8.10 (m, 1H), 7.71 (m, 1H), 7.60 (m, 1H), 7.49 (m, 1H), 3.76 (m, 2H), 2.86 (m, 2H), 2.12 (m, 2H); MS (EI) m/z 333, 335 (M$^+$+1).

Example 163

3-(5-Methylthiophen-2-ylmethylene)-3,4,5,6-tetrahydro[2,3']bipyridinyl Dihydrochloride from 5-methylthiophene-2-carbaldehyde

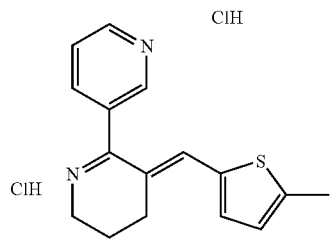

Yield: 60%. $^1$H NMR (DMSO-d$_6$) δ 8.89 (m, 2H), 8.08 (m, 1H), 7.86 (m, 1H), 7.60 (m, 1H), 7.44 (m, 1H), 7.07 (m, 1H), 3.75 (m, 2H), 2.87 (m, 2H), 2.59 (s, 3H), 2.11 (m, 2H); MS (EI) m/z 269 (M$^+$+1).

Example 164

3-(4-Bromothiophen-2-ylmethylene)-3,4,5,6-tetrahydro[2,3']bipyridinyl Dihydrochloride from 3-bromothiophene-2-carbaldehyde

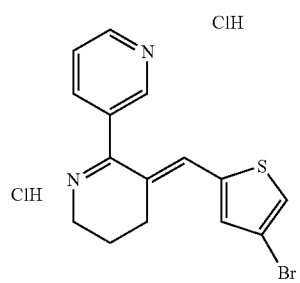

Yield: 40%. $^1$H NMR (DMSO-$d_6$) δ 8.89 (m, 1H), 8.82 (m, 1H), 8.28 (s, 1H), 8.09 (m, 1H), 7.81 (m, 1H), 7.71 (m, 1H), 7.50 (m, 1H), 3.78 (m, 2H), 2.89 (m, 2H), 2.13 (m, 2H); MS (EI) m/z 333, 335 (M$^+$+1).

Example 165

4-[5-(5,6-Dihydro-4H-[2,3']bipyridinyl-3-ylidenemethyl)thiophen-2-yl]phenol Dihydrobromide

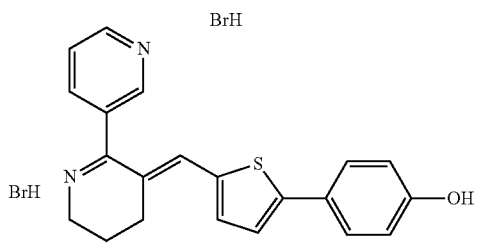

To a −70° C. solution of 3-[5-(4-methoxyphenyl)thiophen-2-ylmethylene]-3,4,5,6-tetrahydro[2,3']bipyridinyl (20 mg, 0.05 mmol) in anhydrous dichloromethane (5 mL) was added 1.0 M BBr$_3$ in dichloromethane (0.5 mL). The reaction mixture was maintained under an atmosphere of N$_2$ at rt. for 6 h and an additional 0.5 ml BBr$_3$ solution was added. The reaction mixture was maintained over night and was quenched with anhydrous methanol (1 mL) at −40° C., and was concentrated to 1 ml. This procedure was repeated twice and the residue was dried under high vacuum. The solid obtained was washed with ethyl acetate and was isolated, thus providing 15 mg of an orange solid. $^1$H NMR (DMSO-$d_6$) δ 8.89 (m, 2H), 8.08 (m, 1H), 7.70 (m, 6H), 6.85 (m, 2H), 3.76 (m, 2H), 2.97 (m, 2H), 2.13 (m, 2H); MS (EI) m/z 347 (M$^+$+1).

Example 166

3-(Benzo[b]thiophen-2-ylmethylene)-3,4,5,6-tetrahydro[2,3']bipyridinyl Dihydrochloride from benzo[b]thiophene-2-carbaldehyde

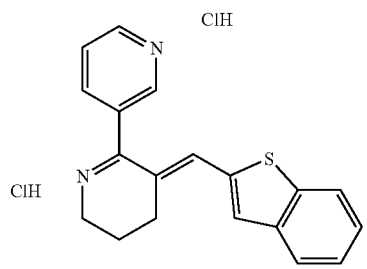

Yield: 60%. $^1$H NMR (DMSO-$d_6$) δ 8.95 (m, 1H), 8.91 (m, 1H), 8.22 (m, 1H), 8.10 (m, 2H), 7.97 (m, 1H), 7.79 (m, 1H), 7.60 (m, 1H), 7.50 (m, 2H), 3.82 (m, 2H), 3.07 (m, 2H), 2.15 (m, 2H); MS (EI) m/z 305 (M$^+$+1).

Example 167

3-(Thiophen-3-ylmethylene)-3,4,5,6-tetrahydro[2,3']bipyridinyl Dihydrochloride from thiophene-3-carbaldehyde

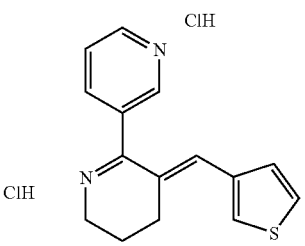

Yield: 60%. $^1$H NMR (DMSO-$d_6$) δ 8.93 (m, 1H), 8.89 (m, 1H), 8.25 (m, 1H), 8.20 (m, 1H), 7.77 (m, 2H), 7.60 (m, 1H), 7.25 (m, 1H), 3.79 (m, 2H), 2.97 (m, 2H), 2.06 (m, 2H); MS (EI) m/z 361 (M$^+$+1).

Example 168

3-(Benzo[b]thiophen-3-ylmethylene)-3,4,5,6-tetrahydro[2,3']bipyridinyl Dihydrochloride from benzo[b]thiophene-3-carbaldehyde

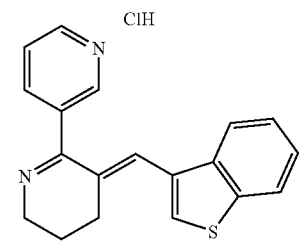

Yield: 60%. $^1$H NMR (DMSO-$d_6$) δ 8.98 (m, 2H), 8.55 (s, 1H), 8.30 (m, 1H), 8.11 (m, 1H), 7.80 (m, 1H), 7.59 (m, 1H), 7.45 (m, 3H), 3.85 (m, 2H), 3.06 (m, 2H), 2.09 (m, 2H); MS (EI) m/z 305 (M$^+$+1).

Example 169

3-(2,3-Dihydrobenzofuran-5-ylmethylene)-3,4,5,6-tetrahydro[2,3']bipyridinyl Dihydrochloride

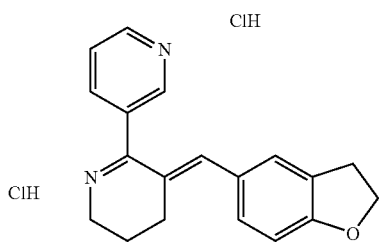

¹H NMR (DMSO-d₆) δ 8.89 (m, 1H), 8.81 (m, 1H), 8.07 (m, 1H), 7.69 (m, 1H), 7.59 (s, 1H), 7.44 (s, 1H), 7.16 (m, 1H), 6.90 (m, 1H), 4.64 (dd, J=9.0, 6.0, 2H), 3.78 (m, 2H), 3.22 (dd, J=9.0, 6.0, 2H), 2.98 (m, 2H), 2.04 (m, 2H). MS (EI) m/z 291 (M⁺+1).

Example 170

3-(3,4-Dihydro-2H-benzo[b][1,4]dioxepin-7-ylmethylene)-3,4,5,6-tetrahydro[2,3']bipyridinyl Dihydrochloride from 3,4-dihydro-2H-benzo[b][1,4]dioxepine-7-carbaldehyde

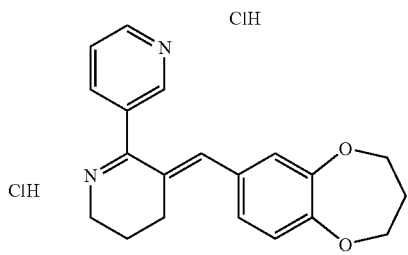

Yield: 81%. ¹H NMR (CD₃OD) δ 9.14 (m, 2H), 8.62 (m, 1H), 8.10 (m, 1H), 7.27-7.25 (m, 3H), 7.04 (d, J=8.9, 1H), 4.30 (t, J=5.6, 1H), 4.23 (t, J=5.8, 2H), 3.94 (t, J=5.6, 2H), 3.15-3.11 (m, 2H), 2.26-2.18 (m, 4H); MS (EI) m/z 321 (M⁺+1).

Example 171

3-(2,2-Dimethylchroman-6-ylmethylene)-3,4,5,6-tetrahydro[2,3']bipyridinyl Dihydrochloride from 2,2-dimethylchroman-6-carbaldehyde

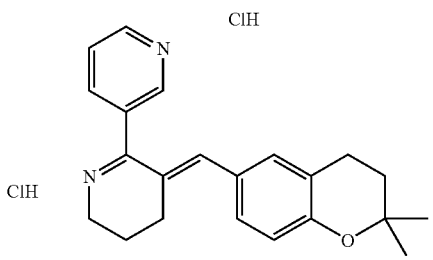

Yield: 71%. ¹H NMR (CD₃OD) δ 9.20-9.11 (m, 2H), 8.81 (m, 1H), 8.29 (m, 1H), 7.50-7.49 (m, 2H), 8.30 (s, 1H), 6.84 (d, J=9.3, 1H), 3.94 (t, J=5.6, 2H), 3.16 (t, J=6.0, 2H), 2.83 (t, J=6.7, 2H), 2.24-2.20 (m, 2H), 1.86 (t, J=6.7, 2H), 1.35 (s, 6H); MS (EI) m/z 333 (M⁺+1).

Example 172

3-(2,2-Difluorobenzo[1,3]dioxol-5-ylmethylene)-3,4,5,6-tetrahydro[2,3']bipyridinyl Dihydrochloride from 2,2-difluorobenzo[1,3]dioxole-5-carbaldehyde

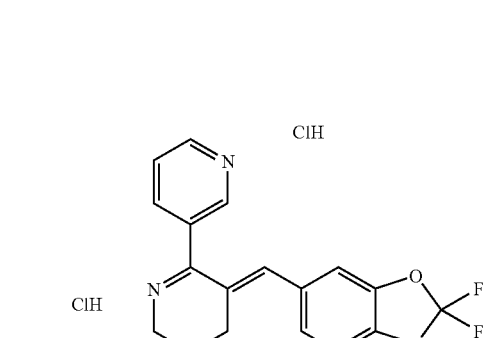

Yield: 97%. ¹H NMR (CD₃OD) δ 9.25-9.14 (m, 2H), 8.78-8.75 (m, 1H), 8.29-8.20 (m, 1H), 7.56 (d, 1H), 7.49 (dd, J=8.5, 1.5, 1H), 7.41 (s, 1H), 7.37 (d, J=8.4, 1H), 4.00 (t, J=5.7, 2H), 3.16-3.11 (m, 2H), 2.24-2.20 (m, 2H); MS (EI) m/z 329 (M⁺+1).

Example 173

3-(7-Methoxybenzo[1,3]dioxol-5-ylmethylene)-3,4,5,6-tetrahydro[2,3']bipyridinyl Dihydrochloride from 7-methoxybenzo[1,3]dioxole-5-carbaldehyde

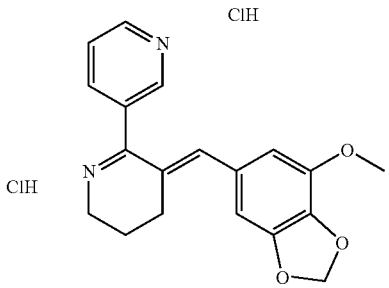

Yield: 84%. ¹H NMR (CD₃OD) δ 8.77-8.72 (m, 1H), 8.27 (m, 1H), 7.31 (s, 1H), 6.96 (s, 2H), 6.08 (s, 2H), 3.95 (t, J=5.6, 2H), 3.89 (s, 3H), 3.17-3.13 (m, 2H), 2.23-2.19 (m, 2H); MS (EI) m/z 323 (M⁺+1).

Example 174

3-(Benzo[1,3]dioxol-5-ylmethylene)-3,4,5,6-tetrahydro[2,3']bipyridinyl Dihydrochloride from benzo[1,3]dioxole-5-carbaldehyde

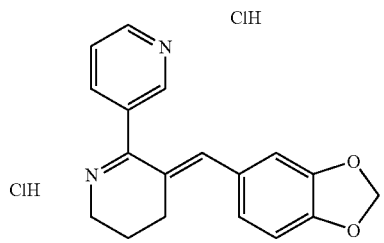

Yield: 78%. ¹H NMR (DMSO-d₆) δ 9.00-8.98 (m, 2H), 8.33-8.30 (m, 1H), 7.89-7.85 (m, 1H), 7.26 (d, J=1.4, 1H), 7.21 (dd, J=8.4, 1.5, 1H), 7.17 (s, 1H), 7.08 (d, J=8.2, 1H), 6.15 (s, 2H), 3.80 (t, J=5.5, 2H), 2.99 (t, J=5.8, 2H), 2.07-2.03 (m, 2H); MS (EI) m/z 293 (M⁺+1).

Example 175

3-(Benzo[1,3]dioxol-4-ylmethylene)-3,4,5,6-tetrahydro[2,3']bipyridinyl Dihydrochloride from benzo[1,3]dioxole-4-carbaldehyde

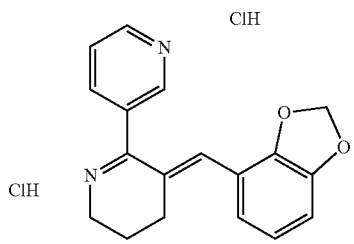

Yield: 82%. ¹H NMR (CD₃OD) δ 9.20-9.10 (m, 2H), 8.70-8.60 (m, 1H), 7.30 (s, 1H), 7.10-7.00 (m, 1H), 6.95-6.80 (m, 2H), 6.05 (s, 2H), 3.95-3.83 (m, 2H), 3.15-3.05 (m, 2H), 2.25-2.15 (m, 2H); MS (EI) m/z 293 (M⁺+1).

Example 176

[³H] MLA Binding

Materials: Rat Brain: Pel-Freez Biologicals, CAT No. 56004-2
Protease inhibitor cocktail tablet: Roche, CAT No. 1697498
Membrane Preparation
Rat brains in 20 vol (w/v) of ice-cold 0.32 M sucrose with protease inhibitors (one tablet per 50 ml) were homogenized with a polytron for 10 sec at setting 11, then centrifuged 10 min at 1000 g, 4° C. The supernatant was centrifuged again for 20 min at 20,000 g, 4° C. The pellets were resuspended in binding buffer (200 mM TRIS-HCl, 20 mM HEPES, pH 7.5, 144 mM NaCl, 1.5 mM KCl, 1 mM MgSO₄, 2 mM CaCl₂, 0.1% (w/v) BSA) and stored membrane prep at −80° C.

For saturation assay, the 200 µl assay mixture in binding buffer contains 200 µg of membrane protein, 0.2 to 44 nM of [³H] MLA. The nonspecific binding was defined using 1 µM MLA. Competition assay was carried out with 2 nM [³H] MLA and a desirable range of compounds. The assay mixture was incubated at 22° C. for 2 hours, then harvested with GF/B filter presoaked with 0.3% PEI in binding buffer using Tomtec harvester. The filter was washed three time with binding buffer and the radioactivity was counted with Trilux.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:
1. A method of treating a patient suffering from nicotine addiction, pain, jetlag, obesity and/or diabetes, or a method of inducing smoking cessation in a patient comprising administering to the patient an effective amount of a compound according to Formula I:

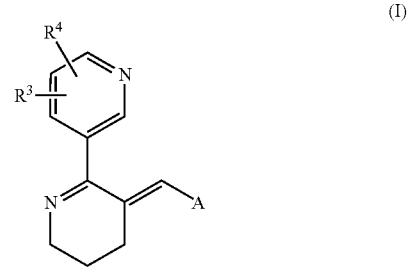

wherein
A is
(a) phenyl or pyridyl, each of which is substituted by a 5 to 7 membered heterocyclic ring containing an O, S, or N ring atom, and optionally containing a further N ring atom, wherein the heterocyclic ring is fully unsaturated, partially saturated or fully saturated and is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms, cycloalkylalkyl having 4 to 14 carbon atoms, Ar-alkyl wherein alkyl portion has 1 to 8 carbon atoms, Het-alkyl wherein alkyl portion has 1 to 8 carbon atoms, COR⁵, COOR⁵, CONR⁵R⁶, halogen, cyano, hydroxyl, NR¹R², nitro, oxo, thio, alkylthio, alkylsulfinyl, alkylsulfonyl, Ar, Het or combinations thereof, wherein the heterocyclic ring may be bridged by a divalent alkylene group having 1 to 3 carbon atoms,
wherein said phenyl or pyridyl is optionally further substituted by one or more substituents selected from halogen, alkyl having 1 to 4 carbon atoms, alkoxy having 1 to 4 carbon atoms, $NR^1R^2$, nitro, hydroxyl, cyano, and or combinations thereof, and wherein said 5 to 7 membered heterocyclic ring is optionally fused with an aryl group or heteroaryl group which in each case contains 5 to 10 ring atoms and in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms, cycloalkylalkyl having 4 to 14 carbon atoms, Ar-alkyl wherein alkyl portion has 1 to 8 carbon atoms, Het-alkyl wherein alkyl portion has 1 to 8 carbon atoms, $COR^5$, $COOR^5$, $CONR^5R^6$, halogen, carboxy, cyano, hydroxyl, $NR^1R^2$, nitro, oxo, thio, Ar, Het and combinations thereof, (b) phenyl or pyridyl which in each case is fused with a 5 to 7 membered heterocyclic ring containing 1 to 3 hetero atoms each selected from O, S, and N, to form a bicyclic group wherein the fused heterocyclic ring is fully unsaturated, partially saturated or fully saturated, and wherein said bicyclic group is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms, cycloalkylalkyl having 4 to 14 carbon atoms, $COR^5$, $COOR^5$, $CONR^5R^6$, halogen, carboxy, cyano, hydroxyl, $NR^1R^2$, nitro, oxo, thio, alkylthio, alkylsulfinyl, alkylsulfonyl, Ar, Het, Ar-alkyl wherein alkyl portion has 1 to 8 carbon atoms, Het-alkyl wherein alkyl portion has 1 to 8 carbon atoms, aroyl having 7 to 15 carbon atoms in which the aryl portion can be substituted by halogen, $C_{1-8}$-alkyl, $C_{1-8}$-alkoxy, nitro, carboxy, hydroxyl, phenoxy, benzyloxy or combinations thereof, wherein said phenyl or pyridyl and/or the fused 5 to 7 membered heterocyclic ring is optionally further substituted by one or more substituents selected from halogen, alkyl having 1 to 4 carbon atoms, alkoxy having 1 to 4 carbon atoms, $NR^1R^2$, nitro, hydroxyl, cyano, and or combinations thereof, and wherein said 5 to 7 membered heterocyclic ring is optionally fused with another aryl group or heteroaryl group which in each case contains 5 to 10 ring atoms and in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms, cycloalkylalkyl having 4 to 14 carbon atoms, Ar-alkyl wherein alkyl portion has 1 to 8 carbon atoms, Het-alkyl wherein alkyl portion has 1 to 8 carbon atoms, $COR^5$, $COOR^5$, $CONR^5R^6$, halogen, carboxy, cyano, hydroxyl, $NR^1R^2$, nitro, oxo, thio, Ar, Het or combinations thereof, or (c) thienyl, pyrrolyl, dithienyl, pyrazolyl, imidazolyl, oxazolyl, isoxazolyl, triazolyl, thiazolyl, or isothiazolyl, each of which is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms, cycloalkylalkyl having 4 to 14 carbon atoms, Ar-alkyl wherein alkyl portion has 1 to 8 carbon atoms, Het-alkyl wherein alkyl portion has 1 to 8 carbon atoms, $COR^5$, $COOR^5$, $CONR^5R^6$, halogen, carboxy, cyano, hydroxyl, $NR^1R^2$, nitro, oxo, thio, Ar, Het or combinations thereof, wherein said thienyl, pyrrolyl, dithienyl, pyrazolyl, imidazolyl, oxazolyl, isoxazolyl, triazolyl, thiazolyl, or isothiazolyl group is optionally fused with another aryl group or heteroaryl group which in each case contains 5 to 10 ring atoms and in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, cycloalkyl having 3 to 10 carbon atoms, cycloalkylalkyl having 4 to 14 carbon atoms, Ar-alkyl wherein alkyl portion has 1 to 8 carbon atoms, Het-alkyl wherein alkyl portion has 1 to 8 carbon atoms, $COR^5$, $COOR^5$, $CONR^5R^6$, halogen, carboxy, cyano, hydroxyl, $NR^1R^2$, nitro, oxo, thio, Ar, Het or combinations thereof;

$R^1$ and $R^2$ are each independently H, alkyl having 1 to 8 carbon atoms or aryl having 6 to 14 carbon atoms;

$R^3$ and $R^4$ are each independently H, alkyl having 1 to 8 carbon atoms, halogenated alkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, or halogen;

$R^5$ and $R^6$ are each independently H, alkyl having 1 to 8 carbon atoms, halogenated alkyl having 1 to 8 carbon atoms, alkenyl having 2 to 8 carbon atoms, alkynyl having 2 to 8 carbon atoms, cycloalkyl having 3 to 10 carbon atoms, cycloalkylalkyl having 4 to 14 carbon atoms, Ar, Het, Ar-alkyl wherein alkyl portion has 1 to 8 carbon atoms, Het-alkyl wherein alkyl portion has 1 to 8 carbon atoms;

Ar is an aryl group containing 6 to 14 carbon atoms which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 10 C atoms and is optionally substituted, aryl having 6 to 10 carbon atoms, aryloxy wherein the aryl portion contains 6 to 14 carbon atoms and is optionally substituted, arylthio wherein the aryl portion contains 6 to 14 carbon atoms and is optionally substituted, cycloalkyloxy wherein the cycloalkyl group has 3 to 10 C atoms and is optionally substituted, sulfo, sulfonylamino, acylamido, acyloxy or combinations thereof; and Het is a heterocyclic group, which is fully saturated, partially saturated or fully unsaturated, having 5 to 14 ring atoms in which at least 1 ring atom is a N, O or S atom, which is substituted one or more times by halogen, aryl having 6 to 14 carbon atoms and is optionally substituted, e.g., alkyl having 1 to 8 C atoms, alkoxy having 1 to 8 C atoms, cyano, trifluoromethyl, nitro, oxo, amino, monoalkylamino having 1 to 8 C atoms, dialkylamino wherein each alkyl group has 1 to 8 C atoms, or combinations thereof; or a pharmaceutically acceptable salt thereof.

2. A method of treating a patient suffering from nicotine addiction, pain, and/or jetlag, or a method of inducing smoking cessation in a patient comprising administering to the patient an effective amount of a compound according to Formula I':

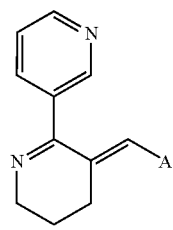

wherein
A is
(a) phenyl or pyridyl, each of which is substituted by a 5 to 7 membered heterocyclic ring containing an O, S, or N ring atom, and optionally containing a further N ring atom, wherein the heterocyclic ring is fully unsaturated, partially saturated or fully saturated and is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het or combinations thereof, wherein said phenyl or pyridyl is optionally further substituted by one or more substituents selected from halogen, alkyl having 1 to 4 carbon atoms, alkoxy having 1 to 4 carbon atoms, $NR^1R^2$, nitro, hydroxyl, and cyano, and wherein said 5 to 7 membered heterocyclic ring is optionally fused with an aryl group or heteroaryl group containing 5 to 10 ring atoms in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het and combinations thereof, (b) phenyl or pyridyl which in each case is fused with a 5 to 7 membered heterocyclic ring containing 1 to 3 hetero atoms each selected from O, S, and N, to form a bicyclic group wherein the fused heterocyclic ring is fully unsaturated, partially saturated or fully saturated, and wherein said bicyclic group is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, alkylthio, alkylsulfinyl, alkylsulfonyl, aryl having 6 to 10 carbon atoms, aralkyl having 7 to 14 carbon atoms, aroyl having 7 to 15 carbon atoms in which the aryl portion can be substituted by halogen, $C_{1-8}$-alkyl, $C_{1-8}$-alkoxy, nitro, carboxy, hydroxyl, phenoxy, benzyloxy or combinations thereof, wherein said phenyl or pyridyl and/or the fused 5 to 7 membered heterocyclic ring is optionally further substituted by one or more substituents selected from halogen, alkyl having 1 to 4 carbon atoms, alkoxy having 1 to 4 carbon atoms, $NR^1R^2$, nitro, hydroxyl, and cyano, and wherein said 5 to 7 membered heterocyclic ring is optionally fused with another aryl group or heteroaryl group containing 5 to 10 ring atoms in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het or combinations thereof, or (c) thienyl, pyrrolyl, dithienyl, pyrazolyl, imidazolyl, oxazolyl, isoxazolyl, triazolyl, thiazolyl, or isothiazolyl, each of which is unsubstituted or substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het or combinations thereof, wherein said thienyl, pyrrolyl, dithienyl, pyrazolyl, imidazolyl, oxazolyl, isoxazolyl, triazolyl, thiazolyl, or isothiazolyl group is optionally fused with another aryl group or heteroaryl group containing 5 to 10 ring atoms in which the heteroaryl group contains 1 to 3 hetero atoms each selected from O, S, and N, and wherein said aryl group or heteroaryl group is optionally substituted one or more times by alkyl having 1 to 8 carbon atoms, halogenated alkyl having 1 to 8 carbon atoms, hydroxyalkyl having 1 to 8 carbon atoms, alkenyl having 2 to 8 carbon atoms, alkynyl having 2 to 8 carbon atoms, alkoxy having 1 to 8 carbon atoms, halogenated alkoxy having 1 to 8 carbon atoms, halogen, carboxy, cyano, hydroxyl, $NR^1R^2$, nitro, oxo, thio, Ar, Het or combinations thereof;

$R^1$ and $R^2$ are each independently H, alkyl having 1 to 8 carbon atoms or aryl having 6 to 10 carbon atoms;

Ar is an aryl group containing 6 to 14 carbon atoms which is unsubstituted or substituted one or more times by alkyl having 1 to 8 C atoms, alkoxy having 1 to 8 C atoms, halogen, dialkylamino wherein the alkyl portions each have 1 to 8 C atoms, amino, cyano, hydroxyl, nitro, halogenated alkyl having 1 to 8 C atoms, halogenated alkoxy having 1 to 8 C atoms, hydroxyalkyl having 1 to 8 C atoms, hydroxyalkoxy having 2 to 8 C atoms, alkenyloxy having 3 to 8 C atoms, alkylthio having 1 to 8 C atoms, alkylsulphinyl having 1 to 8 C atoms, alkylsulphonyl having 1 to 8 C atoms, monoalkylamino having 1 to 8 C atoms, cycloalkylamino wherein the cycloalkyl group has 3 to 10 C atoms and is optionally substituted, aryloxy wherein the aryl portion contains 6 to 14 carbon atoms and is optionally substituted, arylthio wherein the aryl portion contains 6 to 14 carbon atoms and is optionally substituted, cycloalkyloxy wherein the cycloalkyl group has 3 to 10 C atoms and is optionally substituted, sulfo, sulfonylamino, acylamido, acyloxy or combinations thereof; and Het is a heterocyclic group, which is fully saturated, partially saturated or fully unsaturated, having 5 to 14 ring atoms in which at least 1 ring atom is a N, O or S atom, which is substituted one or more times by halogen, aryl having 6 to 14 carbon atoms and is optionally substituted, alkyl having 1 to 8 C atoms, alkoxy having 1 to 8 C atoms, cyano, trifluoromethyl, nitro, oxo, amino, monoalkylamino having 1 to 8 C atoms, dialkylamino wherein each alkyl group has 1 to 8 C atoms, or combinations thereof; or a pharmaceutically acceptable salt thereof.

3. A method according to claim 1, wherein said patient is suffering from nicotine addiction.

4. A method according to claim 1, wherein said patient is suffering from pain.

5. A method according to claim 1, wherein said patient is suffering from jetlag.

6. A method according to claim 1, wherein said patient is suffering from obesity.

7. A method according to claim 1, wherein said patient is suffering from diabetes.

8. A method according to claim 1, wherein said method is for inducing smoking cessation in a patient.

9. A method according to claim 2, wherein said patient is suffering from nicotine addiction.

10. A method according to claim 2, wherein said patient is suffering from pain.

11. A method according to claim 2, wherein said patient is suffering from jetlag.

12. A method according to claim 2, wherein said patient is suffering from obesity.

13. A method according to claim 2, wherein said patient is suffering from diabetes.

14. A method according to claim 2, wherein said method is for inducing smoking cessation in a patient.

* * * * *